(12) United States Patent
Bebernitz et al.

(10) Patent No.: US 8,252,931 B2
(45) Date of Patent: *Aug. 28, 2012

(54) THIAZOLO[5,4-B]PYRIDINE GLUCOKINASE ACTIVATORS

(75) Inventors: Gregory Raymond Bebernitz, Stow, MA (US); Louise Kirman, Marblehead, MA (US)

(73) Assignee: Novartis AG, Basel (CH)

( * ) Notice: Subject to any disclaimer, the term of this patent is extended or adjusted under 35 U.S.C. 154(b) by 860 days.

This patent is subject to a terminal disclaimer.

(21) Appl. No.: 12/088,594

(22) PCT Filed: Sep. 28, 2006

(86) PCT No.: PCT/US2006/038201
§ 371 (c)(1),
(2), (4) Date: Mar. 28, 2008

(87) PCT Pub. No.: WO2007/041366
PCT Pub. Date: Apr. 12, 2007

(65) Prior Publication Data
US 2008/0312256 A1    Dec. 18, 2008

Related U.S. Application Data

(60) Provisional application No. 60/722,630, filed on Sep. 30, 2005.

(51) Int. Cl.
C07D 513/04    (2006.01)
A61K 31/4365    (2006.01)

(52) U.S. Cl. .......................... 546/114; 514/301

(58) Field of Classification Search .............. 546/114; 514/301
See application file for complete search history.

(56) References Cited

U.S. PATENT DOCUMENTS

| | | | |
|---|---|---|---|
| 6,320,050 B1 | 11/2001 | Bizzarro et al. | |
| 6,353,111 B1 | 3/2002 | Corbett et al. | |
| 6,369,232 B1 | 4/2002 | Sidduri | |
| 6,384,220 B2 | 5/2002 | Corbett et al. | |
| 6,388,071 B2 | 5/2002 | Mahaney | |
| 6,388,088 B1 | 5/2002 | Sidduri | |
| 6,433,188 B1 | 8/2002 | Corbett et al. | |
| 6,441,184 B1 | 8/2002 | Corbett et al. | |
| 6,448,399 B1 | 9/2002 | Corbett et al. | |
| 6,486,184 B2 | 11/2002 | Kester et al. | |
| 6,489,485 B2 | 12/2002 | Bizzarro et al. | |
| 6,528,543 B1 | 3/2003 | Bizzarro et al. | |
| 6,545,155 B2 | 4/2003 | Corbett et al. | |
| 6,583,288 B2 | 6/2003 | Goodnow et al. | |
| 6,608,218 B2 | 8/2003 | Kester et al. | |
| 6,610,846 B1 | 8/2003 | Bizzarro et al. | |
| 6,784,298 B2 | 8/2004 | Goodnow et al. | |
| 7,750,020 B2 * | 7/2010 | Bebernitz et al. | 514/301 |
| 7,781,451 B2 * | 8/2010 | Bebernitz et al. | 514/301 |
| 7,795,257 B2 * | 9/2010 | Bebernitz | 514/234.2 |
| 7,812,167 B2 * | 10/2010 | Bebernitz | 546/114 |

| | | |
|---|---|---|
| 2001/0039344 A1 | 11/2001 | Bizzarro et al. |
| 2001/0051731 A1 | 12/2001 | Bizzarro et al. |
| 2001/0053851 A1 | 12/2001 | Mahaney |
| 2001/0056191 A1 | 12/2001 | Goodnow, Jr. et al. |
| 2002/0035266 A1 | 3/2002 | Sidduri |
| 2002/0035267 A1 | 3/2002 | Sidduri |
| 2002/0042512 A1 | 4/2002 | Kester et al. |
| 2002/0082260 A1 | 6/2002 | Guertin |
| 2002/0103241 A1 | 8/2002 | Corbett et al. |
| 2002/0107396 A1 | 8/2002 | Corbett et al. |
| 2002/0198200 A1 | 12/2002 | Kester et al. |
| 2003/0219887 A1 | 11/2003 | Corbett et al. |
| 2003/0225283 A1 | 12/2003 | Corbett et al. |
| 2003/0225286 A1 | 12/2003 | Goodnow, Jr. et al. |
| 2004/0014968 A1 | 1/2004 | Bizzarro et al. |
| 2004/0067939 A1 | 4/2004 | Corbett |
| 2004/0147748 A1 | 7/2004 | Chen et al. |
| 2004/0186290 A1 | 9/2004 | Fyfe et al. |
| 2005/0282851 A1 | 12/2005 | Bebernitz |
| 2007/0265297 A1 | 11/2007 | Bebernitz |
| 2008/0103167 A1 | 5/2008 | Bebernitz |
| 2008/0318948 A1 | 12/2008 | Bebernitz |

FOREIGN PATENT DOCUMENTS

| | | |
|---|---|---|
| DE | 10259786 A1 | 7/2003 |
| GB | 2385328 A | 8/2003 |
| WO | 0058293 A2 | 10/2000 |
| WO | 0144216 A1 | 6/2001 |
| WO | 0183465 A2 | 11/2001 |
| WO | 0183478 A2 | 11/2001 |

(Continued)

OTHER PUBLICATIONS

Brocklehurst et al., "Stimulation of Hepatocyte Glucose Metabolism by Novel Small Molecule Glucokinase Activators" Diabetes 53:535-541 (2004).

Guertin et al., "Small Molecule Glucokinase Activators as Glucose Lowering Agents: A New Paradigm for Diabetes Therapy" Current Medicinal Chemistry 13:1839-1843 (2006).

McKerrecher et al., "Discovery, synthesis and biological evaluation of novel glucokinase activators" Bioorganic & Medicinal Chemistry Letters 15:2103-2106 (2005).

Leighton et al., "Small molecule glucokinase activators as novel anti-diabetic agents" Biochem Soc Trans 33(2) 371-374 (2005).

(Continued)

*Primary Examiner* — David K O Dell
(74) *Attorney, Agent, or Firm* — Joshua Roth

(57) ABSTRACT

The present invention provides compounds of the formula

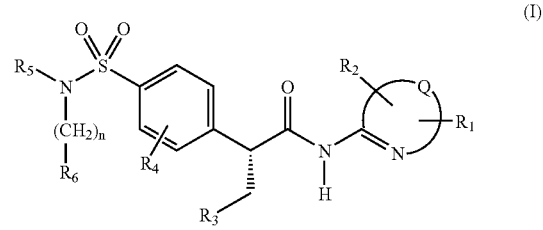

(I)

which are activators of glucokinase activity and, thus, may be employed as therapeutic agents for the treatment of glucokinase mediated conditions. Accordingly, the compounds of formula (I) may be employed for the prevention and the treatment of impaired glucose tolerance, type 2 diabetes and obesity.

9 Claims, No Drawings

FOREIGN PATENT DOCUMENTS

| | | | |
|---|---|---|---|
| WO | 0185706 | A1 | 11/2001 |
| WO | 0185707 | A1 | 11/2001 |
| WO | 0208209 | A1 | 1/2002 |
| WO | 0214312 | A1 | 2/2002 |
| WO | 0248106 | A2 | 6/2002 |
| WO | 03/015774 | A1 | 2/2003 |
| WO | 0355482 | A1 | 7/2003 |
| WO | 03080585 | A1 | 10/2003 |
| WO | 03095438 | A1 | 11/2003 |
| WO | 03097824 | A1 | 11/2003 |
| WO | 2004002481 | A1 | 1/2004 |
| WO | 2004050645 | A1 | 6/2004 |
| WO | 2004052869 | A1 | 6/2004 |
| WO | WO2004/050645 | A1 | 6/2004 |
| WO | 2004063179 | A1 | 7/2004 |
| WO | 2004063194 | A1 | 7/2004 |
| WO | 2004072066 | A1 | 8/2004 |
| WO | WO2004/072031 | A2 | 8/2004 |
| WO | 2004076420 | A1 | 9/2004 |
| WO | 2004081001 | A1 | 9/2004 |
| WO | WO2005/095418 | A | 10/2005 |
| WO | WO 2005095417 | A1 * | 10/2005 |
| WO | 2005103021 | A1 | 11/2005 |
| WO | 2006016194 | A1 | 2/2006 |
| WO | 2006058923 | A1 | 6/2006 |
| WO | 2007041365 | A2 | 4/2007 |
| WO | 2007041366 | A1 | 4/2007 |

OTHER PUBLICATIONS

Coope et al., "Predictive blood glucose lowering efficacy by Glucokinase activators in high fat fed female Zucker rats" British Journal of Pharmacology:1-8 (2006).

"Tweaking the Glucose Sensor: Adjusting Glucokinase Activity with Activator Compounds" Endocrinology 146 (9):3693-3695 (Sep. 2005).

Futamura et al., "An Allosteric Activator of Glucokinase Impairs The Interaction of Glucokinase and Glucokinase Regulatory Protein and Regulates Glucose Metabolism," The Journal of Biological Chemistry, Manuscript M605186200 (Oct. 6, 2006).

McKerrecher et al., "Design of a potent, soluble glucokinase activator with excellent in vivo efficacy" Bioorganic & Medicinal Chemistry Letters (2006).

Grimsby, "Discovery and Actions of Glucokinase Activators" Metabolic Diseases World Summit, Jul. 24-25, 2006.

Sarabu and Grimsby, "Targeting glucokinase activation for the treatment of type 2 diabetes—A status review" Current Opinion in Drug Discovery & Development 8(5):631-637 (2005).

Efanov et al., "A novel glucokinase activator modulates pancreatic islet and hepacyte function" Endocrinology (May 26, 2005).

Matschinsky et al., "The Network of Glucokinase-Expressing Cells in Glucose Homeostasis and the Potential of Glucokinase Activators for Diabetes Therapy" Diabetes 55:1-12 (Jan. 2006).

Grimsby et al., "Allosteric Activators of Glucokinase: Potential Role in Diabetes Therapy" Science 301:370-373 (Jul. 18, 2003).

Castelhano et al., "Glucokinase-activating ureas" Bioorganic & Medicinal Chemistry Letters 15:1501-1504 (2005).

Office Action mailed in U.S. Patent Application Publication No. 2005-0282851 (U.S. Appl. No. 10/529,670) on Sep. 22, 2008.

Office Action mailed in U.S. Patent Application Publication No. 2005-0282851 (U.S. Appl. No. 10/529,670) on Apr. 28, 2009.

Office Action mailed in U.S. Patent Application Publication No. 2008-0103167 (U.S. Appl. No. 11/547,046) on Dec. 19, 2008.

Office Action mailed in U.S. Patent Application Publication No. 2008-0318948 (U.S. Appl. No. 12/088,608) on Sep. 14, 2009.

Office Action mailed in U.S. Patent Application Publication No. 2007-0265297 (U.S. Appl. No. 11/547,227) on Apr. 7, 2009.

* cited by examiner

THIAZOLO[5,4-B]PYRIDINE GLUCOKINASE ACTIVATORS

This application is the National Stage of Application No. PCT/US2006/038201, filed on Sep. 28, 2006, which claims benefit under 35 U.S.C. §119(e) of U.S. Provisional Application No. 60/722,630, filed Sep. 30, 2005, the contents of which are incorporated herein by reference in their entirety.

The present invention relates to certain sulfonamide derivatives, pharmaceutical compositions containing them, and to methods of treating glucokinase mediated conditions, in particular, impaired glucose tolerance and type 2 diabetes, by employing such compounds.

Accordingly, the present invention provides compounds of the formula

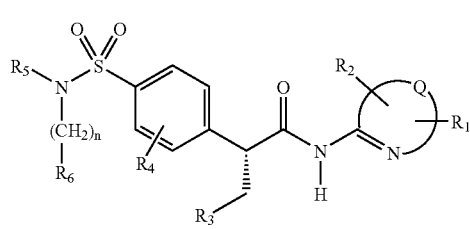

(I)

wherein
  Q combined together with the carbon and nitrogen atoms to which it is attached form a 5- to 6-membered monocyclic heteroaromatic ring; or
  Q combined together with the carbon and nitrogen atoms to which it is attached form a 9- to 10-membered bicyclic heterocycle;
  $R_1$ and $R_2$ are, independently from each other, hydrogen, halogen, cyano, nitro, optionally substituted alkyl, alkoxy, alkylthio, alkylthiono, sulfonyl, free or esterified carboxy, carbamoyl, sulfamoyl, optionally substituted amino, aryl or heterocyclyl; or
  $R_2$ is absent;
  $R_3$ is $(C_{3-6})$cycloalkyl or $(C_{3-6})$heterocyclyl;
  $R_4$ is hydrogen, halogen, cyano, lower alkyl or lower alkoxy;
  $R_5$ is $(C_{3-12})$cycloalkyl, $(C_{6-10})$aryl, $(C_{3-10})$heterocyclyl or $(C_{1-6})$alkyl optionally substituted by $(C_{1-6})$alkoxy, $(C_{1-2})$alkoxy-$(C_{1-4})$alkoxy, $(C_{1-6})$alkylthio, $(C_{3-7})$cycloalkyl, $(C_{3-7})$cycloalkoxy, $(C_{3-7})$cycloalkylthio, $(C_{6-10})$aryl, $(C_{6-10})$aryloxy, $(C_{6-10})$arylthio, $(C_{3-10})$heterocyclyl or $(C_{3-10})$heterocyclyloxy;
  $R_6$ is free or esterified carboxy, tetrazolyl, cyano or —C(O)NR$_7$R$_8$ in which
    $R_7$ and $R_8$ are, independently from each other, hydrogen, optionally substituted alkyl, cycloalkyl, aryl or heterocyclyl; or
    $R_7$ and $R_8$ combined are alkylene which together with the nitrogen atom to which they are attached form a 4- to 7-membered ring;
  n is an integer from 1 to 6;
or an enantiomer thereof; or an enantiomeric mixture thereof; or a pharmaceutically acceptable salt thereof.

The compounds of the present invention provide pharmacological agents which are glucokinase activators and, thus, may be employed for the treatment of glucokinase mediated conditions. Accordingly, the compounds of formula (I) may be employed for prevention and treatment of impaired glucose tolerance, type 2 diabetes and obesity.

Listed below are definitions of various terms used to describe the compounds of the present invention. These definitions apply to the terms as they are used throughout the specification unless they are otherwise limited in specific instances either individually or as part of a larger group, e.g., wherein an attachment point, of a certain group is limited to a specific atom within that group, the point of attachment is defined by an arrow at the specific atom.

The term "optionally substituted alkyl" refers to unsubstituted or substituted alkyl groups, i.e., straight- or branched-chain hydrocarbon groups having 1-20 carbon atoms, preferably 1-10 carbon atoms. Exemplary unsubstituted alkyl groups include methyl, ethyl, propyl, isopropyl, n-butyl, t-butyl, isobutyl, pentyl, hexyl, isohexyl, heptyl, 4,4-dimethylpentyl, octyl and the like. Substituted alkyl groups include, but are not limited to, alkyl groups substituted by one or more of the following groups: halogen, hydroxy, alkanoyl, alkoxy, alkanoyloxy, thiol, alkylthio, alkylthiono, sulfonyl, sulfamoyl, carbamoyl, cyano, carboxy, acyl, aryl, alkenyl, alkynyl, aralkoxy, guanidino, optionally substituted amino, heterocyclyl including imidazolyl, furyl, thienyl, thiazolyl, pyrrolidyl, pyridyl, pyrimidyl and the like.

The term "lower alkyl" refers to those alkyl groups as described above having 1-7, preferably 2-4 carbon atoms.

The term "halogen" or "halo" refers to fluorine, chlorine, bromine and iodine.

The term "alkenyl" refers to any of the above alkyl groups having at least two carbon atoms and further containing a carbon to carbon double bond at the point of attachment. Groups having 2-4 carbon atoms are preferred.

The term "alkynyl" refers to any of the above alkyl groups having at least two carbon atoms and further containing a carbon to carbon triple bond at the point of attachment. Groups having 2-4 carbon atoms are preferred.

The term "alkylene" refers to a straight-chain bridge of 3-6 carbon atoms connected by single bonds, e.g., —(CH$_2$)$_x$—, wherein x is 3-6, which may be interrupted with one or more heteroatoms selected from O, —O—C(O)—, S, S(O), S(O)$_2$ or NR, wherein R may be hydrogen, alkyl, cycloalkyl, aryl, heterocyclyl, aralkyl, heteroaralkyl, acyl, carbamoyl, sulfonyl, alkoxycarbonyl, aryloxycarbonyl or aralkoxycarbonyl and the like; and the alkylene may further be substituted with one or more substituents selected from optionally substituted alkyl, cycloalkyl, aryl, heterocyclyl, oxo, halogen, hydroxy, carboxy, alkoxy, alkoxycarbonyl and the like.

The term "cycloalkyl" refers to optionally substituted monocyclic, bicyclic or tricyclic hydrocarbon groups of 3-12 carbon atoms, each of which may contain one or more carbon to carbon double bonds, or the cycloalkyl may be substituted by one or more substituents, such as alkyl, halo, oxo, hydroxy, alkoxy, alkanoyl, acylamino, carbamoyl, alkylamino, dialkylamino, thiol, alkylthio, cyano, carboxy, alkoxycarbonyl, sulfonyl, sulfonamido, sulfamoyl, heterocyclyl and the like.

Exemplary monocyclic hydrocarbon groups include, but are not limited to, cyclopropyl, cyclobutyl, cyclopentyl, cyclopentenyl, cyclohexyl and cyclohexenyl and the like.

Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like.

Exemplary tricyclic hydrocarbon groups include adamantyl and the like.

The term "alkoxy" refers to alkyl-O—.
The term "alkanoyl" refers to alkyl-C(O)—.
The term "alkanoyloxy" refers to alkyl-C(O)—O—.
The terms "alkylamino" and "dialkylamino" refer to alkyl-NH— and (alkyl)$_2$N—, respectively.
The term "alkanoylamino" refers to alkyl-C(O)—NH—.
The term "alkylthio" refers to alkyl-S—.
The term "trialkylsilyl" refers to (alkyl)$_3$Si—.
The term "trialkylsilyloxy" refers to (alkyl)$_3$SiO—.
The term "alkylthiono" refers to alkyl-S(O)—.

The term "alkylsulfonyl" refers to alkyl-S(O)$_2$—.

The term "alkoxycarbonyl" refers to alkyl-O—C(O)—.

The term "alkoxycarbonyloxy" refers to alkyl-O—C(O) O—.

The term "carbamoyl" refers to H$_2$NC(O)—, alkyl-NHC(O)—, (alkyl)$_2$NC(O)—, aryl-NHC(O)—, alkyl(aryl)-NC(O)—, heteroaryl-NHC(O)—, alkyl(heteroaryl)-NC(O)—, aralkyl-NHC(O)—, alkyl(aralkyl)-NC(O)— and the like.

The term "sulfamoyl" refers to H$_2$NS(O)$_2$—, alkyl-NHS(O)$_2$—, (alkyl)$_2$NS(O)$_2$—, aryl-NHS(O)$_2$—, alkyl(aryl)-NS(O)$_2$—, (aryl)$_2$NS(O)$_2$—, heteroaryl-NHS(O)$_2$—, aralkyl-NHS(O)$_2$—, heteroaralkyl-NHS(O)$_2$— and the like.

The term "sulfonamido" refers to alkyl-S(O)$_2$—NH—, aryl-S(O)$_2$—NH—, aralkyl-S(O)$_2$—NH—, heteroaryl-S(O)$_2$—NH—, heteroaralkyl-S(O)$_2$—NH—, alkyl-S(O)$_2$—N(alkyl)-, aryl-S(O)$_2$—N(alkyl)-, aralkyl-S(O)$_2$—N(alkyl)-, heteroaryl-S(O)$_2$—N(alkyl)-, heteroaralkyl-S(O)$_2$—N(alkyl)- and the like.

The term "sulfonyl" refers to alkylsulfonyl, arylsulfonyl, heteroarylsulfonyl, aralkylsulfonyl, heteroaralkylsulfonyl and the like.

The term "optionally substituted amino" refers to an amino group which may optionally be substituted by substituents such as optionally substituted alkyl, acyl, sulfonyl, alkoxycarbonyl, cycloalkoxycarbonyl, aryloxycarbonyl, heteroaryloxycarbonyl, aralkoxycarbonyl, heteroaralkoxycarbonyl, carbamoyl and the like.

The term "aryl" refers to monocyclic or bicyclic aromatic hydrocarbon groups having 6-12 carbon atoms in the ring portion, such as phenyl, biphenyl, naphthyl and tetrahydronaphthyl, each of which may optionally be substituted by 1-4 substituents, such as optionally substituted alkyl, trifluoromethyl, cycloalkyl, halo, hydroxy, alkoxy, acyl, alkanoyloxy, aryloxy, optionally substituted amino, thiol, alkylthio, arylthio, nitro, cyano, carboxy, alkoxycarbonyl, carbamoyl, alkylthiono, sulfonyl, sulfonamido, heterocyclyl and the like.

The term "monocyclic aryl" refers to optionally substituted phenyl as described under aryl.

The term "aralkyl" refers to an aryl group bonded directly through an alkyl group, such as benzyl.

The term "aralkanoyl" refers to aralkyl-C(O)—.

The term "aralkylthio" refers to aralkyl-S—.

The term "aralkoxy" refers to an aryl group bonded directly through an alkoxy group.

The term "arylsulfonyl" refers to aryl-S(O)$_2$—.

The term "arylthio" refers to aryl-S—.

The term "aroyl" refers to aryl-C(O)—.

The term "aroyloxy" refers to aryl-C(O)—O—.

The term "aroylamino" refers to aryl-C(O)—NH—.

The term "aryloxycarbonyl" refers to aryl-O—C(O)—.

The term "heterocyclyl" or "heterocycle" refers to an optionally substituted, fully saturated or unsaturated, aromatic or nonaromatic cyclic group, e.g., which is a 4- to 7-membered monocyclic, 7- to 12-membered bicyclic or 10- to 15-membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized. The heterocyclic group may be attached at a heteroatom or a carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, triazolyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, 1,1,4-trioxo-1,2,5-thiadiazolidin-2-yl and the like.

Exemplary bicyclic heterocyclic groups include indolyl, dihydroidolyl, benzothiazolyl, 4,5,6,7-tetrahydro-benzothiazolyl, benzoxazinyl, benzoxazolyl, benzothienyl, benzothiazinyl, thiazolo[5,4-b]pyridinyl, thiazolo[5,4-d]pyrimidinyl, oxazolo[5,4-b]pyridinyl, 6,7-dihydro-4H-thiopyrano[4,3-d]thiazolyl, 6,7-dihydro-4H-pyrano[4,3-d]thiazolyl, 4,5,6,7-tetrahydro-thiazolo[5,4-c]pyridinyl, 4,5,6,7-tetrahydro-pyrazolo[1,5-a]pyridinyl, 5,6,7,8-tetrahydro-triazolo[1,5-a]pyridinyl, quinuclidinyl, quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]-pyridinyl] or furo[2,3-b]pyridinyl), dihydroisoindolyl, 1,3-dioxo-1,3-dihydroisoindol-2-yl, dihydroquinazolinyl (such as 3,4-dihydro-4-oxo-quinazolinyl), phthalazinyl and the like.

Exemplary tricyclic heterocyclic groups include carbazolyl, dibenzoazepinyl, dithienoazepinyl, benzindolyl, phenanthrolinyl, acridinyl, phenanthridinyl, phenoxazinyl, phenothiazinyl, xanthenyl, carbolinyl and the like.

The term "heterocyclyl" includes substituted heterocyclic groups. Substituted heterocyclic groups refer to heterocyclic groups substituted with 1, 2 or 3 substituents selected from the group consisting of the following:

(a) optionally substituted alkyl;
(b) hydroxyl (or protected hydroxyl);
(c) halo;
(d) oxo, i.e., =O;
(e) optionally substituted amino;
(f) alkoxy;
(g) cycloalkyl;
(h) free or esterified carboxy;
(i) heterocyclyl;
(j) alkylthio;
(k) alkylthiono;
(l) nitro;
(m) cyano;
(n) sulfamoyl;
(o) alkanoyloxy;
(p) aroyloxy;
(q) arylthio;
(r) aryloxy;
(s) sulfamoyl;
(t) sulfonyl;
(u) carbamoyl;
(v) aralkyl; and
(w) aryl optionally substituted with alkyl, cycloalkyl, alkoxy, hydroxyl, amino, acylamino, alkylamino, dialkylamino or halo.

The term "heterocyclooxy" denotes a heterocyclic group bonded through an oxygen bridge.

The term "heteroaryl" refers to an aromatic heterocycle, e.g., monocyclic or bicyclic aryl, such as pyrrolyl, pyrazolyl, imidazolyl, triazolyl, oxazolyl, isoxazolyl, thiazolyl, isothiazolyl, furyl, thienyl, pyridyl, pyrazinyl, pyrimidinyl, pyridazinyl, indolyl, benzothiazolyl, benzoxazolyl, benzothienyl, quinolinyl, isoquinolinyl, benzimidazolyl, benzofuryl and the like, optionally substituted by, e.g., lower alkyl, lower alkoxy or halo.

The term "heteroarylsulfonyl" refers to heteroaryl-S(O)$_2$—.

The term "heteroaroyl" refers to heteroaryl-C(O)—.

The term "heteroaryloxycarbonyl" refers to heteroaryl-O—C(O)—.

The term "heteroaroylamino" refers to heteroaryl-C(O)NH—.

The term "heteroaralkyl" refers to a heteroaryl group bonded through an alkyl group.

The term "heteroaralkanoyl" refers to heteroaralkyl-C(O)—.

The term "heteroaralkanoylamino" refers to heteroaralkyl-C(O)NH—.

The term "acyl" refers to alkanoyl, aroyl, heteroaroyl, aralkanoyl, heteroaralkanoyl and the like.

The term "acylamino" refers to alkanoylamino, aroylamino, heteroaroylamino, aralkanoylamino, heteroaralkanoylamino and the like.

The term "esterified carboxy" refers to optionally substituted alkoxycarbonyl, cycloalkoxycarbonyl, aryloxycarbonyl, aralkoxycarbonyl, heterocyclooxycarbonyl and the like.

Pharmaceutically acceptable salts of the compounds of the present invention refer to salts formed with acids, namely acid addition salts, such as of mineral acids, organic carboxylic acids and organic sulfonic acids, e.g., hydrochloric acid, maleic acid and methanesulfonic acid, respectively.

Similarly, pharmaceutically acceptable salts of the compounds of the invention refer to salts formed with bases, namely cationic salts, such as alkali and alkaline earth metal salts, e.g., sodium, lithium, potassium, calcium and magnesium, as well as ammonium salts, e.g., ammonium, trimethylammonium, diethylammonium and tris(hydroxymethyl)-methyl-ammonium salts and salts with amino acids provided an acidic group constitutes part of the structure.

As described herein above, the present invention provides certain sulfonamide derivatives of formula (I), pharmaceutical compositions containing them, methods for preparing said compounds, and methods of treating glucokinase mediated conditions by administration of a therapeutically effective amount of a compound of the present invention, or a pharmaceutical composition thereof.

Preferred are the compounds of formula (I) wherein
  $R_3$ is cyclopentyl;
  $R_4$ is hydrogen;
  $R_6$ is free or esterified carboxy;
or an enantiomer thereof; or an enantiomeric mixture thereof; or a pharmaceutically acceptable salt thereof.

Further preferred are the compounds of formula (I), designated as the A group, having the formula

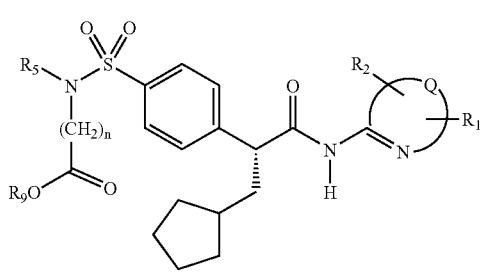

(IA)

wherein
  $R_9$ is hydrogen, optionally substituted lower alkyl, lower alkenyl, cycloalkyl, aryl or aralkyl;
  Q combined together with the carbon and nitrogen atoms to which it is attached form a 5- to 6-membered monocyclic heteroaromatic ring which is selected from the group consisting of

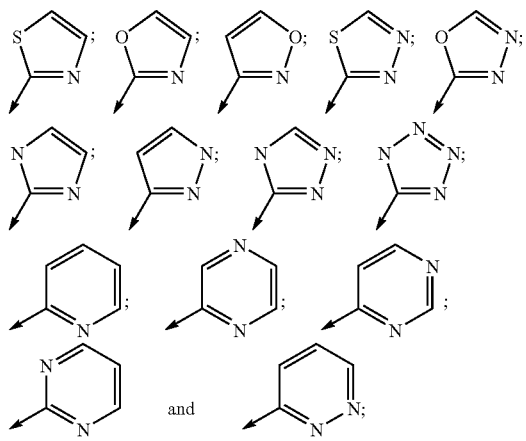

or an enantiomer thereof; or an enantiomeric mixture thereof; or a pharmaceutically acceptable salt thereof.

Preferred are the compounds in the A group wherein
  n is an integer from 1 to 3;
or an enantiomer thereof; or an enantiomeric mixture thereof; or a pharmaceutically acceptable salt thereof.

More preferred are the compounds in the A group wherein
  n is an integer from 1 to 3;
  $R_9$ is hydrogen;
or an enantiomer thereof; or an enantiomeric mixture thereof; or a pharmaceutically acceptable salt thereof.

More preferred are also the compounds in the A group wherein
  n is an integer from 1 to 3;
  $R_1$ is hydrogen, halogen, cyano, trifluoromethyl, alkoxy, alkylthio or carboxy;
  $R_2$ is absent;
or an enantiomer thereof; or an enantiomeric mixture thereof; or a pharmaceutically acceptable salt thereof.

Most preferred are the compounds in the A group, designated as the B group, wherein
  n is an integer from 1 to 3;
  $R_1$ is hydrogen, halogen, cyano, trifluoromethyl, alkoxy, alkylthio or carboxy;
  $R_2$ is absent;
  Q combined together with the carbon and nitrogen atoms to which it is attached form a 5- to 6-membered monocyclic heteroaromatic ring which is selected from the group consisting of

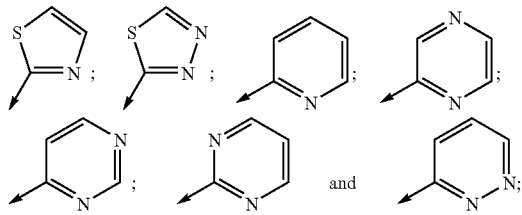

or an enantiomer thereof; or an enantiomeric mixture thereof; or a pharmaceutically acceptable salt thereof.

Preferred are the compounds in the B group wherein
  $R_5$ is $(C_{3-7})$cycloalkyl or $(C_{1-4})$alkyl substituted by $(C_{1-6})$alkoxy, $(C_{3-7})$cycloalkyl, $(C_{6-10})$aryl or $(C_{5-6})$heterocyclyl;

or an enantiomer thereof; or an enantiomeric mixture thereof; or a pharmaceutically acceptable salt thereof.

More preferred are the compounds in the B group wherein
$R_5$ is $(C_{3-7})$cycloalkyl or $(C_{1-4})$alkyl substituted by $(C_{1-6})$alkoxy, $(C_{3-7})$cycloalkyl, $(C_{6-10})$aryl or $(C_{5-6})$heterocyclyl;
$R_9$ is hydrogen;
or an enantiomer thereof; or an enantiomeric mixture thereof; or a pharmaceutically acceptable salt thereof.

Most preferred are the compounds in the B group wherein
$R_5$ is $(C_{3-7})$cycloalkyl or $(C_{1-4})$alkyl substituted by $(C_{1-6})$alkoxy, $(C_{3-7})$cycloalkyl, $(C_{6-10})$aryl or $(C_{5-6})$heterocyclyl in which $(C_{1-4})$alkyl is methyl or ethyl, $(C_{1-6})$alkoxy is methoxy or ethoxy; and $(C_{6-10})$aryl is optionally substituted phenyl;
$R_9$ is hydrogen;
or an enantiomer thereof; or an enantiomeric mixture thereof; or a pharmaceutically acceptable salt thereof.

Further preferred are also the compounds of formula (I), designated as the C group, having the formula

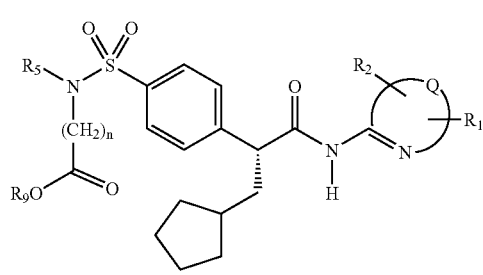

(IA)

wherein
$R_9$ is hydrogen, optionally substituted lower alkyl, lower alkenyl, cycloalkyl, aryl or aralkyl;
Q combined together with the carbon and nitrogen atoms to which it is attached form a 9- to 10-membered bicyclic heterocycle which is selected from the group consisting of

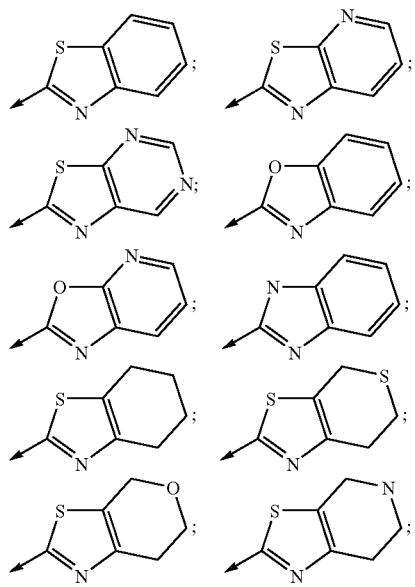

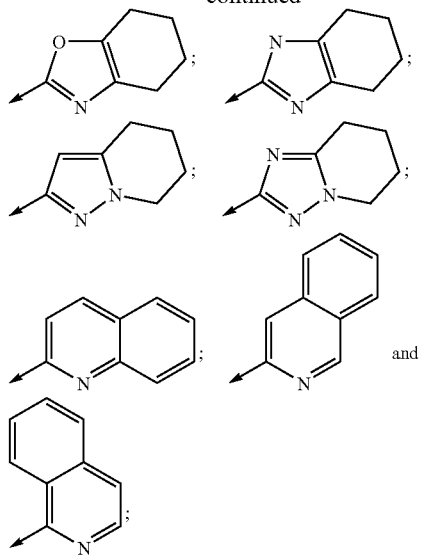

or an enantiomer thereof; or an enantiomeric mixture thereof; or a pharmaceutically acceptable salt thereof.

Preferred are the compounds in the C group wherein
n is an integer from 1 to 3;
or an enantiomer thereof; or an enantiomeric mixture thereof; or a pharmaceutically acceptable salt thereof.

More preferred are the compounds in the C group wherein
n is an integer from 1 to 3;
$R_9$ is hydrogen;
or an enantiomer thereof; or an enantiomeric mixture thereof; or a pharmaceutically acceptable salt thereof.

More preferred are also the compounds in the C group wherein
n is an integer from 1 to 3;
$R_1$ is hydrogen, halogen, cyano, trifluoromethyl, alkoxy, alkylthio or carboxy;
$R_2$ is absent;
or an enantiomer thereof; or an enantiomeric mixture thereof; or a pharmaceutically acceptable salt thereof.

Most preferred are the compounds in the C group, designated as the D group, wherein
n is an integer from 1 to 3;
$R_1$ is hydrogen, halogen, cyano, trifluoromethyl, alkoxy, alkylthio or carboxy;
$R_2$ is absent;
Q combined together with the carbon and nitrogen atoms to which it is attached form a 9- to 10-membered bicyclic heterocycle which is selected from the group consisting of

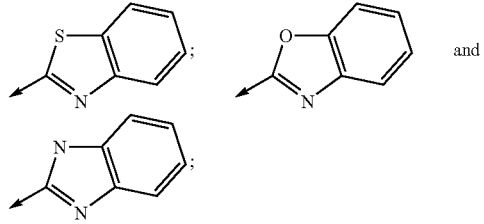

or an enantiomer thereof; or an enantiomeric mixture thereof; or a pharmaceutically acceptable salt thereof.

Preferred are the compounds in the D group wherein
$R_5$ is $(C_{3-7})$cycloalkyl or $(C_{1-4})$alkyl substituted by $(C_{1-6})$alkoxy, $(C_{3-7})$cycloalkyl, $(C_{6-10})$aryl or $(C_{5-6})$heterocyclyl;

or an enantiomer thereof; or an enantiomeric mixture thereof; or a pharmaceutically acceptable salt thereof.

More preferred are the compounds in the D group wherein
$R_5$ is $(C_{3-7})$cycloalkyl or $(C_{1-4})$alkyl substituted by $(C_{1-6})$alkoxy, $(C_{3-7})$cycloalkyl, $(C_{6-10})$aryl or $(C_{5-6})$heterocyclyl;
$R_9$ is hydrogen;

or an enantiomer thereof; or an enantiomeric mixture thereof; or a pharmaceutically acceptable salt thereof.

Most preferred are the compounds in the D group wherein
$R_5$ is $(C_{3-7})$cycloalkyl or $(C_{1-4})$alkyl substituted by $(C_{1-6})$alkoxy, $(C_{3-7})$cycloalkyl, $(C_{6-10})$aryl or $(C_{5-6})$heterocyclyl in which $(C_{1-4})$alkyl is methyl or ethyl, $(C_{1-6})$alkoxy is methoxy or ethoxy; and $(C_{6-10})$aryl is optionally substituted phenyl;
$R_9$ is hydrogen;

or an enantiomer thereof; or an enantiomeric mixture thereof; or a pharmaceutically acceptable salt thereof.

The compounds of the invention depending on the nature of the substituents possess one or more asymmetric centers. The resulting diastereoisomers, optical isomers, i.e., enantiomers, and geometric isomers, and mixtures thereof, are encompassed by the instant invention. Preferred are the compounds of the present invention wherein the substituent at the carbon atom adjacent to the amide group attains the R-configuration.

Particular embodiments of the invention are:

3-(Benzyl-{4-[(R)-2-cyclopentyl-1-(5-methoxy-thiazolo[5,4-b]pyridin-2-ylcarbamoyl)-ethyl]-benzenesulfonyl}-amino)-propionic acid;

3-[{4-[2-Cyclopentyl-1-([1,3,4]thiadiazol-2-ylcarbamoyl)-ethyl]-benzene-sulfonyl}-(2-methoxy-ethyl)-amino]-propionic acid;

3-(Benzofuran-2-ylmethyl-{4-[(R)-2-cyclopentyl-1-(5-methoxy-thiazolo[5,4-b]pyridin-2-ylcarbamoyl)-ethyl]-benzenesulfonyl}-amino)-propionic acid;

3-({4-[2-Cyclopentyl-1-(5-methoxy-thiazolo[5,4-b]pyridin-2-ylcarbamoyl)-ethyl]-benzenesulfonyl}-pyridin-2-ylmethyl-amino)-propionic acid;

3-({4-[2-Cyclopentyl-1-(5-methoxy-thiazolo[5,4-b]pyridin-2-ylcarbamoyl)-ethyl]-benzenesulfonyl}-oxazol-2-ylmethyl-amino)-propionic acid;

3-[{4-[2-Cyclopentyl-1-(5-methoxy-thiazolo[5,4-b]pyridin-2-ylcarbamoyl)-ethyl]-benzenesulfonyl}-(tetrahydro-furan-2-ylmethyl)-amino]-propionic acid;

3-({4-[2-Cyclopentyl-1-(5-methoxy-thiazolo[5,4-b]pyridin-2-ylcarbamoyl)-ethyl]-benzenesulfonyl}-thiophen-2-ylmethyl-amino)-propionic acid;

4-[((2-Carboxy-ethyl)-{4-[2-cyclopentyl-1-(5-methoxy-thiazolo[5,4-b]pyridin-2-ylcarbamoyl)-ethyl]-benzenesulfonyl}-amino)-methyl]-benzoic acid;

3-(Cyclohexylmethyl-{4-[2-cyclopentyl-1-(5-methoxy-thiazolo[5,4-b]pyridin-2-ylcarbamoyl)-ethyl]-benzenesulfonyl}-amino)-propionic acid;

3-[{4-[2-Cyclopentyl-1-(5-methoxy-thiazolo[5,4-b]pyridin-2-ylcarbamoyl)-ethyl]-benzenesulfonyl}-(5-methyl-furan-2-ylmethyl)-amino]-propionic acid;

3-[{4-[2-Cyclopentyl-1-(5-methoxy-thiazolo[5,4-b]pyridin-2-ylcarbamoyl)-ethyl]-benzenesulfonyl}-(2,5-dimethyl-furan-3-ylmethyl)-amino]-propionic acid;

[{4-[2-Cyclopentyl-1-(5-methoxy-thiazolo[5,4-b]pyridin-2-ylcarbamoyl)-ethyl]-benzenesulfonyl}-(5-methyl-furan-2-ylmethyl)-amino]-acetic acid;

3-({4-[2-Cyclopentyl-1-(5-methoxy-thiazolo[5,4-b]pyridin-2-ylcarbamoyl)-ethyl]-benzenesulfonyl}-isopropyl-amino)-propionic acid;

3-[{4-[2-Cyclopentyl-1-(5-methoxy-thiazolo[5,4-b]pyridin-2-ylcarbamoyl)-ethyl]-benzenesulfonyl}-(2-methoxy-ethyl)-amino]-propionic acid;

3-[{4-[2-Cyclopentyl-1-(5-methoxy-1,2-dihydro-thiazolo[5,4-b]pyridin-2-ylcarbamoyl)-ethyl]-benzenesulfonyl}-(1,5-dimethyl-1H-pyrazol-3-ylmethyl)-amino]-propionic acid;

3-[{4-[2-Cyclopentyl-1-(5-methoxy-thiazolo[5,4-b]pyridin-2-ylcarbamoyl)-ethyl]-benzenesulfonyl}-(5-methyl-isoxazol-3-ylmethyl)-amino]-propionic acid;

3-[{4-[2-Cyclopentyl-1-(5-methoxy-thiazolo[5,4-b]pyridin-2-ylcarbamoyl)-ethyl]-benzenesulfonyl}-(tetrahydro-pyran-4-ylmethyl)-amino]-propionic acid;

3-[{4-[2-Cyclopentyl-1-(5-methoxy-thiazolo[5,4-b]pyridin-2-ylcarbamoyl)-ethyl]-benzenesulfonyl}-(4-fluoro-benzyl)-amino]-propionic acid;

3-({4-[2-Cyclopentyl-1-(5-methoxy-thiazolo[5,4-b]pyridin-2-ylcarbamoyl)-ethyl]-benzenesulfonyl}-cyclopropylmethyl-amino)-propionic acid;

({4-[2-Cyclopentyl-1-(5-methoxy-thiazolo[5,4-b]pyridin-2-ylcarbamoyl)-ethyl]-benzenesulfonyl}-methyl-amino)-acetic acid;

3-({4-[2-Cyclopentyl-1-(5-methoxy-thiazolo[5,4-b]pyridin-2-ylcarbamoyl)-ethyl]-benzenesulfonyl}-methyl-amino)-propionic acid;

3-[{4-[2-Cyclopentyl-1-(5-methoxy-thiazolo[5,4-b]pyridin-2-ylcarbamoyl)-ethyl]-benzenesulfonyl}-(tetrahydro-pyran-4-yl)-amino]-propionic acid;

3-(Cyclohexyl-{4-[(S)-2-cyclopentyl-1-(5-methoxy-thiazolo[5,4-b]pyridin-2-ylcarbamoyl)-ethyl]-benzenesulfonyl}-amino)-propionic acid;

3-[{4-[(S)-2-Cyclopentyl-1-(5-methoxy-thiazolo[5,4-b]pyridin-2-ylcarbamoyl)-ethyl]-benzenesulfonyl}-(4-methoxy-phenyl)-amino]-propionic acid;

3-({4-[(S)-2-Cyclopentyl-1-(5-methoxy-thiazolo[5,4-b]pyridin-2-ylcarbamoyl)-ethyl]-benzenesulfonyl}-methyl-amino)-propionic acid;

3-[{4-[(S)-2-Cyclopentyl-1-(5-methoxy-thiazolo[5,4-b]pyridin-2-ylcarbamoyl)-ethyl]-benzenesulfonyl}-(2-isopropoxy-ethyl)-amino]-propionic acid;

3-({4-[(S)-2-Cyclopentyl-1-(5-methoxy-thiazolo[5,4-b]pyridin-2-ylcarbamoyl)-ethyl]-benzenesulfonyl}-thiazol-2-ylmethyl-amino)-propionic acid;

3-[{4-[2-Cyclopentyl-1-(5-fluoro-pyridin-2-ylcarbamoyl)-ethyl]-benzenesulfonyl}-(2-methoxy-ethyl)-amino]-propionic acid;

3-[{4-[(R)-2-Cyclopentyl-1-(pyrimidin-2-ylcarbamoyl)-ethyl]-benzenesulfonyl}-(2-methoxy-ethyl)-amino]-propionic acid;

3-[{4-[(R)-2-Cyclopentyl-1-(4-methyl-thiazol-2-ylcarbamoyl)-ethyl]-benzenesulfonyl}-2-methoxy-ethyl)-amino]-propionic acid;

3-[{4-[(R)-2-Cyclopentyl-1-(1-methyl-1H-pyrazol-3-ylcarbamoyl)-ethyl]-benzenesulfonyl}-(2-methoxy-ethyl)-amino]-propionic acid; and 3-[{4-[(R)-2-Cyclopentyl-1-(pyrimidin-4-ylcarbamoyl)-ethyl]-benzenesulfonyl}-(2-methoxy-ethyl)-amino]-propionic acid;

or an enantiomer thereof; or an enantiomeric mixture thereof; or a pharmaceutically acceptable salt thereof.

Compounds of formula (I) may be prepared using methods well known in the art, e.g., according to Method A or Method B as outlined herein below.

Method A:

Compounds of formula (I) may be obtained by coupling an amine of the formula

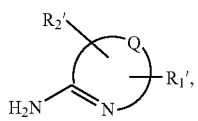

(II)

or acid addition salts thereof, wherein $R_1'$ and $R_2'$ represents $R_1$ and $R_2$, respectively, as defined herein above, or $R_1'$ and $R_2'$ are groups convertible to $R_1$ and $R_2$, respectively, with an activated derivative of a carboxylic acid of the formula

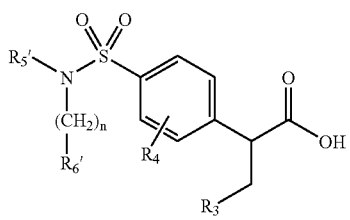

(III)

wherein $R_3$, $R_4$ and n have meanings as defined herein, and $R_5'$ and $R_6'$ represents $R_5$ and $R_6$, respectively, as defined herein above, or $R_5'$ and $R_6'$ are groups convertible to $R_5$ and $R_6$, respectively, to afford a compound of the formula

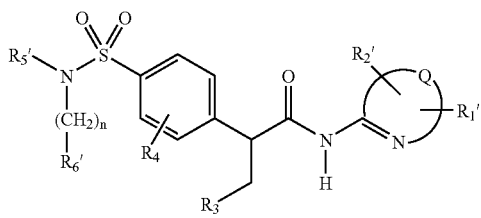

(I')

wherein $R_1'$, $R_2'$, $R_3$, $R_4$, n, $R_5'$ and $R_6'$ have meanings as defined for formulae (II) and (III).

In the coupling reaction cited herein above, an activated derivative of a carboxylic acid, e.g., those corresponding to carboxylic acids of formula (III), include acid chlorides, bromides and fluorides, mixed anhydrides, lower alkyl esters and activated esters thereof, and adducts formed with coupling agents, such as 1-ethyl-3-(3-dimethylaminopropyl)carbodiimide hydrochloride (EDCI), 1-hydroxy benzotriazole (HOBt), O-(1,2-dihydro-2-oxo-1-pyridyl)-N,N,N',N'-tetramethyluronium tetrafluoroborate, benzotriazole-1-yl-oxy-tris-pyrrolidino-phosphonium hexafluorophosphate (PyBOP) and the like. Mixed anhydrides are preferably such from pivalic acid, or lower alkyl hemiesters of carbonic acids, such as ethyl or isobutyl analogs. Activated esters include, for example, succinimido, phthalimido or 4-nitrophenyl esters. The reaction of an activated derivative of a carboxylic acid, e.g., those corresponding to carboxylic acids of formula (III), with an amine, e.g., those of formula (II), may be carried out in the presence of a base, such as pyridine, triethylamine (TEA), diisopropylethylamine (DIEA) or N-methylmorpholine (NMM) in an inert organic solvent, such as dichloromethane (DCM), N,N-dimethylformamide (DMF) or tetrahydrofuran (THF), or a mixture of solvents thereof. Carboxylic acids of formula (III) may be converted to their activated derivatives using methods described herein or according to methods generally known in the art, e.g., a carboxylic acid of formula (III) may be treated with a chlorinating agent, such as thionyl chloride or oxalyl chloride, to afford a corresponding acid chloride thereof, or by the treatment of a coupling agent such as EDCI or HOBt, or a mixture of coupling agents thereof.

Amines of formula (II) and carboxylic acids of formula (III) are known, or if they are novel they may be prepared using methods well known in the art or as described herein in the illustrative Examples, or modifications thereof. For example, compounds of formula (III) may be prepared by treating an ester of the formula

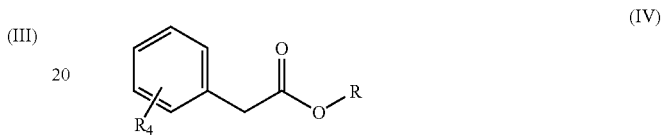

(IV)

wherein $R_4$ has a meaning as defined herein above, and R is lower alkyl, preferably, methyl or ethyl, with chlorosulfonic acid to afford a compound of the formula

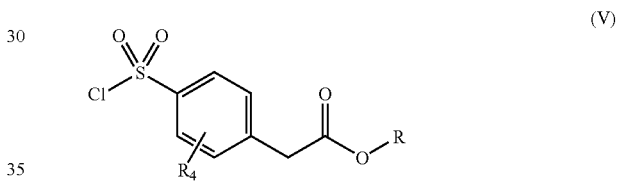

(V)

wherein $R_4$ and R have meanings as defined herein above, optionally in the presence of an intrinsic organic solvent. Preferably, the reaction is carried out without an intrinsic organic solvent.

A compound of formula (V) may then be treated with an amine of the formula

$$R_6'—(CH_2)_n—NH—R_5' \quad (VI),$$

or an acid addition salt thereof, wherein n, $R_5'$ and $R_6'$ have meanings as defined herein above, in the presence of a base, such as pyridine, TEA, DIEA or NMM, in an inert organic solvent, such as DCM, DMF or THF, or a mixture of solvents thereof, to afford a compound of the formula

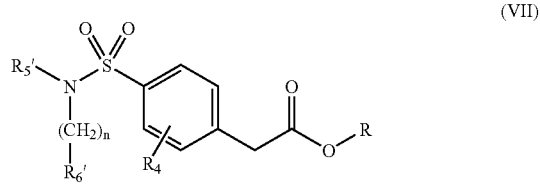

(VII)

wherein $R_4$, n, $R_5'$, $R_6'$ and R have meanings as defined herein above. Preferably, the reaction is conducted at a temperature ranging from about −4° C. to room temperature (RT), more preferably, the reaction temperature is about 0° C. Amines of formula (VI) are known, or if they are novel they may be prepared using methods well known in the art or as described herein in the illustrative Examples.

A resulting compound of formula (VII) may then be treated with a base, such as sodium hydride, lithium diisopropylamide (LDA) or lithium bis(trimethylsilyl)amide (LHMDS), preferably LDA, followed by addition of an alkylating agent of the formula $$R_3\text{—}(CH_2)\text{-Lg} \tag{VIII}$$

wherein $R_3$ has a meaning as defined herein above, and Lg represents a leaving group, such as chloride, bromide, iodide, mesylate, tosylate or triflate, preferably iodide ot triflate, to afford a compound of the formula

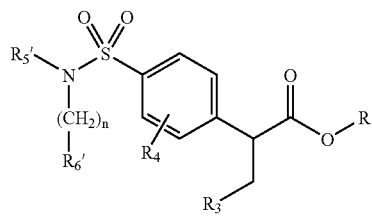

(IX)

wherein $R_3$, $R_4$, n, $R_5'$, $R_6'$ and R have meanings as defined herein above. The alkylation step is preferably conducted in a polar organic solvent, such as THF, DMF, N-methylpyrrolidone (NMP), 1,3-dimethyl-3,4,5,6-tetrahydro-2(1H)-pyridone (DMPU) or 1,3-dimethyl-3,4,5,6-tetrahydro-2(1H)-pyrimidinone (DMTP), or in a mixture of solvents thereof.

A resulting compound of formula (IX) may then be hydrolyzed, e.g., in the presence of an aqueous base such as sodium, lithium or potassium hydroxide and an organic solvent such as THF or lower alcohol, preferably, methanol or ethanol, to afford a carboxylic acid of formula (III) wherein $R_3$, $R_4$, n, $R_5'$ and $R_6'$ have meanings as defined herein above.

A carboxylic acid of formula (III) may then be coupled with an amine of formula (II), or an acid addition salt thereof, under reaction conditions as described herein above to afford a compound of formula (I') wherein $R_1'$, $R_2'$, $R_3$, $R_4$, n, $R_5'$ and $R_6'$ have meanings as defined herein above, e.g., via conversion of the acid to the corresponding acid chloride or in the presence of a coupling agent such as EDCI, HOBt or PyBOP, or a mixture of coupling agents thereof.

Alternatively, compounds of formula (I) may be prepared as outlined herein below.

Method B:

Compounds of formula (I) may be obtained by reacting a compound of the formula

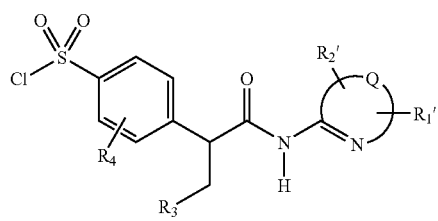

(X)

wherein $R_3$ and $R_4$ have meanings as defined herein above, and $R_1'$ and $R_2'$ represents $R_1$ and $R_2$, respectively, as defined herein above, or $R_1'$ and $R_2'$ are a groups convertible to $R_1$ and $R_2$, respectively, with an amine of the formula $$R_6'\text{—}(CH_2)_n\text{—}NH\text{—}R_5' \tag{VI},$$

or an acid addition salt thereof, wherein n, $R_5'$ and $R_6'$ have meanings as defined herein above, in the presence of a base, such as pyridine, TEA, DIEA or NMM, in an inert organic solvent, such as DCM, DMF or THF, or a mixture of solvents thereof, to afford a compound of the formula

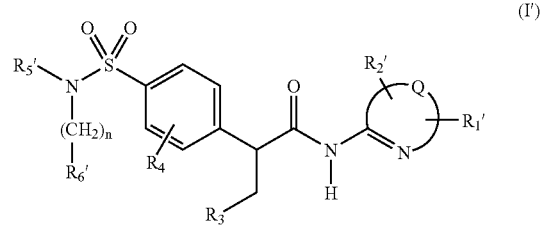

(I')

wherein $R_1'$, $R_2'$, $R_3$, $R_4$, n, $R_5'$ and $R_6'$ have meanings as defined herein above.

Compounds of formula (X) may be prepared, e.g., by treating a compound of the formula

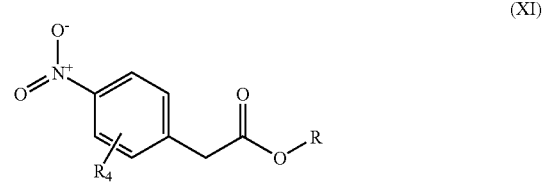

(XI)

wherein $R_4$ and R have meanings as defined herein above, with a base, such as sodium hydride, LDA or LHMDS, preferably LDA, followed by addition of an alkylating agent of the formula $$R_3\text{—}(CH_2)\text{-Lg} \tag{VIII}$$

wherein $R_3$ has a meaning as defined herein above, and Lg represents a leaving group, such as chloride, bromide, iodide, mesylate, tosylate or triflate, preferably iodide or triflate, to afford a compound of the formula

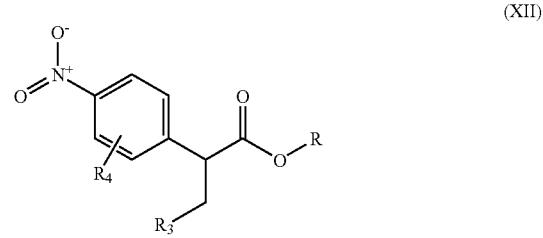

(XII)

wherein $R_3$, $R_4$ and R have meanings as defined herein above. The alkylation step is preferably conducted in a polar organic solvent, such as THF, DMF, NMP, DMPU or DMTP, or in a mixture of solvents thereof.

A resulting compound of formula (XII) may then be hydrolyzed, e.g., in the presence of an aqueous base, such as sodium, lithium or potassium hydroxide and an organic solvent such as THF or lower alcohol, preferably, methanol or ethanol, to afford a carboxylic acid of the formula

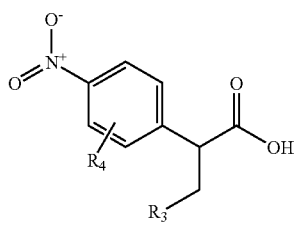

(XIII)

wherein $R_3$ and $R_4$ have meanings as defined herein above.

A carboxylic acid of formula (XIII) may then be coupled with an amine of formula (II) under reaction conditions as described herein above to afford a compound of the formula

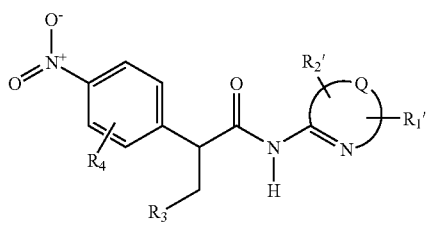

(XIV)

wherein $R_1'$, $R_2'$, $R_3$ and $R_4$ have meanings as defined herein above, e.g., via conversion of the carboxylic acid to the corresponding acid chloride, or in the presence of a coupling agent, such as EDCI, HOBt or PyBOP, or a mixture of coupling agents thereof.

A resulting compound of formula (XIV) may then be converted to a sulfonyl chloride derivative of formula (X) wherein $R_1'$, $R_2'$, $R_3$ and $R_4$ have meanings as defined herein above, by reduction of the nitro group to the amino group, e.g., using iron powder in the presence of a mixture of acetic acid and a lower alcohol, such as ethanol, followed by diazotization reaction and subsequent treatment with, e.g., sulfur dioxide in the presence of copper(II) chloride and acetic acid.

A resulting sulfonyl chloride derivative of formula (X) may then be treated with an amine of formula (VI), or an acid addition salt thereof, wherein n, $R_5'$ and $R_6'$ have meanings as defined herein above, under reaction conditions described herein above to afford a compound of formula (I') wherein $R_1'$, $R_2'$, $R_3$, $R_4$, n, $R_5'$ and $R_6'$ have meanings as defined herein above.

The processes described herein above may be conducted under inert atmosphere, preferably under nitrogen atmosphere.

In starting compounds and intermediates which are converted to the compounds of the present invention in a manner described herein, functional groups present, such as amino, thiol, carboxyl and hydroxyl groups, are optionally protected by conventional protecting groups that are common in preparative organic chemistry. Protected amino, thiol, carboxyl and hydroxyl groups are those that can be converted under mild conditions into free amino thiol, carboxyl and hydroxyl groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxyl group, amino group, etc.), the structure and stability of the molecule of which the substituent is a part and the reaction conditions.

Well-known protecting groups that meet these conditions and their introduction and removal are described, e.g., in McOmie, "Protective Groups in Organic Chemistry", Plenum Press, London, N.Y. (1973); and Greene and Wuts, "Protective Groups in Organic Synthesis", John Wiley and Sons, Inc., NY (1999).

The above-mentioned reactions are carried out according to standard methods, in the presence or absence of diluent, preferably, such as are inert to the reagents and are solvents thereof, of catalysts, condensing or said other agents, respectively and/or inert atmospheres, at low temperatures, RT or elevated temperatures, preferably at or near the boiling point of the solvents used, and at atmospheric or super-atmospheric pressure. The preferred solvents, catalysts and reaction conditions are set forth in the appended illustrative Examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

The invention also relates to any novel starting materials, intermediates and processes for their manufacture.

Depending on the choice of starting materials and methods, the new compounds may be in the form of one of the possible isomers or mixtures thereof, for example, as substantially pure geometric (cis or trans) isomers, diastereomers, optical isomers (enantiomers, antipodes), racemates or mixtures thereof. The aforesaid possible isomers or mixtures thereof are within the purview of this invention.

Any resulting mixtures of isomers can be separated on the basis of the physicochemical differences of the constituents, into the pure geometric or optical isomers, diastereomers, racemates, for example, by chromatography and/or fractional crystallization.

Any resulting racemates of final products or intermediate, e.g., acids of formulae (III) and (XIII), can be resolved into the optically pure isomers by known methods, e.g., by separation of the diastereomeric salts thereof, obtainable with an optically active acid or base and liberating the optically active acidic or basic compound, respectively, e.g., acids of formulae (III) and (XIII) can be resolved using optically active 1-phenylethylamine. Similarly, the compounds of the instant invention having a basic moiety may be resolved into their optical isomers, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Alternatively, optically pure isomers of compounds of the present invention may be obtained by employing chiral reagents. For example, an optical isomer, preferably the R isomer, of compounds of formula (X) may be prepared employing chiral auxiliaries, e.g., the Evans auxiliary, as illustrated herein in the Examples.

Finally, compounds of the invention are either obtained in the free form, or in a salt form thereof, preferably, in a pharmaceutically acceptable salt form thereof, or as a prodrug derivative thereof.

Compounds of the instant invention which contain acidic groups may be converted into salts with pharmaceutically acceptable bases. Such salts include alkali metal salts, like sodium, lithium and potassium salts; alkaline earth metal salts, like calcium and magnesium salts; ammonium salts with organic bases, e.g., trimethylamine salts, diethylamine salts, tris(hydroxymethyl)methylamine salts, dicyclohexylamine salts and N-methyl-D-glucamine salts; salts with amino acids like arginine, lysine and the like. Salts may be formed using conventional methods, advantageously in the presence of an ethereal or alcoholic solvent, such as a lower alkanol. From the solutions of the latter, the salts may be precipitated with ethers, e.g., diethyl ether. Resulting salts may be converted into the free compounds by treatment with acids. These or other salts can also be used for purification of the compounds obtained.

Compounds of the invention, in general, may be converted into acid addition salts, especially pharmaceutically acceptable salts. These are formed, e.g., with inorganic acids, such as mineral acids, e.g., sulfuric acid, phosphoric or hydrohalic acid, or with organic carboxylic acids, such as $(C_{1-4})$alkanecarboxylic acids which, e.g., are unsubstituted or substituted by halogen, e.g., acetic acid, such as saturated or unsaturated dicarboxylic acids, e.g., oxalic, succinic, maleic or fumaric acid, such as hydroxycarboxylic acids, e.g., glycolic, lactic, malic, tartaric or citric acid, such as amino acids, e.g., aspartic or glutamic acid, or with organic sulfonic acids, such as $(C_{1-4})$alkylsulfonic acids, e.g., methanesulfonic acid; or arylsulfonic acids which are unsubstituted or substituted (for example by halogen). Preferred are salts formed with hydrochloric acid, maleic acid and methanesulfonic acid.

Prodrug derivatives of any compound of the invention are derivatives of said compounds which following administration release the parent compound in vivo via some chemical or physiological process, e.g., a prodrug on being brought to the physiological pH or through enzyme action is converted to the parent compound. Exemplary prodrug derivatives are, e.g., esters of free carboxylic acids and S-acyl and O-acyl derivatives of thiols, alcohols or phenols, wherein acyl has a meaning as defined herein. Preferred are pharmaceutically acceptable ester derivatives convertible by solvolysis under physiological conditions to the parent carboxylic acid. Such ester derivatives include, but are not limited to, lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and others conventionally used in the art, e.g., a compound of formula (IA) wherein $R_9$ is optionally substituted lower alkyl as described herein above, lower alkenyl, cycloalkyl, aryl or aralkyl, is easily convertible to a compound of formula (IA) wherein $R_9$ is hydrogen.

In view of the close relationship between the free compounds, the prodrug derivatives and the compounds in the form of their salts, whenever a compound is referred to in this context, a prodrug derivative and a corresponding salt is also intended, provided such is possible or appropriate under the circumstances.

The compounds, including their salts, can also be obtained in the form of their hydrates, or include other solvents used for their crystallization.

As described herein above, the compounds of the present invention may be employed for the treatment of conditions mediated by glucokinase activity. Such compounds may thus be employed therapeutically for the treatment of impaired glucose tolerance, type 2 diabetes and obesity.

The present invention further provides pharmaceutical compositions comprising a therapeutically effective amount of a pharmacologically active compound of the instant invention, alone or in combination with one or more pharmaceutically acceptable carriers.

The pharmaceutical compositions according to the invention are those suitable for enteral, such as oral or rectal; transdermal and parenteral administration to mammals, including man, for the treatment of conditions mediated by glucokinase activity. Such conditions include impaired glucose tolerance, type 2 diabetes and obesity.

Thus, the pharmacologically active compounds of the invention may be employed in the manufacture of pharmaceutical compositions comprising an effective amount thereof in conjunction or admixture with excipients or carriers suitable for either enteral or parenteral application. Preferred are tablets and gelatin capsules comprising the active ingredient together with:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and or polyvinylpyrrolidone; if desired
d) disintegrants, e.g., starches, agar, alginic acid or its sodium salt, or effervescent mixtures; and/or
e) absorbants, colorants, flavors and sweeteners.

Injectable compositions are preferably aqueous isotonic solutions or suspensions, and suppositories are advantageously prepared from fatty emulsions or suspensions.

Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Accordingly, the present invention provides pharmaceutical compositions as described above for the treatment of conditions mediated by glucokinase activity, preferably, impaired glucose tolerance, type 2 diabetes and obesity.

The pharmaceutical compositions may contain a therapeutically effective amount of a compound of the invention as defined above, either alone or in a combination with another therapeutic agent, e.g., each at an effective therapeutic dose as reported in the art. Such therapeutic agents include:

a) anti-diabetic agents, such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; thiazolidone derivatives such as glitazones, e.g., pioglitazone and rosiglitazone; protein tyrosine phosphatase-1B (PTP-1B) inhibitors such as PTP-112; GSK3 (glycogen synthase kinase-3) inhibitors such as SB-517955, SB-4195052, SB-216763, N,N-57-05441 and N,N-57-05445; RXR ligands such as GW-0791 and AGN-194204; sodium-dependent glucose co-transporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; modulators of PPARs (peroxisome proliferator-activated receptors), e.g., non-glitazone type PPARγ agonists such as N-(2-benzoylphenyl)-L-tyrosine analogues, e.g. GI-262570, and JTT501; DPPIV (dipeptidyl peptidase IV) inhibitors such as LAF237, MK-0431, saxagliptin and GSK23A; SCD-1 (stearoyl-CoA desaturase-1) inhibitors; DGAT1 and DGAT2 (diacylglycerol acyltransferase 1 and 2) inhibitors; ACC2 (acetyl CoA carboxylase 2) inhibitors; and breakers of AGE (advanced glycation end products);

b) anti-dyslipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; HDL increasing compounds such as cholesterol ester transfer protein (CETP) inhibitors, e.g., JTT705; Apo-A1 analogs and mimetics; squalene synthase inhibitors; FXR (farnesoid X receptor) and LXR (liver X receptor) ligands; cholestyramine; fibrates; nicotinic acid; and aspirin;

c) anti-obesity agents such as phentermine, leptin, bromocriptine, dexamphetamine, amphetamine, fenfluramine, dexfenfluramine, sibutramine, orlistat, dexfenfluramine, mazindol, phentermine, phendimetrazine, diethylpropion, fluoxetine, bupropion, topiramate, diethylpropion, benzphetamine, phenylpropanolamine, ecopipam, ephedrine, and pseudoephedrine; cholesterol absorption modulators such as ZETIA® and KT6-971; and cannabinoid receptor antagonists such as rimonabant; and d) anti-hypertensive agents, e.g., loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na-K-ATPase membrane pump such as digoxin; neutralendopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as ditekiren, zankiren, terlakiren, aliskiren, RO 66-1132 and RO-66-1168; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists such as eplerenone; and aldosterone synthase inhibitors such as anastrazole and fadrazole.

Other specific anti-diabetic compounds are described by Patel Mona in *Expert Opin Investig Drugs*, 2003, 12(4), 623-633, in the FIGS. 1 to 7, which are herein incorporated by reference. A compound of the present invention may be administered either simultaneously, before or after the other active ingredient, either separately by the same or different route of administration or together in the same pharmaceutical formulation.

The structure of the therapeutic agents identified by code numbers, generic or trade names may be taken from the actual edition of the standard compendium "The Merck Index" or from databases, e.g., Patents International (e.g. IMS World Publications). The corresponding content thereof is hereby incorporated by reference.

Accordingly, the present invention provides pharmaceutical compositions comprising a therapeutically effective amount of a compound of the invention in combination with a therapeutically effective amount of another therapeutic agent, preferably selected from anti-diabetics, hypolipidemic agents, anti-obesity agents or anti-hypertensive agents, most preferably from antidiabetics or hypolipidemic agents as described above.

The present invention further relates to pharmaceutical compositions as described above for use as a medicament.

The present invention further relates to use of pharmaceutical compositions or combinations as described above for the preparation of a medicament for the treatment of conditions mediated by glucokinase activity, preferably, impaired glucose tolerance, type 2 diabetes and obesity.

Thus, the present invention also relates to a compound of formula (I) for use as a medicament; to the use of a compound of formula (I) for the preparation of a pharmaceutical composition for the prevention and/or treatment of conditions mediated by glucokinase activity, and to a pharmaceutical composition for use in conditions mediated by glucokinase activity comprising a compound of formula (I), or a pharmaceutically acceptable salt thereof, in association with a pharmaceutically acceptable diluent or carrier therefore.

The present invention further provides a method for the prevention and/or treatment of conditions mediated by glucokinase activity, which comprises administering a therapeutically effective amount of a compound of the present invention.

A unit dosage for a mammal of about 50-70 kg may contain between about 1 mg and 1000 mg, advantageously between about 5-500 mg of the active ingredient. The therapeutically effective dosage of active compound is dependent on the species of warm-blooded animal (mammal), the body weight, age and individual condition, on the form of administration, and on the compound involved.

In accordance with the foregoing the present invention also provides a therapeutic combination, e.g., a kit, kit of parts, e.g., for use in any method as defined herein, comprising a compound of formula (I), or a pharmaceutically acceptable salt thereof, to be used concomitantly or in sequence with at least one pharmaceutical composition comprising at least another therapeutic agent, preferably selected from anti-diabetic agents, hypolipidemic agents, anti-obesity agents and anti-hypertensive agents, or a pharmaceutically acceptable salt thereof. The kit may comprise instructions for its administration.

Similarly, the present invention provides a kit of parts comprising: (i) a pharmaceutical composition of the invention; and (ii) a pharmaceutical composition comprising a compound selected from an anti-diabetic, a hypolipidemic agent, an anti-obesity agent and an anti-hypertensive agent, or a pharmaceutically acceptable salt thereof, in the form of two separate units of the components (i) to (ii).

Likewise, the present invention provides a method as defined above comprising co-administration, e.g., concomitantly or in sequence, of a therapeutically effective amount of a compound of formula (I), or a pharmaceutically acceptable salt thereof, and a second drug substance, said second drug substance being an anti-diabetic, a hypolipidemic agent, an anti-obesity agent or an anti-hypertensive agent, e.g., as indicated above.

Preferably, a compound of the invention is administered to a mammal in need thereof.

Preferably, a compound of the invention is used for the treatment of a disease which responds to modulation of the glucokinase activity.

Preferably, the condition associated with glucokinase activity is selected from impaired glucose tolerance, type 2 diabetes and obesity.

Finally, the present invention provides a method or use which comprises administering a compound of formula (I) in combination with a therapeutically effective amount of an anti-diabetic agent, a hypolipidemic agent, an anti-obesity agent or an anti-hypertensive agent.

Ultimately, the present invention provides a method or use which comprises administering a compound of formula (I) in the form of a pharmaceutical composition as described herein.

As used throughout the specification and in the claims, the term "treatment" embraces all the different forms or modes of treatment as known to those of the pertinent art and in particular includes preventive, curative, delay of progression and palliative treatment.

The above-cited properties are demonstrable in vitro and in vivo tests using advantageously mammals, e.g., mice, rats, dogs, monkeys or isolated organs, tissues and preparations thereof. Said compounds can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-2}$ molar and $10^{-9}$ molar concentrations. A therapeutically effective amount in vivo may range depending on the route of administration, between about 0.1 mg/kg and 1000 mg/kg, preferably between about 1 mg/kg and 100 mg/kg.

The activity of compounds according to the invention may be assessed by the following methods or methods well-described in the art:

For example, the glucokinase activation in vitro may be determined by measuring the activation of recombinant GST-GK by a compound of the present invention in the absence or the presence of GKRP, a 68,000 Da protein inhibitor of GK. In these assays, formation of glucose-6-phosphate is coupled directly to the formation of thio-NADH. GST-GK catalyzes the reaction of glucose and Mg-ATP to produce glucose-6-phosphate and ADP. Glucose-6-phosphate dehydrogenase (G6PDH) reduces thionicotinamide (thio-NAD) to thio-NADH. The assay measures the formation of thio-NADH at 405 nM.

The basic GK assay components are as follows: 25 mM HEPES (pH 7.1), 25 mM KCl, 2.5 mM $MgCl_2$, 1 mM ATP (Sigma A-5394), 1 mM DTT, 1 mM thio-NAD (Sigma T-7375), 80 units/mL G6PDH (Sigma G-5885), 10 mM glucose and 110 nM GST-GK. For assessing reversal of GK inhibition by GKRP, 20 μM Fructose-6-phosphate (F-6-P) and 370 nM recombinant GKRP are added to these assay components. Fructose-1-phosphate (F-1-P) at 1 μM is used as a control in the GK/GKRP assay. F-1-P reverses inhibition of GST-GK by GKRP.

The assay is done in standard, 96-well, round-bottom plates (Corning) and the total assay volume is 25 μL. Test compounds are serially diluted into 100% DMSO and 0.5 μL of diluted compound in 100% DMSO is added to the assay plate. Assay reagents (24.5 μL) are added using a Zymark robotic platform. Buffer, containing HEPES, $MgCl_2$, KCl, thio-NAD, G6PDH, glucose and GST-GK, are added (5 μL) using the Zymark 8-channel hand pipet. For the GK/GKRP assay, GKRP and F-6-P are also included. The reaction is then initiated by adding 19.5 μL of buffer containing HEPES, $MgCl_2$, KCl, DTT and ATP using the Zymark Reagent Addition Station/Reagent Addition Module. The plates are read kinetically over 10 min at 25° C. using a SpectraMax Plus microplate spectrophotometer (Molecular Devices, Sunnyvale, Calif.) to monitor the increase in optical density at 405 nm. The GK activity in wells containing test compounds is compared with activity in DMSO control wells. The concentration of compound that produces a 50% increase in the activity of GK is calculated and expressed as $EC_{50}$. A majority of the compounds described in the Examples had an $EC_{50}$ value less than or equal to 200 μM and preferably less than 50 μM. Most preferable are compounds with $EC_{50}$ less than 2 μM which exhibited at least a 2-fold increase in % GK activation versus control.

The glucokinase activation in rat hepatocytes may be determined as follows:

Hepatocytes are isolated by collagenase perfusion of the livers of overnight-fasted male Harlen Sprague-Dawley rats (Charles River Laboratories, Raleigh, N.C.) as previously described (see Berry et al., *J. Cell Biol.*, Vol. 43, pp. 506-520 (1969)). The cells are washed three times each with 100 mL of glucose-free Dulbecco's Modified Eagle medium (DMEM, Gibco BRL) containing 5% fetal bovine serum (FBS) and then suspended in glucose-free DMEM/5% FBS. Cells are plated in collagen coated 24-well plates (Becton Dickinson) at a density of $3 \times 10^5$ cells/well in 1 mL of William's Medium E (Sigma) supplemented with 5% FBS, and incubated at 37° C. in 5% $CO_2$/95% air. After cell attachment (~4 h), the medium is replaced with serum-free DMEM containing 5 mM glucose and 10 nM dexamethasone (Sigma), and cells are cultured further for 16-20 h prior to use.

The rate of glucose phosphorylation is determined by the release of $^3H_2O$ from [2-$^3H$]glucose. The medium from the cultured hepatocytes is removed, and the cells are pre-incubated in 150 μL of fresh serum-free DMEM containing 5 mM glucose and compound (1, 10 and 30 μM) or DMSO for 3 h at 37° C. The final concentration of DMSO is 0.2%. The medium is then removed and 150 μL of a fresh mixture of DMEM/5 mM glucose containing compound or DMSO, and 1 μCi of [2-$^3H$]glucose (NEN) is added. As a positive control for stimulation of glucose phosphorylation, cells are pre-incubated in serum-free DMEM/5 mM glucose medium containing DMSO for 3 h and then are incubated for 1 h in labeled glucose medium containing 0.5 mM fructose/DMSO (precursor of F-1-P, AnalaR® from BDH). All conditions are tested in quadruplicate where one well per plate received 200 μL of the appropriate medium plus labeled glucose (instead of 150 μL) of which 50 μL is immediately removed and placed in a 1.2 mL microfuge tube (Costar) containing 10 μL of 1 N HCl. This sample is used as a 0-minute time point for determining background $^3H_2O$ release (exchange values). Following the addition of the labeled glucose media, hepatocytes are incubated at 37° C. on a slow moving rocker for 1 h.

On termination of the incubation, 50 μL of the culture medium is collected into microfuge tubes containing 10 μL of 1 N HCl, and determination of $^3H_2O$. The tubes are left uncapped and each is placed inside a 20 mL glass scintillation vial (Wheaton) containing 1.5 mL of deionized water. The vials are capped tightly and incubated at 37° C. in a dry incubator for 2 days ($3H_2O$ from the reaction mixture will equilibrate with the water in the vial). A standard curve is generated using [$^3H$]$H_2O$ (NEN) to correct for exchange. 50

µL aliquots of serial dilutions of the labeled water are added to 10 µL of 1 N HCl and exchange is performed as described for the samples (typically, approximately 90% exchange is observed). The microfuge tubes are then removed from the vials carefully to minimize the removal of any water from the vial and 18 mL of scintillation cocktail (Ready Safe, Beckman Coulter) is then added to each vial. The $^3$H-label recovered from [2-$^3$H]glucose in the water is determined using a Beckman Model LS500 scintillation counter and the counts (minus the 0-time point) are corrected for recovery of $^3$H$_2$O. The amount of glucose de-tritiated in nanomoles/h per $10^6$ cells is calculated, and the results are expressed as percent increase over the DMSO control.

The glucokinase activation in vivo may be determined as follows:

Male C57BL mice (Jackson Lab, Bar Harbor, Me.) are housed 2 per cage in a reversed light cycle room (light on from 8:00 p.m. to 8:00 a.m.) and given access to food and water ad libitum. To induce DIO, the mice are given a high fat diet (D12492 with 60% caloric intake from fat, Research Diets, New Brunswick, N.J.) from 4 weeks of age and maintained on the diet before being used. The DIO mice are used at 25 weeks of age. On the day of the study, animals are fasted at 7:30 a.m. Body weight measurement and basal blood sample collection are conducted at 10:00 a.m. Plasma glucose values are then determined. Animals are assigned into five groups (n=7/group) with the means of plasma glucose matched among the groups. At 10:30 a.m. animals are dosed with vehicle (water) or compound in vehicle with a dose volume of 5 ml/kg. The test compound is given at 3, 10, 30, or 100 mg/kg. One hour after vehicle or compound dosing, a blood sample (at 0 min) is taken followed by an oral glucose tolerance test (OGTT) at 1 g/kg (20% glucose in water) and a dose volume of 5 ml/kg. Blood samples are collected at 30, 60 and 120 min following the glucose administration. The animals are refed after the OGTT. Blood samples are taken via tail bleeding. Plasma glucose concentrations are determined using a glucose meter (Ascensia Elite, Bayer Corp., Mishawaka, Ind.). Blood samples are collected in tubes (Microvette CB300, Aktiengesellschaft & Co., Numbrecht, Germany) which contain EDTA (ethylene diaminetetraacetic acid) to prevent blood clotting. After blood sample collection, the tubes are kept on ice before being centrifuged. Plasma portion of the blood samples is obtained by centrifugation at 10,000×g for 10 min at 4° C. and then stored at –80° C. Plasma insulin levels are determined by Luminex assay using Mouse Endocrine Lincoplex kit (Linco Research, Inc., St. Charles, Mo.). Data are reported as means ±SEM. Statistical analysis is performed using a one-way or two-way analysis of variance (ANOVA) followed by a Tukey post-hoc test to compare the difference among the groups. Statistical significance is accepted at the level of p<0.05.

Illustrative of the invention, the compound of Example 1 demonstrates an $EC_{50}$ of about 271 nM in the in vitro assay measuring the activation of recombinant GST-GK. Oral (po) dosing of a compound of Example 1 provides statistically significant glucose lowering with reductions in glucose of 38-53% at different timepoints during the oral glucose tolerance test.

The following Examples are intended to illustrate the invention and are not to be construed as being limitations thereon. If not mentioned otherwise, all evaporations are performed under reduced pressure, preferably between about 50 mmHg and 100 mmHg. The structure of final products, intermediates and starting materials is confirmed by standard analytical methods, e.g., microanalysis, melting point (m.p.) and spectroscopic characteristics, e.g., MS, IR and NMR. Abbreviations used are those conventional in the art.

EXAMPLE 1

3-(Benzyl-{4-[(R)-2-cyclopentyl-1-(5-methoxy-thiazolo[5,4-b]pyridin-2-ylcarbamoyl)-ethyl]-benzenesulfonyl}-amino)-propionic acid

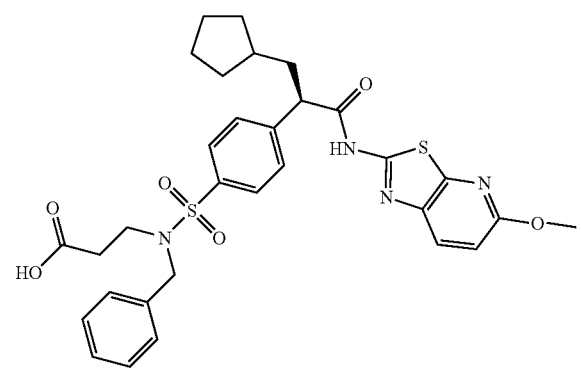

A. (4R,5S)-4-Methyl-5-phenyl-3-phenylacetyl-oxazolidin-2-one (4R,5S)-4-Methyl-5-phenyl-oxazolidin-2-one (25.21 g, 142.269 mmol) is dissolved in anhydrous THF (100 mL) and cooled to –78° C. n-Butyl lithium (2.5 M in hexanes, 62.60 mL, 156.5 mmol) is added dropwise over 10 min. The reaction is stirred at –78° C. for 10 min. Phenylacetyl chloride (20.73 mL, 156.5 mmol) is dissolved in anhydrous THF (50 mL) and added dropwise over 10 min. The reaction is stirred at –78° C. for 2 h. The reaction is poured onto brine (300 mL) and extracted with ethyl acetate (2×250 mL). Extracts are combined, dried over anhydrous sodium sulfate, filtered, and concentrated to a yellow oil which solidified upon standing. The rude product is purified by column chromatography over silica eluting with 5→45% ethyl acetate in hexanes to afford (4R,5S)-4-methyl-5-phenyl-3-phenylacetyl-oxazolidin-2-one as a white solid: $^1$H NMR (400 MHz, DMSO-D$_6$) δ 0.8 (d, J=6.6 Hz, 3 H) 4.2 (m, 2 H) 4.8 (m, 1 H) 5.9 (d, J=7.3 Hz, 1 H) 7.2 (m, 3 H) 7.3 (m, 5 H) 7.4 (m, 2 H); LC/MS 296.2 (M+1), 294.1 (M–1).

B. Trifluoromethanesulfonic acid cyclopentylmethyl ester

Trifluoromethanesulfonic anhydride (6.72 mL, 39.94 mmol) is dissolved in DCM (40 mL) and cooled to –40° C. To this is added dropwise cyclopentanemethanol (4.00 g, 39.94 mmol) dissolved in DCM (10 mL) and anhydrous pyridine (3.23 mL, 39.94 mmol). The reaction is stirred at –40° C. for 45 min. The reaction is diluted with hexanes (30 mL) and run through a plug of silica using hexanes (300 mL) as the eluent. Concentration without heating gives trifluoromethanesulfonic acid cyclopentylmethyl ester as a clear, colorless oil that is used immediately.

C. (4R,5S)-3-((R)-3-Cyclopentyl-2-phenyl-propionyl)-4-methyl-5-phenyl-oxazolidin-2-one The title A compound, (4R,5S)-4-methyl-5-phenyl-3-phenylacetyl-oxazolidin-2-one (5.00 g, 16.93 mmol) is dissolved in anhydrous THF (50 mL) and cooled to −78° C. Lithium bis(trimethylsilyl)amide (1 M in THF, 16.93 mL, 16.93 mmol) is added dropwise over 10 min. To this is added a solution of the title B compound, trifluoromethanesulfonic acid cyclopentylmethyl ester (3.93 g, 16.93 mmol) in anhydrous THF (15 mL). The reaction is stirred at −78° C. for 10 min, then the cold bath is removed. The reaction is allowed to stir and warm to RT. After one hour, the reaction is concentrated to remove the solvent, resulting in a yellow oil. This dissolved in ethyl acetate (300 mL) and washed with water (2×200 mL). The organic solution is dried over anhydrous sodium sulfate, filtered, and concentrated to a yellow oil. This is recrystallized from hexanes to afford (4R,5S)-3-((R)-3-cyclopentyl-2-phenyl-propionyl)-4-methyl-5-phenyl-oxazolidin-2-one as a white solid: $^1$H NMR (400 MHz, DMSO-D$_6$) δ0.8 (d, J=6.6 Hz, 3 H) 1.1 (d, J=16.2 Hz, 2 H) 1.4 (m, 2 H) 1.5 (d, J=5.8 Hz, 2 H) 1.6 (s, 2 H) 1.8 (d, J=7.1 Hz, 2 H) 2.0 (d, J=13.4 Hz, 1 H) 4.8 (s, 1 H) 5.1 (s, 1 H) 5.7 (d, J=7.1 Hz, 1 H) 7.3 (s, 1 H) 7.4 (m, 9 H); LC/MS 378.2 (M+1).

D. (R)-3-Cyclopentyl-2-phenyl-propionic acid

Lithium hydroxide monohydrate (1.28 g, 30.6 mmol) is suspended in THF (50 mL) and cooled to 0° C. Hydrogen peroxide (50 wt % in water, 2.81 mL, 91.79 mmol) is added dropwise. Reaction is stirred at 0° C. for 15 min and the title C compound, (4R,5S)-3-((R)-3-cyclopentyl-2-phenyl-propionyl)-4-methyl-5-phenyl-oxazolidin-2-one (3.85 g, 10.2 mmol) is added in five separate portions, allowing portions to dissolve completely between additions. The reaction is allowed to stir and warm to RT overnight. The reaction is then concentrated to a sticky white solid. This is dissolved in ethyl acetate (25 mL)/1 N HCl (25 mL). The organic solution is dried over anhydrous sodium sulfate, filtered, and concentrated to afford the crude product as a yellow oil. The crude product is chromatographed over silica eluting with 5→65% ethyl acetate in hexanes to afford (R)-3-cyclopentyl-2-phenyl -propionic acid as a white solid: $^1$H NMR (400 MHz, CDCl3) δ 1.1 (m, J=11.6, 7.8, 7.8, 3.9 Hz, 2 H) 1.5 (m, 2 H) 1.6 (m, 2 H) 1.7; LC/MS 217.2 (M−1).

E. 5-Methoxy-thiazolo[5,4-b]pyridin-2-ylamine

Potassium thiocyanate (156 g, 1600 mmol) is dissolved in acetic acid (1400 mL) and cooled to 0° C. 6-Bromo-pyridin-3-ylamine (50 g, 400 mmol) is dissolved in acetic acid (100 mL) and added dropwise over 10 min. Bromine (25 mL, 480 mmol) is dissolved in acetic acid (100 mL) and added dropwise over 10 min. The reaction is allowed to stir and warm to RT overnight. Acetic acid is removed via concentration. The resulting residue is poured into water (1 L) and adjusted to pH=7 with 1 N sodium hydroxide solution. This is extracted with ethyl acetate. Extracts are combined, washed with brine, and concentrated to a brown sludge. Recrystallization from methanol affords 5-methoxy-thiazolo[5,4-b]pyridin-2-ylamine as a brown solid: $^1$H NMR (400 MHz, DMSO-D$_6$) δ 3.8 (s, 3 H) 6.7 (d, J=8.8 Hz, 1 H) 7.4 (s, 2 H) 7.6 (d, J=8.6 Hz, 1 H); LC/MS 182.3 (M+1), 180.4 (M−1).

F. (R)-3-Cyclopentyl-N-(5-methoxy-thiazolo[5,4-b]pyridin-2-yl)-2-phenyl-propionamide The title D compound, (R)-3-cyclopentyl-2-phenyl-propionic acid (1.66 g, 7.605 mmol) is dissolved in thionyl chloride (15 mL) and heated at 50° C. for 1.5 h. The reaction is then cooled to RT and concentrated to afford a yellow oil. This is dissolved in anhydrous THF (10 mL) and added dropwise to a solution of the title E compound, 5-methoxy-thiazolo[5,4-b]pyridin-2-ylamine (1.38 g, 7.605 mmol) in anhydrous pyridine (10 mL) at 0° C. The reaction is allowed to stir and warm to RT. After 2 h, the reaction is concentrated to remove the THF and most of the pyridine. The resulting brown oil is dissolved in ethyl acetate (250 mL)/1 N HCl (250 mL) and extracted further with ethyl acetate. The combined organic layer is dried over anhydrous sodium sulfate, filtered, and concentrated to afford the crude product as a brown oil. This is chromatographed over silica eluting with 5→60% ethyl acetate in hexanes to afford (R)-3-cyclopentyl-N-(5-methoxy-thiazolo[5,4-b]pyridin-2-yl)-2-phenyl-propionamide as a yellow foam: $^1$H NMR (400 MHz, DMSO-D$_6$) δ1.1 (m, 2 H) 1.4 (dd, J=7.2, 4.7 Hz, 2 H) 1.6 (m, 3 H) 1.7 (m, 3 H) 2.1 (m, 1 H) 3.9 (m, 4 H) 6.9 (d, J=8.8 Hz, 1 H) 7.3 (m, 1 H) 7.4 (m, 4 H) 8.0 (d, J=8.6 Hz, 1 H) 12.5 (s, 1 H); LC/MS 382.1 (M+1), 380.2 (M−1).

G. 4-[(R)-2-Cyclopentyl-1-(5-methoxy-thiazolo[5,4-b]pyridin-2-ylcarbamoyl)-ethyl]benzenesulfonyl chloride Chlorosulfonic acid (20 mL) is cooled to 0° C. To this is added a solution of the title F compound, (R)-3-cyclopentyl-N-(5-methoxy-thiazolo[5,4-b]pyridin-2-yl)-2-phenyl-propionamide (2.53 g, 6.632 mmol) in DCM (10 mL). The reaction is allowed to stir and warm to RT over 2.5 h. The reaction is then added dropwise to crushed ice (400 mL) and extracted with DCM (3×100 mL). Extracts are combined, dried over anhydrous sodium sulfate, filtered, and concentrated to give 4-[(R)-2-cyclopentyl-1-(5-methoxy-thiazolo[5,4-b]pyridin-2-ylcarbamoyl)-ethyl]benzenesulfonyl chloride as a yellow foam. Product is isolated as a 80:20 mixture of the desired para product and undesired meta product: $^1$H NMR (400 MHz, DMSO-D$_6$) δ1.1 (s, 2 H) 1.4 (d, J=4.8 Hz, 1 H) 1.4 (s, 1 H) 1.5 (m, 3 H) 1.7 (s, 2 H) 1.8 (d, J=13.4 Hz, 1 H) 2.1 (m, 1 H) 3.9 (s, 3 H) 4.0 (s, 1 H) 6.9 (d, J=8.6 Hz, 1 H) 7.3 (m, 2 H) 7.6 (d, J=8.1 Hz, 2 H) 8.0 (d, J=8.6 Hz, 1 H) 14.3 (s, 2 H); LC/MS 480.2 (M+1), 478.3 (M−1).

H. 3-benzyl amino propionic acid tert butyl ester

Benzylamine (1 g, 9.33 mmol) is dissolved in ethanol (25 mL), to which tert -butyl acrylate (1.20 g, 9.33 mmol) is added. The reaction is stirred at RT overnight and then concentrated to a crude yellow oil. This material is purified via flash chromatography (2→20% methanol in ethyl acetate) to afford 3-benzyl amino propionic acid tert butyl ester as a clear oil: $^1$H NMR (400 MHz, CDCl$_3$) δ 1.44 (s, 9H) 1.64 (s, 1H) 2.44 (m, 2H) 2.85 (m, 2H) 3.79 (m, 2H) 7.24 (m, 1H) 7.31 (m, 4H).

I. 3-(Benzyl-{4-[(R)-2-cyclopentyl-1-(5-methoxy-thiazolo[5,4-b]pyridin-2-ylcarbamoyl)-ethyl]-benzenesulfonyl}-amino)-propionic acid tert-butyl ester The title G compound, 4-[(R)-2-cyclopentyl-1-(5-methoxythiazole[5,-4-b]pyridin-2-ylcarbonyl)ethyl]benzene sulfonyl chloride (0.301 g, 0.627 mmol) is dissolved in DCM (10 mL), to which the title H compound, 3 benzyl amino propionic acid tert butyl ester (0.148 g, 0.627 mmol) and DIEA (0.162 g, 1.254 mmol) in DCM are added. The reaction mixture is stirred at RT for one hour and then concentrated. The residue is partitioned between 1 N HCl/ethyl acetate. The organic layer is dried over magnesium sulfate, filtered and concentrated to afford a crude yellow oil. This material is purified via flash chromatography (10% ethyl acetate in hexanes→ethyl acetate) to afford a pale yellow foam. This material is separated from the meta isomer (derived from compound G) by chiral HPLC (20% ethanol in hexanes) to afford 3-(benzyl-{4-[(R)-2-cyclopentyl-1-(5-methoxy-thiazolo[5,4-b]pyridin-2-ylcarbamoyl)-ethyl]-benzenesulfonyl}-amino)-propionic acid tert-butyl ester as a white foam: $^1$H NMR (400 MHz, CDCl3) δ 1.16 (m, 2H) 1.35 (s, 9H) 1.51 (m, 2H) 1.64 (m, 3H) 1.76 (m, 2H) 1.96 (m, 1H) 2.26 (m, 1H) 2.36 (m, 2H) 3.40 (m, 2H) 3.69 (m, 1H) 4.00 (s, 3H) 4.36 (s, 2H) 6.81 (m, 1H) 7.28 (m, 5H) 7.49 (m, 2H) 7.82 (m, 3H) 8.65 (s, 1H); LC/MS 679.6 (M+1), 677.6 (M−1).

J. 3-(Benzyl-{4-[(R)-2-cyclopentyl-1-(5-methoxy-thiazolo[5,4-b]pyridin-2-ylcarbamoyl)-ethyl]-benzenesulfonyl}-amino)-propionic acid The title I compound, 3-(benzyl-{4-[(R)-2-cyclopentyl-1-(5-methoxy-thiazolo[5,4-b]pyridin-2-ylcarbamoyl)-ethyl]-benzenesulfonyl}-amino)-propionic acid tert-butyl ester (0.064 g, 0.0942 mmol) is dissolved in methanol (5 mL), to which a solution of sodium hydroxide (0.004 g, 0.0942 mmol) in water (2 mL) is added. The reaction mixture is stirred at RT overnight. The reaction mixture is then concentrated and the residue is partitioned between 1 M HCl/ethyl acetate. The organic layer is dried over magnesium sulfate, filtered and concentrated to afford 3-(benzyl-{4-[(R)-2-cyclopentyl-1-(5-methoxy-thiazolo[5,4-b]pyridin-2-ylcarbamoyl)-ethyl]-benzenesulfonyl}-amino)-propionic acid as a white foam: $^1$H NMR (400 MHz-CDCl$_3$) δ 1.17 (m, 2H) 1.50 (m, 2H) 1.66 (m, 4H) 1.78 (m, 1H) 2.28 (m, 1H) 2.43 (m, 2H) 3.23 (m, 1H) 3.50 (m, 1H) 3.85 (m, 2H) 4.00 (s, 3H) 4.37 (m, 1H) 4.77 (m, 1H) 6.79 (m, 1H) 7.36 (m, 5H) 7.52 (m, 2H) 7.67 (m, 1H) 7.95 (m, 2H); LC/MS 623.3 (M+1), 621.4 (M−1). EC$_{50}$ in primary enzyme assay 0.27 µM

EXAMPLE 2

3-[{4-[2-Cyclopentyl-1-([1,3,4]thiadiazol-2-ylcarbamoyl)-ethyl]-benzene-sulfonyl}-(2-methoxy-ethyl)-amino]-propionic acid

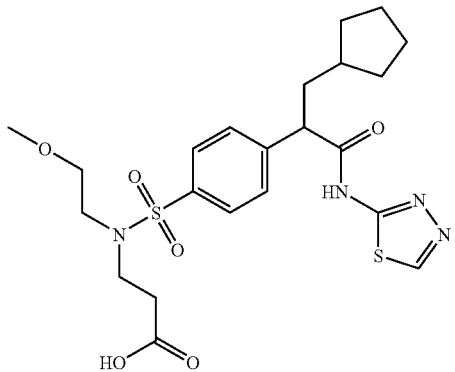

A. 3-Cyclopentyl-2-phenylpropionic acid methyl ester

To a 500 mL round bottom flask containing 250 mL of 9:1 THF/DMPU at −78° C. is added 17 mL DIEA followed by rapid addition of 49 mL of 2.5 M n-BuLi/hexanes. After 10 min at −78° C., a solution of ethyl phenylacetate (17.0 g, 113 mmol) in 50 mL of 9:1 THF/DMPU is added dropwise over 15-20 min. A yellow solution results, and the reaction mixture is stirred at −78° C. for 30-45 min. A solution of 26.7 g (115 mmol) of freshly prepared cyclopentyl triflate (title B compound in Example 1) in 25 mL 9:1 THF/DMPU is added dropwise over 10-15 min. The mixture is then stirred over 2-3 h to ambient temperature. The reaction is quenched into 300 mL of 1 N HCl and extracted 3 times with methyl-t-butylether (MTBE). The combined extracts are washed with saturated NaCl and dried over anhydrous magnesium sulfate. Filtration and evaporation afford crude product as a yellow oil. Flash chromatography over silica gel eluting with 4:1 hexane/MTBE affords 3-cyclopentyl-2-phenylpropionic acid methyl ester as a light yellow oil: $^1$H NMR (400 MHz, CDCl$_3$) δ 1.1 (m, 2H), 1.3 (m, 1H), 1.50 (m, 2H), 1.6 (m, 2H), 1.7 (m, 2H), 2.1(dt, J=13.4, 7.7 Hz, 1H), 3.60 (m, 1H), 3.64 (s, 3H), 7.3 (m, 5H); LC/MS 233 (M+1).

B. 3-Cyclopentyl-2-phenylpropionic acid

To title A compound, 3-cyclopentyl-2-phenylpropionic methyl ester (13.0 g, 56 mmol) in 100 mL of methanol is added a solution of 5.6 g (140 mmol) of NaOH in 8 mL of water. The reaction mixture is stirred at ambient temperature overnight. The methanol is evaporated and the residue is dissolved in 200 mL of water and extracted with ethyl ether. The aqueous phase is separated and adjusted to pH 2-3 with 1 N HCl and extracted with MTBE twice. The combined extracts are washed with saturated sodium chloride and dried over anhydrous magnesium sulfate. The material is evaporated to a yellow oil that crystallizes to provide 3-cyclopentyl-2-phenylpropionic acid as an off-white solid: $^1$H NMR (400 MHz, CDCl$_3$) δ 1.7 (m, 2H), 2.1 (m, 2H), 2.2 (m, 3H), 2.4(m, 3H), 2.4 (m, 1H), 4.2 (t, J=7.7 Hz, 1H), 7.9 (m, 5H); LC/MS 236 (M+NH$_4^+$).

C. 3-Cyclopentyl-2-phenylpropionyl chloride

To the title B compound, 3-cyclopentyl-2-phenylpropionic acid (3.1 g, 14.2 mmol) is added 10 mL of thionyl chloride and one drop of DMF. The reaction mixture is stirred at ambient temperature for 2 h. The excess thionyl chloride is evaporated and the residue is twice treated with toluene and evaporated to yield 3-cyclopentyl-2-phenylpropionyl chloride as an orange-yellow oil which is selected as such without further purification.

D. 3-Cyclopentyl-2-phenyl-N-[1,3,4]thiadiazol-2-yl-propionamide

To 2-amino-1,3,4-thiadiazole (220 mg, 21 mmol), 0.4 mL DIEA and 7 mL of DCM is added a solution of the title C compound, 3-cyclopentyl-2-phenylpropionyl chloride (500 mg, 21 mmol) in 2 mL of DCM. The mixture is stirred at ambient temperature for 2-3 h, the mixture is evaporated, and the residue is treated with 10 mL 1 N HCl and extracted twice with ethyl acetate. The combined extracts are washed with brine, saturated sodium bicarbonate solution, and brine and dried over anhydrous magnesium sulfate. Filtration and evaporation afford 3-cyclopentyl-2-phenyl-N-[1,3,4]thiadiazol-2-yl-propionamide as an orange foam: $^1$H NMR (400 MHz, DMSO-d$_6$) δ 11 (m, 2H), 1.4 (m, 2H), 1.5 (m, 3H), 1.7(m, 3H), 2.1 (ddd, J=13.3, 7.8, 7.7 Hz, 1H), 4.0 (dd, J=8.1, 7.1 Hz, 1H), 7.2 (s, 1H), 7.3 (m, 4H), 9.1 (s, 1H), 12.8 (s, 1H); LC/MS 302 (M+1), 300 (M−1).

E. 4-[2-Cyclopentyl-1-(1,3,4)thiadiazol-2-ylcarbamoyl)-ethyl]benzenesulfonyl chloride To 5 mL of chlorosulfonic acid in an ice bath at 0° C. is added dropwise title D compound, 3-cyclopentyl-2-phenyl-N-[1,3,4]thiadiazol-2-yl-propionamide (200 mg, 0.66 mmol) in 2 mL of DCM. The reaction is stirred at ambient temperature for 2-3 h until an orange color persists. The reaction is carefully quenched into solid ice, extracted with ethyl acetate and dried over anhydrous magnesium sulfate. The reaction is filtered and reduce to a greenish resin which is used as such in the next step.

F. 3-[{4-[2-Cyclopentyl-1-([1,3,4]thiadiazol-2-ylcarbamoyl)-ethyl]-benzenesulfonyl}-(2-methoxy-ethyl)-amino]-propionic acid tert-butyl ester To t-butyl N-(2-methoxyethyl)propionate (110 mg, 0.058 mmol) and 0.20 mL of DIEA in 8 mL of DCM is added title E compound, 4-[2-cyclopentyl-1-(1,3,4)thiadiazol -2-ylcarbamoyl)-ethyl]benzenesulfonyl chloride (230 mg, 0.57 mmol). The mixture is stirred at ambient temperature for one hour and DCM is evaporated. The residue is treated with 10 mL of 1 N HCl and extracted with ethyl acetate. The organic extract is washed successively with brine, saturated sodium bicarbonate, and brine. The organic layer is dried over anhydrous magnesium sulfate, filtered and evaporated to a brown oil. This is purified using a Biotage 40M column eluted with 1:1-hexane:ethyl acetate to provide 3-[{4-[2-cyclopentyl-1-([1,3,4]thiadiazol-2-ylcarbamoyl)-ethyl]-benzenesulfonyl}-(2-methoxy-ethyl)-amino]-propionic acid tert-butyl ester as a light orange foam: $^1$H NMR (400 MHz, DMSO-d$_6$) δ 1.1 (m, 1H), 1.4 m, 5H), 1.5 (m, 1H), 1.7 (m, 1H), 2.4 (t, 7.3 Hz, 1H), 3.3 (t, J=5.7 Hz, 1H), 3.3 (m, 5H), 7.61 (d, J=8.3 Hz, 2H), 7.79 (d, J=8.3 Hz, 2H), 9.16 (s, 1H), 12.89 (s, 1H); LC/MS 567 (M+1), 565 (M−1).

G. 3-[{4-[2-Cyclopentyl-1-([1,3,4]thiadiazol-2-ylcarbamoyl)-ethyl]-benzenesulfonyl}-(2-methoxy-ethyl)-amino]-propionic acid To 75 mg (0.133 mmol) of title F compound, 3-[{4-[2-cyclopentyl-1-([1,3,4]thiadiazol-2-ylcarbamoyl)-ethyl]-benzenesulfonyl}-(2-methoxy-ethyl)-amino]-propionic acid tert-butyl ester is added 2 mL of DCM and 0.5 mL of trifluoroacetic acid. The reaction mixture is stirred at ambient temperature for one hour. The reaction is evaporated to a brownish resin and subsequently dissolved in ether and decanted from some insoluble material. The organic layer is evaporated to a light orange resin which is dissolved in 2 mL methanol in a 50 mL round bottom flask. Aqueous potassium hydroxide (0.265 mL of 0.5094 M potassium hydroxide solution) is added and stirred for 30 min. The methanol is evaporated, 8 mL of water added, and the mixture lyophilized to afford 3-[{4-[2-cyclopentyl-1-([1,3,4]thiadiazol-2-ylcarbamoyl)-ethyl]-benzenesulfonyl}-(2-methoxy-ethyl)-amino]-propionic acid as a light orange-brown solid: $^1$H NMR (400 MHz, DMSO-d$_6$) δ 1.1 (m, 1H), 1.4 (m, 1H), 1.6 (m, 2H), 1.7 (ddd, J=13.1, 6.9, 6.7 Hz, 2H), 2.1 (ddd, J=11.2, 8.2, 7.8, 2H), 3.2 (s, 2H), 3.2 (m, 3H), 3.7 (t, J=7.5 Hz, 1H), 7.56 (d, J=8.3, 2H), 7.63 (d, J=8.3 Hz, 2H), 8.58 (s, 1H); L/MS 511 (M+1), 509 (M−1). EC$_{50}$ in primary enzyme assay 50 µM.

EXAMPLE 3

3-(Benzofuran-2-ylmethyl-{4-[(R)-2-cyclopentyl-1-(5-methoxy-thiazolo[5,4-b]pyridin-2-ylcarbamoyl)-ethyl]-benzenesulfonyl}-amino)-propionic acid

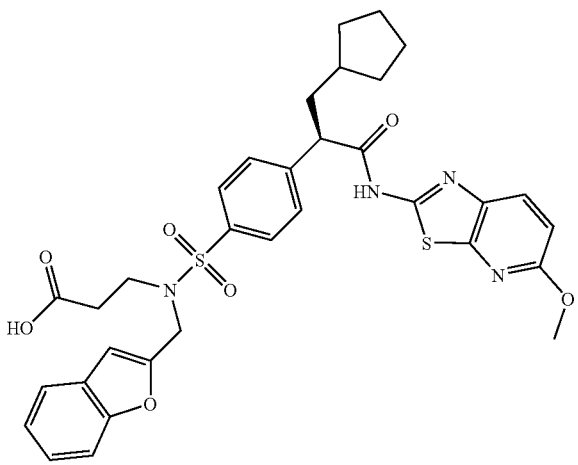

A. 3-Cyclopentyl-2-(4-nitro-phenyl)-propionic acid ethyl ester

To a 1 L round bottom flask containing 250 mL of 9:1 THF/DMPU at −78° C. are added under nitrogen 11 mL (78.6 mmol) anhydrous DIEA followed by rapid addition of 32 mL of 2.5 M n-BuLi in hexanes. After 10 min at −78° C. a solution of 15.4 g (74 mmol) of p-nitrophenylacetic acid, ethyl ester in 100 mL of 9:1 THF/DMPU is added dropwise over 30 min. A deep purple solution results, and the reaction mixture is stirred at −78° C. for 30 min and then cyclopentyl methyl iodide (17.6 g, 78 mmol) in 50 mL of 9:1 THF/DMPU is added. The reaction is stirred while warming slowly to RT overnight. The mixture is poured into 1 L of 1 N HCl and extracted twice with MTBE. The combined MTBE extracts are washed with brine, dried over anhydrous magnesium sulfate, filtered and reduced to an orange oil. Flash chromatography over silica eluting with 4:1 hexane/MTBE affords 3-cyclopentyl-2-(4-nitro-phenyl)-propionic acid ethyl ester as an orange oil: $^1$H NMR (400 MHz, CDCl$_3$) δ 1.0-1.1 (m, 2H), 1.2 (t, 3H, J=7.2), 1.4-1.8 (m, 5H), 1.8-1.9 (m, 2H), 2.1-2.25 (m, 2H), 3.74 (t, 1H, J=7.8), 4.1 (m, 2H), 7.51 (d, 2H, J=8.8), 8.19 (d, 2H, J=8.8); LC/MS 290 (M−1).

B. 3-Cyclopentyl-2-(4-nitro-phenyl)-propionic acid

The title A compound, 3-cyclopentyl-2-(4-nitro-phenyl)-propionic acid ethyl ester (3.6 g, 12.3 mmol) is dissolved in 25 mL of methanol and aqueous NaOH (0.70 g, 17.5 mmol in 4 mL of water) is added and the mixture is stirred at RT overnight. The methanol is removed under reduced pressure and the residue is diluted with 100 mL of water and extracted with ether. The aqueous layer is then acidified with 1N HCl and then extracted with ethyl acetate. The combined ethyl acetate layers are dried over anhydrous magnesium sulfate, filtered and reduced under vacuum to a crude orange oil. The crude oil is triturated with 100 mL of hexane/10-15 mL of ether to produce 3-cyclopentyl-2-(4-nitro-phenyl)-propionic acid as a solid: $^1$H NMR (400 MHz, CDCl$_3$) δ 1.0-1.1 (m, 2H), 1.4-1.8 (m, 5H), 1.8-1.9 (m, 2H), 2.1-2.25 (m, 2H), 3.74 (t, 1H, J=7.8), 7.51 (d, 2H, J=8.8), 8.19 (d, 2H, J=8.8); LC/MS 218 (—CO$_2$, M−1), 279 (M+NH$_4^+$).

C. 3-Cyclopentyl-N-(5-methoxy-thiazolo[5,4-b]pyridin-2-yl)-2-(4-nitro-phenyl)-propionamide The title B compound, 3-cyclopentyl-2-(4-nitro-phenyl)-propionic acid (7.5 g, 28.5 mmol) is dissolved in 25 mL of thionyl chloride and a drop of DMF and the mixture stirred at RT for 5-6 h. The excess of thionyl chloride is removed under reduced pressure. The residue is then taken up in DCM and added dropwise to a solution of the title E compound in Example 1, 5-methoxy-thiazolo[5,4-b]pyridin-2-ylamine (5.2 g, 28.5 mmol) in 25 mL of pyridine. The reaction mixture is stirred for 5 h before being evaporated to remove the pyridine. The residue is partitioned between ethyl acetate and brine, extracted with ethyl acetate. The combined organic layers are washed with saturated sodium bicarbonate, brine, dried over anhydrous magnesium sulfate, filtered and then reduced to an orange-brown solid. This is then vacuum dried to afford 3-cyclopentyl-N-(5-methoxy-thiazolo[5,4-b]pyridin-2-yl)-2-(4-nitro-phenyl)-propionamide as a foam: $^1$H NMR (400 MHz, CDCl$_3$) δ 1.0-1.1 (m, 2H), 1.4-1.8 (m, 5H), 1.8-1.9 (m, 2H), 2.1-2.25 (m, 2H), 3.6 (t, 1H, J=7.8), 4.01 (s, 3H), 6.8 (d, 1H, J=8.8), 7.4 (d, 2H, J=8.6), 7.8 (d, 1H, J=8.8 Hz), 8.19 (d, 2H, J=8.6 Hz), 9.3 (s, 1H); LC/MS 427 (M+1).

D. 2-(4-Amino-phenyl)-3-cyclopentyl-N-(5-methoxy-thiazolo[5,4-b]pyridin-2-yl)-propionamide The title C compound, 3-cyclopentyl-N-(5-methoxy-thiazolo[5,4-b]pyridin-2-yl)-2-(4-nitro-phenyl)-propionamide (12 g, 28.2 mmol) is diluted with 160 mL of ethanol and 150 mL acetic acid. 8 g of iron powder (325 mesh, 0.14 mol) is added and the mixture heated to reflux. Once reflux begins the mixture is stirred vigorously and then heating is discontinued and the mixture is allowed to cool slowly. The solvents are removed and the residue is treated with 250 mL of water. Saturated sodium bicarbonate is added carefully to bring the mixture to a pH of 8-9. The mixture is extracted with ethyl acetate, washed with brine, dried and evaporated to give an orange solid which is triturated from hexane. The resulting solid is collected by filtration to afford 2-(4-amino-phenyl)-3-cyclopentyl-N-(5-methoxy-thiazolo[5,4-b]pyridin-2-yl)-propionamide: $^1$H NMR (400 MHz, CDCl$_3$) δ 1.0-1.1 (m, 2H), 1.4-1.8 (m, 5H), 1.8-1.9 (m, 2H), 2.1-2.25 (m, 2H), 3.6 (t, 1H, J=7.8), 3.98 (s, 3H), 6.7 (d, 1H, J=8.8), 6.8 (d, 2H, J=8.6), 7.2 (d, 2H, J=8.6), 7.8 (d, 1H, J=8.8); LC/MS 397 (M+1).

E. 4-[2-Cyclopentyl-1-(5-methoxy-thiazolo[5,4-b]pyridin-2-ylcarbamoyl)-ethyl]-benzenesulfonyl chloride The title D compound, 2-(4-amino-phenyl)-3-cyclopentyl-N-(5-methoxy-thiazolo[5,4-b]pyridin-2-yl)-propionamide (2.0 g, 5.1 mmol) is dissolved in 50 mL of acetic acid and 20 mL of concentrated HCl and the mixture is cooled to 0° C. A solution of 0.35 g (5.1 mmol) of NaNO$_2$ in 5 mL of water is added dropwise and the mixture is stirred for 30 min. The resulting yellow solution is then added to 180 mL of the Green Solution (prepared by bubbling 74 g of sulfur dioxide gas into 740 mL of glacial acetic acid followed by addition of 30 g of CuCl$_2$ in 35-40 mL water. The resulting mixture is filtered through filter paper to obtain a clear green solution) and the mixture is stirred at RT overnight (the initial black-green solution transforms to a light green solution after 24 h). The resulting mixture is poured onto 500 g of ice and the precipitated solids are collected by filtration, washed with water and then dissolved in ethyl acetate, washed with brine, dried over anhydrous magnesium sulfate, filtered and evaporated to afford a yellow foam. This material is flash chromatographed over silica eluting with 7:3 hexane/ethyl acetate to afford 4-[2-cyclopentyl-1-(5-methoxy-thiazolo[5,4-b]pyridin-2-ylcarbamoyl)-ethyl]-benzenesulfonyl chloride as a stable yellow foam: $^1$H NMR (400 MHz, CDCl$_3$) δ 1.0-1.1 (m, 2H), 1.4-1.8 (m, 5H), 1.8-1.9 (m, 2H), 2.1-2.25 (m, 2H), 3.7 (t, 1H, J=7.8), 4.01 (s, 3H), 6.8 (d, 1H, J=8.8), 7.5 (d, 2H, J=8.6), 7.8 (d, 1H, J=8.8), 8.19 (d, 2H, J=8.6), 9.3 (s, 1H); LC/MS 480 (M+1).

F. 2-Benzofuran-2-ylmethyl-isoindole-1,3-dione

Benzofuran-2-yl-methanol (450 mg, 3.037 mmol) is dissolved in THF (100 mL). Triphenylphosphine (956 mg, 3.645 mmol) and phthalamide (536 mg, 3.645 mmol) are added in one portion. The reaction is cooled to 0° C. Di-tert-butyl azodicarboxylate (839 mg, 3.645 mmol) is dissolved in THF (10 mL) and added dropwise. The reaction is allowed to warm to RT overnight and the solvent is removed by rotary evaporation. The resulting orange oil is triturated in methanol and filtered to afford 2-benzofuran-2-ylmethyl-isoindole-1,3-dione as a white solid: $^1$H NMR (400 MHz, DMSO-D$_6$) δ 4.9 (s, 2 H) 6.87 (s, 1 H) 7.2 (m, 2 H) 7.5 (m, 2 H) 7.9 (m, 4 H); LC/MS 278.1 (M+1).

G. Benzofuran-2-yl-methylamine

The title F compound, 2-benzofuran-2-ylmethyl-isoindole-1,3-dione (1 g, 3.606 mmol) is slurried in methanol (150 mL). Hydrazine hydrate (271 mg, 5.410 mmol) is added and the reaction heated at 50° C. for 2.5 h. A solution is formed during heating. The reaction is then cooled to RT and concentrated to afford a white foam. This is dissolved in 1 N sodium hydroxide solution and ethyl acetate. The organic layer is separated, dried over anhydrous sodium sulfate, filtered, and concentrated to afford benzofuran-2-yl-methylamine as a yellow solid: $^1$H NMR (400 MHz, CDCl3) δ 4.0 (s, 2 H) 6.5 (s, 1 H) 7.2 (m, 2 H) 7.4 (d, J=7.8 Hz, 1 H) 7.5 (d, J=7.6 Hz, 1 H); LC/MS 131.1 (M+1).

H. 3-[(Benzofuran-2-ylmethyl)-amino]-propionic acid benzyl ester

The title G compound, benzofuran-2-yl-methylamine (290 mg, 1.970 mmol) is dissolved in ethanol (50 mL). To this is added benzyl acrylate (352 mg, 2.167 mmol). The reaction is stirred at RT overnight, then concentrated to afford the crude product as a yellow oil. This is chromatographed using 20% ethyl acetate in hexanes→ethyl acetate to afford the purified product as a pale yellow oil: $^1$H NMR (400 MHz, CDCl3) δ 2.6 (t, J=6.4 Hz, 2 H) 3.0 (t, J=6.4 Hz, 2 H) 3.9 (s, 2 H) 5.1 (s, 2 H) 6.5 (d, J=1.0 Hz, 1 H) 7.2 (m, 2 H) 7.3 (m, 5 H) 7.4 (m, 1 H) 7.5 (dd, J=7.5, 1.1 Hz, 1 H); LC/MS 310.1 (M+1).

I. 3-(Benzofuran-2-ylmethyl-{4-[(R)-2-cyclopentyl-1-(5-methoxy-thiazolo[5,4-b]pyridin-2-ylcarbamoyl)-ethyl]-benzenesulfonyl}-amino)-propionic acid benzyl ester The title E compound, 4-[2-cyclopentyl-1-(5-methoxy-thiazolo[5,4-b]pyridin-2-ylcarbamoyl)-ethyl]-benzenesulfonyl chloride (1.208 mg, 2.517 mmol) is added in one portion to a solution of the title H compound, 3-[(benzofuran-2-ylmethyl)-amino]-propionic acid benzyl ester (856 mg, 2.768 mmol) and TEA (388 μL, 2.768 mmol) in DCM, and stirred at RT overnight. The reaction is concentrated to afford a green oil. Purification via column chromatography eluting with 10% ethyl acetate in hexanes→ethyl acetate afforded the racemic product as a tan solid (750 mg). This is separated by chiral prep HPLC to afford the desired steroisomer of 3-(benzofuran-2-ylmethyl-{4-[(R)-2-cyclopentyl-1-(5-methoxy-thiazolo[5,4-b]pyridin-2-ylcarbamoyl)-ethyl]-benzenesulfonyl}-amino)-propionic acid benzyl ester as a white solid: $^1$H NMR (400 MHz, DMSO-D6) δ 1.1 (m, 2 H) 1.4 (dd, J=7.2, 4.7 Hz, 2 H) 1.6 (dt, J=14.9, 7.5 Hz, 3 H) 1.7 (ddd, J=13.4, 7.1, 6.8 Hz, 3 H) 2.1 (ddd, J=13.1, 7.8, 7.6 Hz, 1 H) 2.6 (m, 2 H) 3.4 (m, 2 H) 3.9 (s, 3 H) 4.0 (t, J=7.6 Hz, 1 H) 4.6 (d, J=11.4 Hz, 2 H) 5.0 (s, 2 H) 6.7 (s, 1 H) 6.9 (m, 1 H) 7.1 (m, 2 H) 7.3 (m, 6H) 7.5 (m, 1 H) 7.6 (d, J=8.3 Hz, 2 H) 7.8 (d, J=8.3 Hz, 2H) 8.0 (d, J=8.8 Hz, 1 H) 12.7 (s, 1 H); LC/MS 753.6 (M+1), 751.7 (M−1).

J. 3-(Benzofuran-2-ylmethyl-{4-[(R)-2-cyclopentyl-1-(5-methoxy-thiazolo[5,4-b]pyridin-2-ylcarbamoyl)-ethyl]-benzenesulfonyl}-amino)-propionic acid The title I compound, 3-(benzofuran-2-ylmethyl-{4-[(R)-2-cyclopentyl-1-(5-methoxy-thiazolo[5,4-b]pyridin-2-ylcarbamoyl)-ethyl]-benzenesulfonyl}-amino)-propionic acid benzyl ester (280 mg, 0.372 mmol) is dissolved in THF. To this is added a solution of sodium hydroxide (22 mg, 0.558 mmol) in water. The reaction is stirred at RT overnight. LC/MS indicates ~80% reaction completion and, therefore, more sodium hydroxide (10 mg, 0.250 mmol) is added. After 2 h of stirring at RT, the reaction is acidified to pH 1 with concentrated hydrochloric acid, then concentrated to remove solvent. The residue is diluted with ethyl acetate and water. The organic layer is separated, dried over anhydrous sodium sulfate, filtered, and concentrated to afford the crude product as a yellow foam. Purification by preparative HPLC affords 3-(benzofuran-2-ylmethyl-{4-[(R)-2-cyclopentyl-1-(5-methoxy-thiazolo[5,4-b]pyridin-2-ylcarbamoyl)-ethyl]-benzenesulfonyl}-amino)-propionic acid as a white solid: $^1$H NMR (400 MHz, DMSO-D$_6$) δ 1.4 (m, 2 H) 1.6 (m, 3 H) 1.7 (m, 3 H) 2.1 (m, 1H) 3.35 (m, 1 H) 3.9 (s, 3 H) 4.0 (m, 1 H) 4.6 (s, 2 H) 6.7 (s, 1 H) 6.9 (d, J=8.8 Hz, 1 H) 7.1 (m, 2 H) 7.3 (m, 2 H) 7.5 (dt, J=4.3, 2.1 Hz, 1 H) 7.6 (d, J=8.3 Hz, 2 H) 7.8 (d, J=8.6 Hz, 2 H) 8.0 (d, J=8.8 Hz, 1 H) 12.7 (s, 1 H); LC/MS 663.5 (M+1), 661.5 (M−1). EC$_{50}$ in primary enzyme assay 0.22 μM.

EXAMPLE 4

The following examples may be prepared by a skilled artisan using the appropriated methods described herein above.

4-1 3-({4-[2-Cyclopentyl-1-(5-methoxy-thiazolo[5,4-b]pyridin-2-ylcarbamoyl)-ethyl]-benzenesulfonyl}-pyridin-2-ylmethyl-amino)-propionic acid: MS MH+ 624; 1H NMR (400 MHz, DMSO-D6) δ ppm 1.04 1.2 (m, 2 H) 1.40-1.48 (m, 2 H) 1.52-1.62 (m, 3 H) 1.68-1.75 (m, 2 H) 1.78-1.85 (dd, J=13.5, 7.2 Hz, 1 H) 2.10-2.20 (m, 1H) 2.4 (m, 2 H) 3.4 (t, J=7.5 Hz, 2 H) 3.91 (s, 3H) 4.1 (t, J=7.5 Hz, 1 H) 4.5 (s, 2 H) 6.9 (d, J=8.8 Hz, 1 H) 7.2 (dd, J=7.3, 5.1 Hz, 1 H) 7.3 (d, J=7.6 Hz, 1 H) 7.59 (d, J=8.3 Hz, 2H) 7.7 (m, 1 H) 7.8 (d, J=8.3 Hz, 2 H) 8.0 (d, J=8.8 Hz, 1 H) 8.4 (d, J=4.3 Hz, 1 H) 12.7 (s, 1 H).

4-2 3-({4-[2-Cyclopentyl-1-(5-methoxy-thiazolo[5,4-b]pyridin-2-ylcarbamoyl)-ethyl]-benzenesulfonyl}-oxazol-2-ylmethyl-amino)-propionic acid: MS MH+ 614; 1H NMR (400 MHz, DMSO-d6) δ ppm 1.12 (br. s., 2 H) 1.43 (dd, J=6.95, 4.93 Hz, 2 H) 1.59 (d, J=7.33 Hz, 1 H) 1.56 (d, J=3.79 Hz, 1 H) 1.72 (d, J=12.88 Hz, 2 H) 1.69 (br. s., 1 H) 2.01-2.12 (m, 3 H) 3.27 (br. s., 2 H) 3.30 (d, J=7.58 Hz, 3 H) 3.85 (s, 3 H) 4.54 (s, 2 H) 6.68 (d, J=8.84 Hz, 1 H) 7.02 (s, 1 H) 7.53 (d, J=8.59 Hz, 2 H) 7.59-7.65 (m, 2 H) 7.89 (s, 1 H).

4-3 3-[{4-[2-Cyclopentyl-1-(5-methoxy-thiazolo[5,4-b]pyridin-2-ylcarbamoyl)-ethyl]-benzenesulfonyl}-(tetrahydro-furan-2-ylmethyl)-amino]-propionic acid: MS MH+ 617, 1H NMR (400 MHz, DMSO-D6) δ ppm 1.02-1.18 (m, 2 H) 1.35-1.43 (m, 2 H) 1.48-1.60 (m, 4 H) 1.65-1.77 (m, 5 H) 1.80-1.86 (m, 1 H) 2.1-2.19 (m, 3 H) 3.02-3.07 (m, 1 H) 3.1-3.33 (m, 4 H) 3.565 (q, J=7.6 Hz, 1 H) 3.675(q, J=7.3 Hz, 1 H) 3.87 (s, 3 H) 3.55-3.93 (m, 1H) 6.74 (d, J=8.6 Hz, 1H) 7.59 (d, J=8.3 Hz, 2 H) 7.71 (d, J=8.3 Hz, 2 H) 7.79 (d, J=8.6 Hz, 1H).

4-4 3-({4-[2-Cyclopentyl-1-(5-methoxy-thiazolo[5,4-b]pyridin-2-ylcarbamoyl)-ethyl]-benzenesulfonyl}-thiophen-2-ylmethyl-amino)-propionic acid: MS MH+ 629, 1H NMR (400 MHz, DMSO-D6) δppm 1.12-1.17 (m, 2 H) 1.41-1.44 (m, 2 H) 1.5-1.6 (m, 3 H) 1.65-1.80 (m, 3 H) 1.9-2.0 (m, 2 H) 2.07-2.14 (m, 1H) 3.24-3.29 (m, 2 H) 3.86 (s, 4 H) 4.5 (s, 2 H) 6.72 (d, J=8.6 Hz, 1H) 6.91 (m, 1 H) 6.95 (m, 1H) 7.37 (m, 1H) 7.59 (d, J=8.6 Hz, 2 H) 7.72 (d, J=8.6 Hz, 2 H) 7.7 (d, J=8.6 Hz, 1H).

4-5 4-[((2-Carboxy-ethyl)-{4-[2-cyclopentyl-1-(5-methoxy-thiazolo[5,4-b]pyridin-2-ylcarbamoyl)-ethyl]-benzenesulfonyl}-amino)-methyl]-benzoic acid: MS MH+ 667, 1H NMR (400 MHz, DMSO-d6) δ ppm 1.12 (dd, J=11.75, 5.94 Hz, 2 H) 1.43 (dd, J=7.07, 4.80 Hz, 2 H) 1.51-1.63 (m, 3 H) 1.73 (dd, J=12.88, 6.82 Hz, 3 H) 1.94 (d, J=8.34 Hz, 1 H) 1.91 (br. s., 1 H) 2.12 (ddd, J=13.26, 7.58, 7.45 Hz, 1 H) 3.19 (d, J=19.45 Hz, 2 H) 3.19 (d, J=8.59 Hz, 1 H) 3.87 (s, 4 H) 4.28 (s, 2 H) 6.72 (d, J=8.84 Hz, 1 H) 7.17 (d, J=8.08 Hz, 2 H) 7.60 (d, J=8.34 Hz, 2 H) 7.75 (dd, J=8.21, 5.68 Hz, 5 H).

4-6 3-(Cyclohexylmethyl-{4-[2-cyclopentyl-1-(5-methoxy-thiazolo[5,4-b]pyridin-2-ylcarbamoyl)-ethyl]-benzenesulfonyl}-amino)-propionic acid: MS MH+ 629, 1H NMR (400 MHz, DMSO-d6) δ ppm 0.76 (br. s., 2 H) 1.08 (br. s., 2 H) 1.11 (d, J=8.59 Hz, 3 H) 1.43 (dd, J=7.07, 4.80 Hz, 3 H) 1.56 (t, J=10.86 Hz, 8 H) 1.66 (br. s., 1 H) 1.79 (t, J=13.89 Hz, 1 H) 1.80 (d, J=13.39 Hz, 1 H) 2.13 (ddd, J=13.26, 7.83, 7.71 Hz, 1 H) 2.32 (d, J=7.83 Hz, 1 H) 2.29 (br. s., 1 H) 2.87 (d, J=7.33 Hz, 2 H) 3.26 (br. s., 1 H) 3.23 (d, J=7.83 Hz, 2 H) 3.90 (s, 3 H) 4.05 (t, J=7.58 Hz, 1 H) 6.87 (d, J=8.59 Hz, 1 H) 7.62 (d, J=8.34 Hz, 2 H) 7.76 (d, J=8.34 Hz, 2 H) 7.98 (d, J=8.84 Hz, 1 H).

4-7 3-[{4-[2-Cyclopentyl-1-(5-methoxy-thiazolo[5,4-b]pyridin-2-ylcarbamoyl)-ethyl]-benzenesulfonyl}-(5-methyl-furan-2-ylmethyl)-amino]-propionic acid: MS MH+ 627, 1H NMR (400 MHz, DMSO-d6) δ ppm 1.12 (br. s., 2 H) 1.38-1.49 (m, 2 H) 1.56 (br. s., 3 H) 1.72 (br. s., 3 H) 1.83 (s, 1 H) 2.01 (br. s., 3 H) 2.13 (br. s., 3 H) 3.20 (d, J=6.32 Hz, 2 H) 3.88 (s, 4 H) 4.31 (br. s., 2 H) 5.82 (br. s., 1 H) 6.08 (br. s., 1 H) 6.77 (d, J=8.84 Hz, 1 H) 7.54-7.62 (m, 2 H) 7.67 (d, J=8.08 Hz, 2 H) 7.84 (d, J=8.84 Hz, 1 H).

4-8 3-[{4-[2-Cyclopentyl-1-(5-methoxy-thiazolo[5,4-b]pyridin-2-ylcarbamoyl)-ethyl]-benzenesulfonyl}-(2,5-dimethyl-furan-3-ylmethyl)-amino]-propionic acid: MS MH+ 641, 1H NMR (400 MHz, DMSO-d6) δ ppm 1.11 (br. s., 3 H) 1.40 (br. s., 3 H) 1.69 (br. s., 3 H) 1.88 (br. s., 2 H) 2.11 (s, 8 H) 3.12 (br. s., 3 H) 3.64 (s, 1 H) 3.82 (s, 4 H) 3.99 (s, 2 H) 5.64 (s, 1 H) 6.59 (s, 1 H) 7.56 (s, 3 H) 7.62 (s, 2 H).

4-9 ({4-[2-Cyclopentyl-1-(5-methoxy-thiazolo[5,4-b]pyridin-2-ylcarbamoyl)-ethyl]-benzenesulfonyl}-furan-2-ylmethyl-amino)-acetic acid: MS MH+ 599, 1H NMR (400 MHz, DMSO-d6) δ ppm 1.07-1.18 (m, 1 H) 1.15 (d, J=7.83 Hz, 1 H) 1.44 (dd, J=7.20, 4.67 Hz, 2 H) 1.56 (d, J=7.83 Hz, 3 H) 1.79 (d, J=7.07 Hz, 2 H) 1.74 (d, J=18.69 Hz, 2 H) 2.11 (d, J=13.39 Hz, 1 H) 3.37 (s, 2 H) 3.90 (s, 3 H) 3.98 (br. s., 1 H) 4.57 (s, 2 H) 6.02 (d, J=2.78 Hz, 1 H) 6.19 (dd, J=3.16, 1.89 Hz, 1 H) 6.85 (d, J=8.84 Hz, 1 H) 7.34 (s, 1 H) 7.49 (d, J=8.34 Hz, 2 H) 7.76 (d, J=8.34 Hz, 2 H) 7.95 (d, J=5.81 Hz, 1 H). $EC_{50}$ in primary enzyme assay 2.4 µM 4-10 3-({4-[2-Cyclopentyl-1-(5-methoxy-thiazolo[5,4-b]pyridin-2-ylcarbamoyl)-ethyl]-benzenesulfonyl}-isopropyl-amino)-propionic acid: MS MH+ 575, 1H NMR (400 MHz, DMSO-d6) δ ppm 0.93 (d, J=6.82 Hz, 6 H) 1.11 (br. s, 2 H) 1.41 (dd, J=7.07, 4.80 Hz, 2 H) 1.58 (br. s., 2 H) 1.56 (d, J=7.33 Hz, 2 H) 1.68 (br. s., 2 H) 1.75 (dd, J=13.52, 7.20 Hz, 1 H) 2.13 (d, J=12.63 Hz, 1 H) 2.40 (d, J=8.34 Hz, 1 H) 2.37 (br. s., 1 H) 3.23 (d, J=5.31 Hz, 1 H) 3.25 (d, J=7.83 Hz, 1 H) 3.89 (s, 3 H) 3.97 (d, J=7.07 Hz, 1 H) 3.94 (d, J=6.82 Hz, 1 H) 6.83 (d, J=8.84 Hz, 1 H) 7.60 (d, J=8.59 Hz, 2 H) 7.76 (d, J=8.34 Hz, 2 H) 7.92 (d, J=8.59 Hz, 1 H).

4-11 3-[{4-[2-Cyclopentyl-1-(5-methoxy-thiazolo[5,4-b]pyridin-2-ylcarbamoyl)-ethyl]-benzenesulfonyl}-(2-methoxy-ethyl)-amino]-propionic acid: MS MH+ 591, 1H NMR (400 MHz, DMSO-d6) δ ppm 1.13 (dt, J=11.87, 7.58 Hz, 2 H) 1.42 (dd, J=7.33, 4.80 Hz, 2 H) 1.40 (d, J=1.77 Hz, 1 H) 1.50-1.62 (m, 1 H) 1.55 (d, J=5.56 Hz, 2 H) 1.67-1.79 (m, 2 H) 2.13 (dd, J=7.45, 5.68 Hz, 1 H) 2.27 (d, J=7.83 Hz, 1 H) 2.24 (br. s., 1 H) 3.14 (s, 3 H) 3.21-3.31 (m, 2 H) 3.25 (d, J=5.31 Hz, 3 H) 3.33-3.39 (m, 2 H) 3.89 (s, 3 H) 4.00 (t, J=7.45 Hz, 1 H) 6.82 (d, J=8.84 Hz, 1 H) 7.61 (d, J=8.59 Hz, 2 H) 7.75 (d, J=8.34 Hz, 2 H) 7.90 (d, J=8.84 Hz, 1 H).

4-12 3-[{4-[2-Cyclopentyl-1-(5-methoxy-thiazolo[5,4-b]pyridin-2-ylcarbamoyl)-ethyl]-benzenesulfonyl}-(1,5-dimethyl-1H-pyrazol-3-ylmethyl)-amino]-propionic acid: MS MH+ 641, 1H NMR (400 MHz, DMSO-d6) δ ppm 1.12 (br. s., 2 H) 1.42 (d, J=2.78 Hz, 2 H) 1.72 (br. s., 4 H) 2.05 (s, 4 H) 2.10 (br. s., 3 H) 3.20 (br. s., 3 H) 3.55 (s, 4 H) 3.87 (s, 5 H) 4.18 (s, 2 H) 5.57 (s, 1 H) 6.78 (s, 1 H) 7.57 (s, 2 H) 7.67 (s, 2 H) 7.83 (s, 1 H).

4-13 3-[{4-[2-Cyclopentyl-1-(5-methoxy-thiazolo[5,4-b]pyridin-2-ylcarbamoyl)-ethyl]-benzenesulfonyl}-(5-methyl-isoxazol-3-ylmethyl)-amino]-propionic acid: MS MH+ 628, 1H NMR (400 MHz, DMSO-d6) δ ppm 1.12 (br. s., 2 H) 1.41 (br. s., 2 H) 1.70 (br. s., 4 H) 2.06 (s, 4 H) 2.29 (s, 3 H) 3.24 (br. s., 4 H) 3.87 (s, 5 H) 4.35 (s, 2 H) 5.94 (s, 1 H) 6.77 (s, 1 H) 7.60 (s, 2 H) 7.72 (s, 2 H) 7.82 (s, 1 H).

4-14 3-[{4-[2-Cyclopentyl-1-(5-methoxy-thiazolo[5,4-b]pyridin-2-ylcarbamoyl)-ethyl]-benzenesulfonyl}-(tetrahydro-pyran-4-ylmethyl)-amino]-propionic acid: MS MH+ 631, 1H NMR (400 MHz, DMSO-d6) δ ppm 1.08 (td, J=12.19, 3.66 Hz, 4H) 1.42 (dd, J=7.07, 4.80 Hz, 2H) 1.38 (d, J=8.84 Hz, 1H) 1.48-1.60 (m, 5H) 1.66-1.78 (m, 4H) 2.06 (dd, J=10.61, 5.56 Hz, 2H) 2.06 (br. s., 1H) 2.91 (d, J=7.33 Hz, 2H) 3.15-3.26 (m, 4H) 3.76-3.86 (m, 6H) 6.69 (d, J=8.59 Hz, 1H) 7.58 (d, J=8.34 Hz, 2 H) 7.71 (d, J=8.84 Hz, 1 H) 7.64-7.74 (m, 2H).

4-15 3-[{4-[2-Cyclopentyl-1-(5-methoxy-thiazolo[5,4-b]pyridin-2-ylcarbamoyl)-ethyl]-benzenesulfonyl}-(4-fluoro-benzyl)-amino]-propionic acid: MS MH+ 641, 1H NMR (400 MHz, DMSO-d6) δ ppm 1.12 (br. s., 2 H) 1.43 (br. s., 3 H) 1.56 (br. s., 4 H) 1.70 (d, J=11.37 Hz, 3 H) 2.04 (d, J=8.34 Hz, 2 H) 2.12 (br. s., 1 H) 3.23 (br. s., 2 H) 3.89 (s, 4 H) 4.30 (s, 2 H) 6.82 (d, J=8.34 Hz, 1 H) 7.10 (br. s., 2 H) 7.22-7.32 (m, 2 H) 7.62 (d, J=8.34 Hz, 2 H) 7.80 (d, J=7.83 Hz, 2 H) 7.91 (d, 1 H).

4-16 3-({4-[2-Cyclopentyl-1-(5-methoxy-thiazolo[5,4-b]pyridin-2-ylcarbamoyl)-ethyl]-benzenesulfonyl}-cyclopropylmethyl-amino)-propionic acid: MS MH+ 587, 1H NMR (400 MHz, DMSO-D6) δppm 0.11-0.18 (m, 2 H) 0.36-0.43 (m, 2 H) 0.80-0.91 (m, 1 H) 1.05-1.16 (m, 2 H) 1.36-1.46 (m, 2 H) 1.50-1.61 (m, 3 H) 1.65-1.77 (m, 3 H) 2.11 (ddd, J=13.26, 7.58, 7.45 Hz, 1 H) 2.17-2.25 (m, 2 H) 2.97 (d, J=6.82 Hz, 2 H) 3.28-3.39 (m, 2 H) 3.83-3.92 (m, 4 H) 6.75 (d, J=8.59 Hz, 1 H) 7.56-7.62 (m, 2 H) 7.70 (d, J=8.34 Hz, 2 H) 7.81 (d, J=8.59 Hz, 1 H).

4-17 ({4-[2-Cyclopentyl-1-(5-methoxy-thiazolo[5,4-b]pyridin-2-ylcarbamoyl)-ethyl]-benzenesulfonyl}-methyl-amino)-acetic acid: MS MH+ 533, 1H NMR (400 MHz, DMSO-D6) δ ppm 1.07-1.18 (m, 2 H) 1.38-1.48 (m, 2 H) 1.51-1.63 (m, 3 H) 1.71 (s, 2 H) 1.76 (dd, J=13.39, 6.82 Hz, 2 H) 2.14 (dd, J=7.71, 5.68 Hz, 1 H) 2.65 (s, 3 H) 3.25 (s, 3 H) 3.90 (s, 3 H) 4.05 (s, 1 H) 6.87 (d, J=8.84 Hz, 1 H) 7.59 (d, J=8.34 Hz, 2 H) 7.75 (d, J=8.34 Hz, 2 H) 7.98 (d, J=8.84 Hz, 1 H).

4-18 3-({4-[2-Cyclopentyl-1-(5-methoxy-thiazolo[5,4-b]pyridin-2-ylcarbamoyl)-ethyl]-benzenesulfonyl}-methyl-amino)-propionic acid: MS MH+ 547, 1H NMR (400 MHz, DMSO-D6) δ ppm 1.07-1.18 (m, 2 H) 1.37-1.48 (m, 2 H) 1.51-1.63 (m, 3 H) 1.67-1.78 (m, 3 H) 2.10-2.19 (m, 1 H) 2.28 (t, J=7.45 Hz, 2 H) 2.65 (s, 3 H) 3.12 (t, J=7.45 Hz, 2 H) 3.89 (s, 3 H) 4.03 (t, J=7.45 Hz, 1 H) 6.84 (d, J=8.84 Hz, 1 H) 7.60-7.67 (m, 2 H) 7.69-7.75 (m, 2 H) 7.94 (d, J=8.84 Hz, 1 H).

4-19 3-[{4-[2-Cyclopentyl-1-(5-methoxy-thiazolo[5,4-b]pyridin-2-ylcarbamoyl)-ethyl]-benzenesulfonyl}-(tetrahydro-pyran-4-yl)-amino]-propionic acid: MS MH+ 617, 1H NMR (400 MHz, DMSO-D6) δ ppm 1.05-1.16 (m, 2 H) 1.33 (s, 2 H) 1.36-1.46 (m, 2 H) 1.52-1.61 (m, 4 H) 1.65 (dd, J=12.38, 4.55 Hz, 2 H) 2.13 (ddd, J=13.07, 7.71, 7.52 Hz, 1 H) 2.30-2.40 (m, 2 H) 3.22-3.32 (m, 5 H) 3.73-3.85 (m, 3 H) 3.89 (s, 3 H) 4.00 (t, J=7.45 Hz, 1 H) 6.83 (d, J=8.84 Hz, 1 H) 7.60 (d, J=8.34 Hz, 2 H) 7.79 (d, J=8.34 Hz, 2 H) 7.92 (d, J=8.59 Hz, 1 H).

4-20 3-(Cyclohexyl-{4-[(R)-2-cyclopentyl-1-(5-methoxy-thiazolo[5,4-b]pyridin-2-ylcarbamoyl)-ethyl]-benzenesulfonyl}-amino)-propionic acid: MS MH+ 615, 1H NMR (400 MHz, DMSO-d6) δppm 0.97 (s, 2 H) 1.18 (br. s., 3 H) 1.39 (br. s., 5 H) 1.52 (br. s., 4 H) 1.67 (br. s., 5 H) 2.15 (br. s., 3 H) 3.20 (br. s., 4 H) 3.67 (br. s., 2 H) 3.83 (s, 3 H) 6.62 (s, 1 H) 7.56 (s, 3 H) 7.64 (s, 3 H).

4-21 3-[{4-[(R)-2-Cyclopentyl-1-(5-methoxy-thiazolo[5,4-b]pyridin-2-ylcarbamoyl)-ethyl]-benzenesulfonyl}-(4-methoxy-benzyl)-amino]-propionic acid: MS MH+ 653, 1H NMR (400 MHz, DMSO-d6) δ ppm 0.85 (br. s., 2 H) 1.27 (br. s., 2 H) 1.55 (d, J=3.28 Hz, 4 H) 1.84 (br. s., 2 H) 2.11 (br. s., 1 H) 3.14 (br. s., 3 H) 3.70 (s, 4 H) 3.77 (br. s., 1 H) 3.84 (s, 4 H) 4.20 (s, 2 H) 6.67 (s, 1 H) 6.84 (s, 2 H) 7.16 (s, 2 H) 7.60 (s, 2 H) 7.70 (s, 4 H). $EC_{50}$ in primary enzyme assay 0.92 µM 4-22 ({4-[(R)-2-Cyclopentyl-1-(5-methoxy-thiazolo[5,4-b]pyridin-2-ylcarbamoyl)-ethyl]-benzenesulfonyl}-methyl-amino)-acetic acid: MS MH+ 533, 1H NMR (400 MHz, DMSO-d6) δ ppm 0.85 (br. s., 2 H) 1.27 (br. s., 2 H) 1.55 (d, J=3.28 Hz, 4 H) 1.84 (br. s., 2 H) 2.11 (br. s., 1 H) 3.14 (br. s., 3 H) 3.70 (s, 4 H) 3.77 (br. s., 1 H) 3.84 (s, 4 H) 4.20 (s, 2 H) 6.67 (s, 1 H) 6.84 (s, 2 H) 7.16 (s, 2 H) 7.60 (s, 2 H) 7.70 (s, 4 H).

4-23 3-[{4-[(R)-2-Cyclopentyl-1-(5-methoxy-thiazolo[5,4-b]pyridin-2-ylcarbamoyl)-ethyl]-benzenesulfonyl}-(2-isopropoxy-ethyl)-amino]-propionic acid: MS MH+ 619, 1H NMR (400 MHz, DMSO-d6) δppm 0.94 (s, 6 H) 1.11 (br. s., 2 H) 1.40 (br. s., 2 H) 1.69 (br. s., 3 H) 2.09 (s, 1 H) 2.22 (br. s., 2 H) 3.21 (s, 6 H) 3.35 (s, 6 H) 3.87 (s, 3 H) 3.94 (br. s., 1 H) 6.79 (s, 1 H) 7.60 (s, 2 H) 7.72 (s, 2 H) 7.84 (s, 1 H).

4-24 3-({4-[(R)-2-Cyclopentyl-1-(5-methoxy-thiazolo[5,4-b]pyridin-2-ylcarbamoyl)-ethyl]-benzenesulfonyl}-thiazol-2-ylmethyl-amino)-propionic acid: MS MH+ 630, 1H NMR (400 MHz, DMSO-d6) δ ppm 1.11 (br. s., 2 H) 1.42 (br. s., 2 H) 1.72 (br. s., 3 H) 2.06 (s, 3 H) 3.30 (br. s., 4 H) 3.86 (s, 5 H) 4.66 (s, 2 H) 6.74 (s, 1 H) 7.59 (s, 3 H) 7.65 (s, 1 H) 7.77 (s, 2 H) 7.73 (s, J=8.34 Hz, 3 H).

4-25 3-[{4-[2-Cyclopentyl-1-(5-fluoro-pyridin-2-ylcarbamoyl)-ethyl]-benzenesulfonyl}-(2-methoxy-ethyl)-amino]-propionic acid: MS MH+ 522, 1H NMR (400 MHz, DMSO-D6) δ ppm 1.08-1.18 (m, 2 H) 1.39-1.48 (m, 2 H) 1.52-1.64 (m, 3 H) 1.70 (dt, J=13.39, 6.69 Hz, 3 H) 2.07-2.15 (m, 3 H) 3.14 (s, 3 H) 3.22-3.26 (m, 4 H) 3.37 (t, J=5.94 Hz, 3 H) 4.07 (dd, J=8.34, 6.32 Hz, 1 H) 7.61 (d, J=8.34 Hz, 2 H) 7.67-7.76 (m, 3 H), 8.1 (dd, J=9.1, 4.3 Hz, 1H) 10.9 (s, 1H).

4-26 3-[{4-[(R)-2-Cyclopentyl-1-(pyrimidin-2-ylcarbamoyl)-ethyl]-benzenesulfonyl}-(2-methoxy-ethyl)-amino]-propionic acid: MS MH+ 505, 1H NMR (400 MHz, DMSO-d6) δ ppm 1.05-1.19 (m, 2H) 1.38-1.45 (m, 2H) 1.50-1.75 (m, 6H) 2.05-2.14 (m, 1H) 2.31-2.38 (m, 2H) 3.14 (s, 3H) 3.30-3.60 (m, 20H, 6H under H2O) 4.14 (m, 1H) 7.17 (t, J=4.80 Hz, 1 H) 7.61 (d, J=8.34 Hz, 2H) 7.76 (d, J=8.34 Hz, 2H) 8.63 (d, J=4.80 Hz, 2 H) 10.88 (s, 1 H).

4-27 3-[{4-[(R)-2-Cyclopentyl-1-(4-methyl-thiazol-2-ylcarbamoyl)-ethyl]-benzenesulfonyl}-2-methoxy-ethyl)-amino]-propionic acid: MS MH+ 523.

4-28 3-[{4-[(R)-2-Cyclopentyl-1-(1-methyl-1H-pyrazol-3-ylcarbamoyl)-ethyl]-benzenesulfonyl}-(2-methoxy-ethyl)-amino]-propionic acid: MS MH+ 507, 1H NMR (400 MHz, DMSO-d6) δ ppm 1.04-1.18 (m, 2H) 1.38-1.47 (m, 2H) 1.50-1.79 (m, 6H) 2.05-2.18 (m, 3H) 3.13 (s, 3H) 3.21-3.39 (m, 54H (6H under H₂O) 3.68 (s, 3H) 3.88-3.90 (m, 1H) 6.41 (d, J=2.27 Hz, 1H) 7.50 (d, J=2.02 Hz, 1H) 7.57 (d, J=8.59 Hz, 2H) 7.72 (d, J=8.34 Hz, 2H).

4-29 3-[{4-[(R)-2-Cyclopentyl-1-(pyrimidin-4-ylcarbamoyl)-ethyl]-benzenesulfonyl}-(2-methoxy-ethyl)-amino]-propionic acid: MS MH+ 505, 1H NMR (400 MHz, DMSO-d6) δ ppm 1.04-1.18 (m, 2H) 1.37-1.48 (m, 2H) 1.49-1.62 (m, 3H) 1.65-1.74 (m, 3H) 2.06-2.17 (m, 1H) 3.09-3.14 (s, 3H) 3.21-3.40 (m, 13H (6H under H2O) 4.12 (t, J=7.33 Hz, 1H) 7.60 (d, J=8.34 Hz, 2H) 7.75 (d, J=8.34 Hz, 2H) 8.05 (d, J=5.56 Hz, 1H) 8.62 (d, J=5.81 Hz, 1H) 8.85 (s, 1H) 11.26 (s, 1H).

4-30 3-[{4-[(R)-2-Cyclopentyl-1-(4,5-dimethyl-thiazol-2-ylcarbamoyl)-ethyl]-benzenesulfonyl}-(2-methoxy-ethyl)-amino]-propionic acid: MS MH+ 538, 1H NMR (400 MHz, DMSO-d6) δ ppm 1.03-1.17 (m, 2H) 1.37-1.48 (m, 2H) 1.50-1.62 (m, 3H) 1.64-1.76 (m, 3H) 2.07-2.15 (m, 4H) 2.19 (s, 3H) 2.42-2.54 (m, 13H (2H under DMSO) 3.13 (s, 3H) 3.23-3.34 (m, 4H) 3.37 (t, J=5.68 Hz) 3.96 (dd, J=8.46, 6.69 Hz, 1H) 7.58 (d, J=8.34 Hz, 2H) 7.78 (d, J=8.34 Hz, 2H) 12.18 (s, 1H).

4-31 3-[{4-[(R)-2-Cyclopentyl-1-(4,5,6,7-tetrahydro-benzothiazol-2-ylcarbamoyl)-ethyl]-benzenesulfonyl}-(2-methoxy-ethyl)-amino]-propionic acid: MS MH+ 564, 1H NMR (400 MHz, DMSO-d6) δppm 1.04-1.19 (m, 2H) 1.37-1.48 (m, 2H) 1.50-1.60 (m, 3H) 1.64-1.79 (m, 7H) 2.06-2.17 (m, 1H) 2.41-2.48 (m, 2H) 2.42-2.55 (m, 15H, 2H under DMSO) 2.60 (br s, 2H) 3.14 (s, 3H) 3.22-3.48 (m, 6H) 3.98 (dd, J=8.72, 6.44 Hz, 1H) 7.59 (d, J=8.34 Hz, 2H) 7.78 (d, J=8.59 Hz, 2H) 12.23 (s, 1H).

4-32 3-[{4-[(R)-2-Cyclopentyl-1-(pyrazin-2-ylcarbamoyl)-ethyl]-benzenesulfonyl}-(2-methoxy-ethyl)-amino]-propionic acid: MS MH+ 505, 1H NMR (400 MHz, DMSO-d6) δ ppm C391.05-1.19 (m, 2H) 1.36-1.48 (m, 2H) 1.50-1.65 (m, 3H) 1.67-1.78 (m, 3H) 2.10-2.25 (m, 3H) 3.13 (s, 3H) 3.20-3.29 (m, 4H) 3.37 (t, J=5.94 Hz, 2H) 4.12 (t, J=7.45 Hz, 1H) 7.62 (d, J=8.59 Hz, 2H) 7.76 (d, J=8.59 Hz, 2H) 8.32-8.39 (m, 2H) 9.32 (d, J=1.52 Hz, 1H) 11.14 (s, 1H).

4-33 3-[{4-[(R)-2-Cyclopentyl-1-(6-fluoro-benzothiazol-2-ylcarbamoyl)-ethyl]-benzenesulfonyl}-(2-methoxy-ethyl)-amino]-propionic acid: MS MH+ 578, 1H NMR (400 MHz, DMSO -d6) δ ppm 1.06-1.18 (m, 2 H) 1.37-1.47 (m, 2 H) 1.51-1.63 (m, 3 H) 1.67-1.78 (m, 3 H) 2.08-2.19 (m, 3 H) 3.15 (s, 3 H) 3.19-3.29 (m, 4 H) 3.37 (t, J=5.94 Hz, 2 H) 3.86-3.97 (m, 1 H) 7.12 (td, J=9.09, 2.53 Hz, 1 H) 7.52-7.63 (m, 3 H) 7.64-7.75 (m, 3 H).

4-34 3-[{3-[(R)-1-(5-Chloro-pyrimidin-2-ylcarbamoyl)-2-cyclopentyl-ethyl]-benzenesulfonyl}-(2-methoxy-ethyl)-amino]-propionic acid: MS MH+ 539, 1H NMR (400 MHz, DMSO -d6) δ ppm 1.04-1.18 (m, 2H) 1.37-1.48 (m, 2H) 1.50-1.63 (m, 3H) 1.65-1.75 (m, 3H) 1.91-2.02 (m, 2H) 2.05-2.14 (m, 1H) 3.16 (s, 3H) 3.19-3.41 (m, 1 H (6H under H2O) 4.12 (t, J=7.33 Hz, 1H) 7.53 (t, J=7.71 Hz, 1H) 7.58-7.65 (m, 2H) 7.85 (s, 1H) 8.72 (s, 2H) 11.48 (br s, 1H).

4-35 3-[{4-[(R)-1-(5-Chloro-pyrimidin-2-ylcarbamoyl)-2-cyclopentyl-ethyl]-benzenesulfonyl}-(2-methoxy-ethyl)-amino]-propionic acid: MS MH+ 539, 1H NMR (400 MHz, DMSO -d6) δ ppm 1.04-1.19 (m, 2H) 1.38-1.47 (m, 2H) 1.50-1.63 (m, 3H) 1.65-1.74 (m, 3H) 2.05-2.14 (m, 1H) 2.25 (t, J=7.71 Hz, 2H) 3.14 (s, 3H) 3.21-3.42 (m, 9H (6H under H2O) 4.12 (t, J=7.35 Hz, 1H) 7.59 (d, J=8.59 Hz, 2H) 7.75 (d, J=8.34 Hz, 2H) 8.73 (s, 2H) 11.10 (s, 1H).

4-36 3-[{4-[(R)-1-(5-Chloro-thiazol-2-ylcarbamoyl)-2-cyclopentyl-ethyl]-benzenesulfonyl}-(2-methoxy-ethyl)-amino]-propionic acid: MS MH+ 544, 1H NMR (400 MHz, DMSO -D6) δ ppm 1.04-1.15 (m, 2 H) 1.36-1.46 (m, 2 H) 1.49-1.59 (m, 3 H) 1.64-1.75 (m, 3 H) 2.09 (ddd, J=13.33, 7.83, 7.64 Hz, 1 H) 2.22-2.29 (m, 2 H) 3.15 (s, 3 H) 3.21-3.30 (m, 4 H) 3.37 (t, J=5.81 Hz, 2 H) 3.87 (t, J=7.58 Hz, 1 H) 7.30 (s, 1 H) 7.57 (d, J=8.59 Hz, 2 H) 7.72 (d, J=8.34 Hz, 2 H).

4-37 3-[{4-[(R)-1-(5-Bromo-thiazolo[5,4-b]pyridin-2-ylcarbamoyl)-2-cyclopentyl-ethyl]-benzenesulfonyl}-(2-methoxy-ethyl)-amino]-propionic acid: MS MH+ 640, 1H NMR (400 MHz, DMSO-D6) δ ppm 1.04-1.16 (m, 2 H) 1.36-1.46 (m, 2 H) 1.50-1.62 (m, 3 H) 1.65-1.74 (m, 3 H) 2.11 (ddd, J=13.14, 7.71, 7.45 Hz, 1 H) 2.28-2.35 (m, 2 H) 3.16 (s, 3 H) 3.21-3.30 (m, 4H) 3.38 (t, J=5.81 Hz, 2 H) 3.72 (t, J=7.58 Hz, 1 H) 7.32 (d, J=8.34 Hz, 1 H) 7.53-7.60 (m, 3 H) 7.66-7.71 (m, 2 H).

4-38 3-[{4-[2-Cyclopentyl-1-(5-methylsulfanyl-thiazolo[5,4-b]pyridin-2-ylcarbamoyl)-ethyl]-benzenesulfonyl}-(2-methoxy-ethyl)-amino]-propionic acid: MS MH+ 607, 1H NMR (400 MHz, DMSO-D6) δ ppm 1.04-1.15 (m, 2 H) 1.36-1.45 (dd, J=7.07, 4.80 Hz, 2 H) 1.51-1.63 (m, 2 H) 1.66-1.74 (m, 3 H) 2.01-2.13 (m, 3 H) 2.5 (s, 3H) 3.17 (s, 3 H) 3.18-3.25 (m, 4 H) 3.38 (t, J=6.19 Hz, 2 H) 3.66 (t, J=7.58 Hz, 1 H) 7.01 (d, J=8.3 Hz, 1H) 7.48 (d, J=8.3 Hz, 1H) 7.57 (d, J=8.34 Hz, 2 H) 7.65 (d, J=8.3 Hz, 2 H).

4-39 3-[{4-[2-Cyclopentyl-1-(5-methanesulfonyl-thiazolo[5,4-b]pyridin-2-ylcarbamoyl)-ethyl]-benzenesulfonyl}-(2-methoxy-ethyl)-amino]-propionic acid: MS MH+ 639, 1H NMR (400 MHz, DMSO-D6) δ ppm 1.05-1.17 (m, 2 H) 1.35-1.46 (m, 2 H) 1.51-1.62 (m, 3 H) 1.66-1.77 (m, 3 H) 2.07-2.17 (m, 2 H) 2.38-2.46 (m, 2 H) 2.74-2.82 (m, 1 H) 3.16 (s, 3H) 3.22 (s, 2 H) 3.25 (t, J=5.68 Hz, 2 H) 3.28-3.33 (m, 2 H) 3.38 (t, J=5.81 Hz, 2 H) 3.77 (t, J=7.58 Hz, 1 H) 7.60 (d, J=8.34 Hz, 2 H) 7.69-7.74 (m, 2 H) 7.75-7.82 (m, 2 H).

4-40 3-[{4-[(R)-1-(5-Chloro-quinazolin-2-ylcarbamoyl)-2-cyclopentyl-ethyl]-benzenesulfonyl}-(2-methoxy-ethyl)-amino]-propionic acid: MS MH+ 589, 1H NMR (400 MHz, DMSO -d6) δ ppm 1.06-1.19 (m, 2H) 1.38-1.49 (m, 2H) 1.51-1.60 (m, 3H) 1.63-1.79 (m, 3H) 2.09-2.21 (m, 1H) 2.29-2.39 (m, 2H) 3.13 (s, 3H) 3.23-3.39 (m, 19H (6H under H2O) 4.27 (s, 1H) 7.62-7.73 (m, 3H) 7.77 (d, J=8.34 Hz, 3H) 7.86-7.94 (m, 1H) 9.62 (s, 1H) 11.26 (s, 1H).

4-41 3-[{4-[2-Cyclopentyl-1-(thiazolo[5,4-b]pyridin-2-ylcarbamoyl)-ethyl]-benzenesulfonyl}-(2-methoxy-ethyl)-amino]-propionic acid: MS MH+ 561, 1H NMR (400 MHz, DMSO-D6) δ ppm 0.91-1.03 (m, 2 H) 1.27 (dd, J=7.20, 4.67 Hz, 2 H) 1.36-1.48 (m, 3 H) 1.51-1.61 (m, 3 H) 1.97 (dt, J=13.39, 7.58 Hz, 1 H) 2.02-2.08 (m, 2 H) 2.98-3.01 (m, 5 H) 3.05-3.14 (m, 4 H) 3.23 (t, J=5.94 Hz, 2 H) 3.65 (t, J=7.45 Hz, 1 H) 7.44 (d, J=8.34 Hz, 2 H) 7.51-7.57 (m, 3 H). $EC_{50}$ in primary enzyme assay 1.2 μM 4-42 3-[{4-[(R)-2-Cyclopentyl-1-(5-methylsulfanyl-thiazolo[5,4-b]pyridin-2-ylcarbamoyl)-ethyl]-benzenesulfonyl}-(2-methoxy-ethyl)-amino]-propionic acid: MS MH+ 607, 1H NMR (400 MHz, DMSO-D6) δppm 1.23-1.33 (m, 2 H) 1.53-1.64 (m, 2 H) 1.68-1.80 (m, 3 H) 1.83-1.92 (m, 3 H) 2.24-2.35 (m, 3 H) 2.5 (s, 3H) 3.31-3.35 (m, 3 H) 3.36-3.45 (m, 4 H) 3.51-3.58 (m, 2 H) 3.91 (t, J=7.58 Hz, 1 H) 7.25 (d, J=8.34 Hz, 1 H) 7.70-7.78 (m, 3 H) 7.82-7.87 (m, 2 H). $EC_{50}$ in primary enzyme assay 0.23 μM 4-43 3-[{4-[(R)-1-(5-Chloro-thiazolo[5,4-b]pyridin-2-ylcarbamoyl)-2-cyclopentyl-ethyl]-benzenesulfonyl}-(2-methoxy-ethyl)-amino]-propionic acid: MS MH+ 595, 1H NMR (400 MHz, DMSO-d6) δ ppm 1.03-1.15 (m, 2 H) 1.35-1.46 (m, 2 H) 1.50-1.60 (m, 3 H) 1.69 (dt, J=13.14, 6.57 Hz, 3 H) 2.06-2.15 (m, 1 H) 2.25-2.32 (m, 2 H) 3.15 (s, 3 H) 3.20-3.30 (m, 4 H) 3.34-3.40 (m, 2 H) 3.76 (s, 1 H) 7.23 (d, J=8.34 Hz, 1 H) 7.59 (d, J=8.34 Hz, 2 H) 7.68 (t, J=8.08 Hz, 3 H).

4-44 3-[(4-{(R)-2-Cyclopentyl-1-[5-(2-methoxy-ethylcarbamoyl)-thiazolo[5,4-b]pyridin-2-ylcarbamoyl]-ethyl}-benzenesulfonyl)-(2-methoxy-ethyl)-amino]-propionic acid: MS MH+ 662, 1H NMR (400 MHz, DMSO-d6) δ ppm 1.10 (td, J=12.00, 8.34 Hz, 2 H) 1.36-1.47 (m, 2 H) 1.51-1.63 (m, 3 H) 1.66-1.75 (m, 3 H) 1.94-2.02 (m, 2 H) 2.11 (ddd, J=13.14, 7.58, 7.33 Hz, 1 H) 3.17 (s, 3 H) 3.21 (t, J=6.57 Hz, 4 H) 3.26-3.33 (m, 8 H) 3.34-3.40 (m, 2 H) 3.42-3.49 (m, 4 H) 3.68 (t, J=7.58 Hz, 1 H) 7.61 (td, J=17.31, 8.34 Hz, 5 H) 7.80-7.84 (m, 1 H) 8.48 (s, 1H).

4-45 3-[{4-[(R)-2-Cyclopentyl-1-(5-morpholin-4-yl-thiazolo[5,4-b]pyridin-2-ylcarbamoyl)-ethyl]-benzenesulfonyl}-(2-methoxy-ethyl)-amino]-propionic acid: MS MH+ 646, 1H NMR (400 MHz, DMSO-d6) δ ppm 1.04-1.19 (m, 2H) 1.37-1.48 (m, 2H) 1.50-1.63 (m, 3H) 1.65-1.79 (m, 3H) 2.06-2.17 (m, 3H) 3.14 (s, 3H) 3.21-3.50 (m, 28H (10H under H2O) 3.67-3.74 (m, 4H) 3.92-3.97 (m, 1H) 6.88 (d, J=8.59 Hz, 1H) 7.59 (d, J=8.34 Hz, 2H) 7.71-7.79 (m, 3H).

4-46 3-[(4-{(R)-2-Cyclopentyl-1-[5-(2-methoxy-ethoxy)-thiazolo[5,4-b]pyridin-2-ylcarbamoyl]-ethyl}-benzenesulfonyl)-(2-methoxy-ethyl)-amino]-propionic acid: MS MH+ 635, 1H NMR (400 MHz, DMSO-d6) δ ppm 1.11 (br. s., 2 H) 1.41 (br. s., 2 H) 1.54 (br. s., 3 H) 1.71 (br. s., 3 H) 2.07 (br. s., 1 H) 2.18 (br. s., 3 H) 3.14 (s, 3 H) 3.22 (br. s., 3 H) 3.28 (s, 4 H) 3.35 (d, J=5.31 Hz, 3 H) 3.62-3.72 (m, 2 H) 3.90 (br. s., 1 H) 4.38 (d, J=4.04 Hz, 1 H) 6.77 (d, J=8.59 Hz, 1 H) 7.59 (d, J=8.08 Hz, 2 H) 7.72 (d, J=8.08 Hz, 2 H) 7.83 (br. s., 1 H). $EC_{50}$ in primary enzyme assay 0.22 μM 4-47 3-[{4-[(R)-2-Cyclopentyl-1-(5-ethyl-thiazolo[5,4-b]pyridin-2-ylcarbamoyl)-ethyl]-benzenesulfonyl}-(2-methoxy-ethyl)-amino]-propionic acid: MS MH+ 589, 1H NMR (400 MHz, DMSO-d6) δ ppm 1.06-1.17 (m, 2H) 1.24 (t, J=7.58 Hz, 3H) 1.37-1.46 (m, 2H) 1.51-1.61 (m, 3H) 1.66-1.79 (m, 3H) 2.08-2.22 (m, 3H) 2.78 (q, J=7.58 Hz, 2H) 3.15 (s, 3H) 3.20-3.30 (m, 4H) 3.37 (t, J=5.94 Hz, 2H) 3.81-3.90 (m, 1H) 7.15 (d, J=8.34 Hz, 1H) 7.59 (d, J=8.34 Hz, 2H) 7.71 (d, J=8.59 Hz, 3H).

4-48 3-{{4-[(R)-1-(5-Chloro-thiazolo[5,4-b]pyridin-2-ylcarbamoyl)-2-cyclopentyl-ethyl]-benzenesulfonyl}-[(R)-1-(tetrahydro-furan-2-yl)methyl]-amino}-propionic acid: MS MH+ 621, 1H NMR (400 MHz, DMSO-D6) δ ppm 1.05-1.16 (m, 2 H) 1.38-1.45 (m, 2 H) 1.48-1.60 (m, 5 H) 1.66-1.78 (m, 4 H) 1.80-1.90 (m, 1 H) 2.08-2.15 (m, 2H) 2.37-2.46 (m, 2 H) 3.03 (dd, J=14.53, 7.45 Hz, 1 H) 3.18-3.29 (m, 2 H) 3.32-3.41 (m, 1 H) 3.53-3.61 (m, 1 H) 3.65-3.72 (m, 1 H) 3.74-3.78 (m, 1H) 3.89 (tt, J=7.11, 3.51 Hz, 1 H) 7.24 (d, J=8.3 Hz, 1H) 7.59 (d, J=8.59 Hz, 2 H) 7.66-7.72 (m, 3 H).

4-49 3-(Benzyl-{4-[(R)-1-(5-chloro-thiazolo[5,4-b]pyridin-2-ylcarbamoyl)-2-cyclopentyl-ethyl]-benzenesulfonyl}-amino)-propionic acid: MS MH+ 627 1H NMR (400 MHz, DMSO-D6) δ ppm 1.06-1.17 (m, 2 H) 1.38-1.47 (m, 2 H) 1.52-1.64 (m, 3 H) 1.72 (ddd, J=13.33, 6.95, 6.76 Hz, 3 H) 2.02-2.14 (m, 3 H) 3.19-3.27 (m, 2 H) 3.73 (t, J=7.58 Hz, 1 H) 4.30 (s, 2 H) 7.21-7.32 (m, 5 H) 7.58-7.66 (m, 3 H) 7.74 (d, J=8.59 Hz, 2 H).

4-50 3-[{4-[(R)-2-Cyclopentyl-1-(5-fluoro-thiazolo[5,4-b]pyridin-2-ylcarbamoyl)-ethyl]-benzenesulfonyl}-(2-methoxy-ethyl)-amino]-propionic acid: MS MH+ 579, 1H NMR (400 MHz, DMSO-d6) δppm 1.09 (d, J=8.08 Hz, 2 H) 1.36-1.46 (m, 2 H) 1.53 (br. s., 2 H) 1.60 (s, 1 H) 1.64-1.74 (m, 3 H) 2.04-2.14 (m, 3 H) 3.11-3.18 (m, 3 H) 3.18-3.26 (m, 5 H) 3.36 (t, J=6.06 Hz, 3 H) 3.65 (t, J=7.58 Hz, 1 H) 6.85 (dd, J=8.59, 1.77 Hz, 1 H) 7.53-7.58 (m, 2 H) 7.62-7.73 (m, 3 H).

4-51 3-[{4-[(S)-1-(5-Chloro-thiazolo[5,4-b]pyridin-2-ylcarbamoyl)-2-cyclopentyl-ethyl]-benzenesulfonyl}-(2-methoxy-ethyl)-amino]-propionic acid: MS MH+ 595, 1H NMR (400 MHz, DMSO-d6) δ ppm 1.10 (br. s., 2 H) 1.41 (br. s., 2 H) 1.54 (br. s., 2 H) 1.69 (br. s., 2 H) 2.08 (d, J=5.05 Hz, 1 H) 2.24 (br. s., 1 H) 3.15 (s, 3 H) 3.19-3.31 (m, 7 H) 3.37 (t, J=5.94 Hz, 5 H) 3.67 (s, 1 H) 7.17 (d, J=8.34 Hz, 1 H) 7.58 (t, J=9.22 Hz, 3 H) 7.67 (d, J=8.34 Hz, 2 H). $EC_{50}$ in primary enzyme assay 44 μM 4-52 3-{{4-[(R)-1-(5-Chloro-thiazolo[5,4-b]pyridin-2-ylcarbamoyl)-2-cyclohexyl-ethyl]-benzenesulfonyl}-[(R)-1-(tetrahydro-furan-2-yl)methyl]-amino}-propionic acid: MS MH+ 635, 1H NMR (400 MHz, DMSO-d6) δ ppm 0.90 (br. s., 2 H) 1.09 (br. s., 4 H) 1.52-1.63 (m, 5 H) 1.74 (br. s., 4 H) 1.83 (d, J=11.62 Hz, 1 H) 1.94-2.05 (m, 1 H) 2.32 (br. s., 2 H) 3.03 (dd, J=14.40, 7.33 Hz, 1 H) 3.19-3.28 (m, 3 H) 3.34 (d, J=7.58 Hz, 2 H) 3.52-3.61 (m, 1 H) 3.62-3.72 (m, 1 H) 3.74-3.83 (m, 1 H) 3.84-3.93 (m, 1 H) 7.19 (d, J=8.34 Hz, 1 H) 7.54-7.64 (m, 3 H) 7.65-7.70 (m, 2 H).

4-53 3-(Benzyl-{4-[(R)-1-(5-chloro-thiazolo[5,4-b]pyridin-2-ylcarbamoyl)-2-cyclohexyl-ethyl]-benzenesulfonyl}-amino)-propionic acid: MS MH+ 641, 1H NMR (400 MHz, DMSO-D6) δ ppm 0.91 (br. s., 2 H) 1.10 (d, J=5.31 Hz, 4 H) 1.51-1.59 (m, 2 H) 1.62 (d, J=12.38 Hz, 2 H) 1.74 (br. s., 2 H) 1.86-1.96 (m, 2 H) 1.96-2.06 (m, 1 H) 3.15-3.26 (m, 2 H) 3.78 (t, J=7.58 Hz, 1 H) 4.28 (s, 2 H) 7.17 (d, J=8.34 Hz, 1 H) 7.21-7.32 (m, 5 H) 7.59 (dd, J=8.34, 6.06 Hz, 3 H) 7.71 (d, J=8.34 Hz, 2 H).

4-54 2-[(R)-2-(4-{(2-Carboxy-ethyl)-[(R)-1-(tetrahydro-furan-2-yl)methyl]-sulfamoyl}-phenyl)-3-cyclopentyl-propionylamino]-benzothiazole-6-carboxylic acid ethyl ester: MS MH+ 658, 1H NMR (400 MHz, DMSO-d6) δ ppm 1.09 (br. s., 2 H) 1.32 (t, J=7.07 Hz, 3 H) 1.40 (br. s., 2 H) 1.53 (br. s., 4 H) 1.70 (br. s., 5 H) 1.81 (br. s., 1 H) 2.12 (br. s., 3 H) 2.98-3.09 (m, 1 H) 3.10-3.20 (m, 3 H) 3.23 (br. s., 1 H) 3.28 (br. s., 2 H) 3.57 (d, J=7.33 Hz, 2 H) 3.64-3.74 (m, 2 H) 3.91 (br. s., 1 H) 4.27 (q, J=7.07 Hz, 2 H) 7.39 (d, J=8.34 Hz, 1H) 7.57 (d, J=8.08 Hz, 2 H) 7.61-7.69 (m, 2 H) 7.71-7.79 (m, 1 H) 8.19 (br. s., 1 H).

4-55 2-[(R)-2-(4-{(2-Carboxy-ethyl)-[(R)-1-(tetrahydro-furan-2-yl)methyl]-sulfamoyl}-phenyl)-3-cyclopentyl-propionylamino]-benzothiazole-6-carboxylic acid: MS MH+ 630, 1H NMR (400 MHz, DMSO-d6) δppm 1.05-1.16 (m, 2 H) 1.41 (dd, J=7.07, 4.80 Hz, 4 H) 1.50-1.58 (m, 2 H) 1.67-

1.75 (m, 3 H) 1.80-1.86 (m, 3 H) 1.93-2.02 (m, 2 H) 2.05-2.15 (m, 1 H) 2.99-3.06 (m, 1 H) 3.12-3.20 (m, 2 H) 3.22-3.31 (m, 2 H) 3.55-3.63 (m, 2 H) 3.65-3.73 (m, 1 H) 3.88-3.95 (m, 1 H) 7.14 (d, J=8.08 Hz, 1 H) 7.54-7.58 (m, 2 H) 7.60-7.66 (m, 2 H) 7.99 (d, J=1.26 Hz, 1 H).

4-56 3-[{4-[(R)-1-(5-Chloro-thiazolo[5,4-b]pyridin-2-ylcarbamoyl)-2-cyclohexyl-ethyl]-benzenesulfonyl}-(2-methoxy-ethyl)-amino]-propionic acid: MS MH+ 609, 1H NMR (400 MHz, DMSO-d6) δ ppm 0.90 (br. s., 2 H) 1.09 (br. s., 4 H) 1.58 (dd, J=13.89, 6.57 Hz, 3 H) 1.72 (br. s., 3 H) 1.95-2.06 (m, 1 H) 2.26-2.36 (m, 2H) 3.15 (s, 3 H) 3.20-3.31 (m, 4 H) 3.37 (t, J=5.56 Hz, 2 H) 3.88 (t, J=7.20 Hz, 1 H) 7.25 (d, J=8.34 Hz, 1 H) 7.58 (d, J=8.34 Hz, 2 H) 7.70 (d, J=8.34 Hz, 3 H).

4-57 3-[{4-[(R)-2-Cyclopentyl-1-(5-pyridin-4-yl-thiazolo[5,4-b]pyridin-2-ylcarbamoyl)-ethyl]-benzenesulfonyl}-(2-methoxy-ethyl)-amino]-propionic acid: MS MH+ 638, 1H NMR (400 MHz, DMSO-d6) δ ppm 1.10-1.19 (m, 2H) 1.37-1.48 (m, 2H) 1.51-1.64 (m, 3H) 1.67-1.79 (m, 3H) 2.08-2.17 (m, 1H) 2.32-2.45 (m, 2H) 3.16 (s, 3H) 3.22-3.46 (m, 21H (6H under H2O) 3.84 (br s, 1H) 7.62 (d, J=8.34 Hz, 2H) 7.73 (d, J=8.34 Hz, 2H) 7.80-7.90 (br s, 1H) 7.98-8.08 (m, 3H) 8.63 (d, J=5.81 Hz, 2H).

4-58 3-[{4-[(R)-1-(5-Chloro-thiazolo[5,4-b]pyridin-2-ylcarbamoyl)-2-cyclopentyl-ethyl]-benzenesulfonyl}-(2-methoxy-ethyl)-amino]-propionic acid tert-butyl ester: MS MH+ 651, 1H NMR (400 MHz, ACETONITRILE-d3) δppm 1.09-1.18 (m, 4 H) 1.35 (s, 9 H) 1.40-1.51 (m, 2 H) 1.55-1.66 (m, 3 H) 1.68-1.77 (m, 2 H) 1.91 (dt, J=4.86, 2.49 Hz, 2 H) 2.08-2.10 (m, 3 H) 2.13-2.21 (m, 1 H) 2.39-2.45 (m, 2 H) 3.16 (s, 3 H) 3.22-3.29 (m, 2 H) 3.32-3.40 (m, 4 H) 3.95 (t, 1 H) 7.41 (d, J=8.59 Hz, 1 H) 7.57-7.63 (m, 2 H) 7.73-7.79 (m, 2 H) 7.95 (d, J=8.59 Hz, 1 H) 10.30 (br. s., 1 H).

4-59 3-[{4-[(R)-1-(5-Chloro-thiazolo[5,4-b]pyridin-2-ylcarbamoyl)-2-cyclopentyl-ethyl]-benzenesulfonyl}-(2-methoxy-ethyl)-amino]-propionic acid benzyl ester: MS MH+ 685, 1H NMR (400 MHz, DMSO-d6). ppm 1.10 (d, J=3.54 Hz, 2 H) 1.15 (dd, J=11.49, 6.95 Hz, 2 H) 1.42 (dd, J=7.07, 4.80 Hz, 2 H) 1.50-1.62 (m, 2 H) 1.64-1.74 (m, 2 H) 1.75-1.85 (m, 1 H) 2.15 (dd, J=7.58, 5.81 Hz, 1 H) 2.63 (t, J=7.33 Hz, 2 H) 3.11 (s, 3 H) 3.24-3.32 (m, 2 H) 3.33-3.42 (m, 4 H) 4.11 (t, J=7.58 Hz, 1 H) 5.04 (s, 2 H) 7.28-7.37 (m, 5 H) 7.55 (d, J=8.34 Hz, 1 H) 7.63 (d, J=8.59 Hz, 2 H) 7.81 (d, J=8.34 Hz, 2 H) 8.14 (d, J=8.59 Hz, 1 H) 12.97 (s, 1 H).

4-60 3-[(4-{(S)-2-Cyclopentyl-1-[5-(2-methoxy-ethylcarbamoyl)-thiazolo[5,4-b]pyridin-2-ylcarbamoyl]-ethyl}-benzenesulfonyl)-(2-methoxy-ethyl)-amino]-propionic acid: MS MH+ 662, 1H NMR (400 MHz, DMSO-d6) δ ppm 1.11 (br. s., 2 H) 1.35-1.47 (m, 2 H) 1.51-1.63 (m, 3 H) 1.65-1.76 (m, 3 H) 2.12 (dd, J=14.15, 6.57 Hz, 2 H) 3.16 (s, 3 H) 3.20-3.29 (m, 8 H) 3.37 (t, J=6.06 Hz, 4 H) 3.41-3.50 (m, 4 H) 3.70 (t, J=7.58 Hz, 1 H) 7.58 (d, J=8.59 Hz, 2 H) 7.61-7.69 (m, 3 H) 7.83 (d, J=8.34 Hz, 1 H) 8.48 (s, 1 H). EC$_{50}$ in primary enzyme assay 6.0 µM 4-61 3-(Carboxymethyl-{4-[2-cyclopentyl-1-(5-methoxy-thiazolo[5,4-b]pyridin-2-ylcarbamoyl)-ethyl]-benzenesulfonyl}-amino)-propionic acid: MS MH+ 591, 1H NMR (400 MHz, DMSO-d6) δ ppm 1.10 (br. s., 2 H) 1.39 (br. s., 3 H) 1.69 (br. s., 4 H) 2.07 (s, 1 H) 2.20 (br. s., 2 H) 3.25 (br. s., 4 H) 3.40 (s, 3 H) 3.65 (br. s., 1 H) 3.82 (s, 4 H) 6.61 (s, 1 H) 7.51-7.61 (m, 3 H) 7.65 (s, 2 H).

4-62 2-{4-[2-Cyclopentyl-1-(5-methoxy-thiazolo[5,4-b]pyridin-2-ylcarbamoyl)-ethyl]-benzenesulfonylamino}-2-methyl-propionic acid: MS MH+ 547, 1H NMR (400 MHz, DMSO-D6) δ ppm 1.06-1.16 (m, 8 H) 1.37-1.46 (m, 2 H) 1.56 (ddd, J=14.53, 7.20, 7.07 Hz, 3 H) 1.64-1.71 (m, 2 H) 1.71-1.81 (m, 1 H) 2.11 (ddd, J=13.20, 7.83, 7.52 Hz, 1 H) 3.90 (s, 3 H) 4.01 (t, J=7.33 Hz, 1 H) 6.87 (d, J=8.84 Hz, 1 H) 7.54 (d, J=8.34 Hz, 2 H) 7.74 (d, J=8.34 Hz, 2 H) 7.99 (d, J=8.84 Hz, 1 H).

4-63 Succinic acid mono-[2-({4-[2-cyclopentyl-1-(5-methoxy-thiazolo[5,4-b]pyridin-2-ylcarbamoyl)-ethyl]-benzenesulfonyl}-methyl-amino)-ethyl]ester: MS MH+ 619, 1H NMR (400 MHz, DMSO-D6) δ ppm 1.06-1.17 (m, 2 H) 1.37-1.48 (m, 2 H) 1.51-1.62 (m, 3 H) 1.72 (ddd, J=13.33, 6.95, 6.76 Hz, 3 H) 2.07-2.18 (m, 1 H) 2.19-2.29 (m, 2 H) 2.29-2.37 (m, 2 H) 2.74 (s, 3 H) 3.20-3.31 (m, 2 H) 3.84-3.91 (m, 3 H) 3.99 (t, J=7.33 Hz, 1 H) 4.06 (t, J=5.43 Hz, 2 H) 6.79 (d, J=8.84 Hz, 1 H) 7.60 (d, J=8.34 Hz, 2 H) 7.73 (d, J=8.59 Hz, 2 H) 7.87 (d, J=8.84 Hz, 1 H).

4-64 (S)-2-{4-[2-Cyclopentyl-1-(5-methoxy-thiazolo[5,4-b]pyridin-2-ylcarbamoyl)-ethyl]-benzenesulfonylamino}-propionic acid: MS MH+ 533, 1H NMR (400 MHz, DMSO-D6) δ ppm 1.11 (s, 2 H) 1.15 (dd, J=6.82, 2.53 Hz, 4 H) 1.43 (dd, J=6.06, 4.55 Hz, 2 H) 1.56 (d, J=6.32 Hz, 3 H) 1.65-1.77 (m, 3 H) 2.07-2.16 (m, 1 H) 2.89-2.96 (m, 1 H) 3.86-3.95 (m, 4 H) 6.80 (d, J=8.84 Hz, 1 H) 7.52-7.60 (m, 2 H) 7.70 (d, J=7.83 Hz, 2 H) 7.88 (s, 1 H).

4-65 3-((2-Carboxy-ethyl)-{4-[2-cyclopentyl-1-(5-methoxy-thiazolo[5,4-b]pyridin-2-ylcarbamoyl)-ethyl]-benzenesulfonyl}-amino)-propionic acid: MS MH+ 605, 1H NMR (400 MHz, DMSO-d6) δppm 1.09 (br. s., 3 H) 1.41 (br. s., 3 H) 1.53 (br. s., 3 H) 2.09 (br. s., 6 H) 3.20 (br. s., 5 H) 3.74 (s, 1 H) 3.83 (s, 4 H) 6.65 (s, 1 H) 7.57 (s, 2 H) 7.60-7.68 (m, 4 H).

4-66 {4-[2-Cyclopentyl-1-(5-methoxy-thiazolo[5,4-b]pyridin-2-ylcarbamoyl)-ethyl]-benzenesulfonylamino}-acetic acid: MS MH+ 519, 1H NMR (400 MHz, DMSO-d6) δ ppm 1.11 (br. s., 3 H) 1.41 (br. s., 3 H) 1.70 (br. s., 4 H) 2.08 (s, 1 H) 2.94 (s, 2 H) 3.86 (s, 5 H) 6.75 (s, 1 H) 7.55 (s, 2 H) 7.69 (s, 3 H) 7.80 (s, 1 H).

4-67 4-{4-[2-Cyclopentyl-1-(5-methoxy-thiazolo[5,4-b]pyridin-2-ylcarbamoyl)-ethyl]-benzenesulfonylamino}-butyric acid: MS MH+ 547, 1H NMR (400 MHz, DMSO -D6) δ ppm 1.10-1.16 (m, 2 H) 1.35-1.43 (m, 2 H) 1.46-1.61 (m, 5H) 1.65-1.76 (m, 3 H) 2.0 (t, J=6.7 Hz, 2 H) 2.1 (ddd, J=13.1, 7.7, 7.5 Hz, 1 H) 2.7 (t, J=6.6 Hz, 2 H) 3.8 (t, J=7.5 Hz, 1 H) 3.9 (s, 3 H) 6.7 (d, J=8.6 Hz, 1 H) 7.55 (d, J=8.3 Hz, 2 H) 7.68 (d, J=8.3 Hz, 2 H) 7.74 (d, J=8.8 Hz, 1 H).

4-68 (Carboxymethyl-{4-[2-cyclopentyl-1-(5-methoxy-thiazolo[5,4-b]pyridin-2-ylcarbamoyl)-ethyl]-benzenesulfonyl}-amino)-acetic acid: MS MH+ 577, 1H NMR (400 MHz, DMSO-d6) δ ppm 1.07 (br. s., 3 H) 1.41 (br. s., 3 H) 1.70 (br. s., 4 H) 2.06 (s, 1 H) 3.59 (s, 5 H) 3.82 (s, 4 H) 6.55 (s, 1 H) 7.40 (s, 2 H) 7.53 (s, 1 H) 7.74 (s, 2 H).

4-69 3-[{4-[2-Cyclopentyl-1-(5-trifluoromethyl-thiazolo[5,4-b]pyridin-2-ylcarbamoyl)-ethyl]-benzenesulfonyl}-(2-methoxy-ethyl)-amino]-propionic acid: MS MH$^+$=629, 1H NMR (400 MHz, DMSO-D6) δ ppm 0.98-1.09 (m, 2 H) 1.29-1.40 (m, 2 H) 1.44-1.56 (m, 3 H) 1.58-1.68 (m, 3 H) 1.91-1.97 (m, 2 H) 2.05 (dt, J=13.20, 7.42 Hz, 1 H) 3.10 (s, 3 H) 3.12-3.18 (m, 4 H) 3.31 (t, J=6.19 Hz, 3 H) 3.63 (t, J=7.58 Hz, 1 H) 7.47-7.53 (m, 3 H) 7.57-7.61 (m, 3 H);

4-70 3-[{2-Chloro-4-[1-(5-chloro-thiazolo[5,4-b]pyridin-2-ylcarbamoyl)-2-cyclopentyl-ethyl]-benzenesulfonyl}-(2-methoxy-ethyl)-amino]-propionic acid MS MH$^+$=629 1H NMR (400 MHz, DMSO-d6) δ ppm 1.11 (br. s., 2 H) 1.41 (d, J=2.27 Hz, 2 H) 1.50-1.62 (m, 3 H) 1.64-1.74 (m, 1 H) 1.69 (d, J=6.06 Hz, 2 H) 2.08 (dd, J=7.45, 5.94 Hz, 1 H) 2.26 (br. s., 2 H) 3.13 (s, 3H) 3.40 (m, J=5.05 Hz, 3 H) 3.44 (d, J=15.41 Hz, 3 H) 3.67 (t, J=7.71 Hz, 1 H) 7.18 (d, J=8.34 Hz, 1 H) 7.48 (d, J=8.34, 1.52 Hz, 1 H) 7.64 (d, J=1.52 Hz, 1 H) 7.61 (d, J=8.34 Hz, 1 H) 7.85 (d, J=8.08 Hz, 1 H)

4-71 3-[{4-[2-Cyclopentyl-1-(5-ethyl-thiazolo[5,4-b]pyridin-2-ylcarbamoyl)-ethyl]-2-trifluoromethyl-benzenesulfonyl}-(2-methoxy-ethyl)-amino]-propionic acid MS MH$^+$=657 1H NMR (400 MHz, DMSO-d$_6$) δ ppm 1.12 (ddd, J=16.74, 11.68, 8.21 Hz, 2 H) 1.24 (t, J=7.58 Hz, 3 H) 1.42 (dd, J=7.20, 4.67 Hz, 2 H) 1.50-1.61 (m, 3 H) 1.69 (d, J=5.05 Hz, 2 H) 2.15 (ddd, J=13.33, 7.71, 7.52 Hz, 1 H) 2.32-2.39 (m, 1 H) 2.35 (d, J=7.58 Hz, 1 H) 2.79 (q, J=7.58 Hz, 2 H) 3.16 (s, 3 H) 3.39-3.50 (m, 2 H) 3.43 (dd, J=12.76, 4.42 Hz, 5 H) 3.99 (t, J=7.58 Hz, 1 H) 7.18 (d, J=8.08 Hz, 1 H) 7.75 (d, J=8.34 Hz, 1 H) 7.85 (dd, J=8.34, 1.26 Hz, 1 H) 7.97 (d, J=1.26 Hz, 1 H) 7.92-7.98 (m, 1 H)

What is claimed is:

1. A compound selected from the group consisting of
3-(Benzyl-{4-[(R)-2-cyclopentyl-1-(5-methoxy-thiazolo[5,4-b]pyridin-2-ylcarbamoyl)-ethyly]-benzenesulfonyl}-amino)-propionic acid,
3-(Benzofuran-2-ylmethyl-{4-[(R)-2-cyclopentyl-1-(5-methoxy-thiazolo[5,4-b]pyridin-2-ylcarbamoyl)-ethyl]-benzenesulfonyl}-amino)-propionic acid,
3-({4-[(R)-2-Cyclopentyl-1-(5-methoxy-thiazolo[5,4-b]pyridin-2-ylcarbamoyl)-ethyl]-benzenesulfonyl}-pyridin-2-ylmethyl-amino)-propionic acid,
3-({4-[(R)-2-Cyclopentyl-1-(5-methoxy-thiazolo[5,4-b]pyridin-2-ylcarbamoyl)-ethyl]-benzenesulfonyl}-oxazol-2-ylmethyl-amino)-propionic acid,
3-[{4-[(R)-2-Cyclopentyl-1-(5-methoxy-thiazolo[5,4-b]pyridin-2-ylcarbamoyl)-ethyl]-benzenesulfonyl}-(tetrahydro-furan-2-ylmethyl)-amino]-propionic acid,
3-({4-[(R)-2-Cyclopentyl-1-(5-methoxy-thiazolo[5,4-b]pyridin-2-ylcarbamoyl)-ethyl]-benzenesulfonyl}-thiophen-2-ylmethyl-amino)-propionic acid,
4-[((2-Carboxy-ethyl)-{4-[(R)-2-cyclopentyl-1-(5-methoxy-thiazolo[5,4-b]pyridin-2-ylcarbamoyl)-ethyl]-benzenesulfony}-amino)-methyl]-benzoic acid,
3-(Cyclohexylmethyl-{4-[(R)-2-cyclopentyl-1-(5-methoxy-thiazolo[5,4-b]pyridin-2-ylcarbamoyl)-ethyl]-benzenesulfonyl}-amino)-propionic acid,
3-[{4-[(R)-2-Cyclopentyl-1-(5-methoxy-thiazolo[5,4-b]pyridin-2-ylcarbamoyl)-ethyl]-benzenesulfonyl}-(5-methyl-furan-2-ylmethyl)-amino]-propionic acid,
3-[{4-[(R)-2-Cyclopentyl-1-(5-methoxy-thiazolo[5,4-b]pyridin-2-ylcarbamoyl)-ethyl]-benzenesulfonyl}-(2,5-dimethyl-furan-3-ylmethyl)-amino]-propionic acid,
({4-[(R)-2-Cyclopentyl-1-(5-methoxy-thiazolo[5,4-b]pyridin-2-ylcarbamoyl)-ethyl]-benzenesulfonyl}-furan-2-ylmethyl-amino)-acetic acid,
3-({4-[(R)-2-Cyclopentyl-1-(5-methoxy-thiazolo[5,4-b]pyridin-2-ylcarbamoyl)-ethyl]-benzenesulfonyl}-isopropyl-amino)-propionic acid,
3-[{4-[(R)-2-Cyclopentyl-1-(5-methoxy-thiazolo[5,4-b]pyridin-2-ylcarbamoyl)-ethyl]-benzenesulfonyl}-(2-methoxy-ethyl)-amino]-propionic acid,
3-[{4-[(R)-2-Cyclopentyl-1-(5-methoxy-thiazolo[5,4-b]pyridin-2-ylcarbamoyl)-ethyl]-benzenesulfonyl}-(1,5-dimethyl-1H-pyrazol-3-ylmethyl)-amino]-propionic acid,
3-[{4-[(R)-2-Cyclopentyl-1-(5-methoxy-thiazolo[5,4-b]pyridin-2-ylcarbamoyl)-ethyl]-benzenesulfonyl}-(5-methyl-isoxazol-3-ylmethyl)-amino]-propionic acid,
3-[{4-[(R)-2-Cyclopentyl-1-(5-methoxy-thiazolo[5,4-b]pyridin-2-ylcarbamoyl)-ethyl]-benzenesulfonyl}-(tetrahydro-pyran-4-ylmethyl)-amino]-propionic acid,
3-[{4-[(R)-2-Cyclopentyl-1-(5-methoxy-thiazolo[5,4-b]pyridin-2-ylcarbamoyl)-ethyl]-benzenesulfonyl}-(4-fluoro-benzyl)-amino]-propionic acid,
3-({4-[(R)-2-Cyclopentyl-1-(5-methoxy-thiazolo[5,4-b]pyridin-2-ylcarbamoyl)-ethyl]-benzenesulfonyl}-cyclopropylmethyl-amino)-propionic acid,
{4-[(R)-2-Cyclopentyl-1-(5-methoxy-thiazolo[5,4-b]pyridin-2-ylcarbamoyl)-ethyl]-benzenesulfonyl}-methyl-amino)-acetic acid,
3-({4-[(R)-2-Cyclopentyl-1-(5-methoxy-thiazolo[5,4-b]pyridin-2-ylcarbamoyl)-ethyl]-benzenesulfonyl}-methyl-amino)-propionic acid,
3-[{4-[(R)-2-Cyclopentyl-1-(5-methoxy-thiazolo[5,4-b]pyridin-2-ylcarbamoyl)-ethyl]-benzenesulfonyl}-(tetrahydro-pyran-4-yl)-amino]-propionic acid,
3-(Cyclohexyl-{4-[(R)-2-cyclopentyl-1-(5-methoxy-thiazolo[5,4-b]pyridin-2-ylcarbamoyl)-ethyl]-benzenesulfonyl}-amino)-propionic acid,
3-[{4-[(R)-2-Cyclopentyl-1-(5-methoxy-thiazolo[5,4-b]pyridin-2-ylcarbamoyl)-ethyl]-benzenesulfonyl}-(4-methoxy-benzyl)-amino]-propionic acid,
({4-[(R)-2-Cyclopentyl-1-(5-methoxy-thiazolo[5,4-b]pyridin-2-ylcarbamoyl)-ethyl]-benzenesulfonyl}-methyl-amino)-acetic acid,
3-[{4-[(R)-2-Cyclopentyl-1-(5-methoxy-thiazolo[5,4-b]pyridin-2-ylcarbamoyl)-ethyl]-benzenesulfonyl}-(2-isopropoxy-ethyl)-amino]-propionic acid,
3-({4-[(R)-2-Cyclopentyl-1-(5-methoxy-thiazolo[5,4-b]pyridin-2-ylcarbamoyl)-ethyl]-benzenesulfonyl}-thiazol-2-ylmethyl-amino)-propionic acid,
3-[{4-[(R)-1-(5-Bromo-thiazolo[5,4-b]pyridin-2-ylcarbamoyl)-2-cyclopentyl-ethyl]-benzenesulfonyl}-(2-methoxy-ethyl)-amino]-propionic acid,
3-[{4-[(R)-2-Cyclopentyl-1-(5-methylsulfanyl-thiazolo[5,4-b]pyridin-2-ylcarbamoyl)-ethyl]-benzenesulfonyl}-(2-methoxy-ethyl)-amino]-propionic acid,
3-[{4-[(R)-2-Cyclopentyl-1-(5-methanesulfonyl-thiazolo[5,4-b]pyridin-2-ylcarbamoyl)-ethyl]-benzenesulfonyl}-(2-methoxy-ethyl)-amino]-propionic acid,
3-[{4-[(R)-2-Cyclopentyl-1-(thiazolo[5,4-b]pyridin-2-ylcarbamoyl)-ethylybenzenesulfonyl}-(2-methoxy-ethyl)-amino]-propionic acid,
3-[{4-[(R)-2-Cyclopentyl-1-(5-methylsulfanyl-thiazolo[5,4-b]pyridin-2-ylcarbamoyl)-ethyl]-benzenesulfonyl}-(2-methoxy-ethyl)-amino]-propionic acid,
3-[{4-[(R)-1-(5-Chloro-thiazolo[5,4-b]pyridin-2-ylcarbamoyl)-2-cyclopentyl-ethyl]-benzenesulfonyl}-(2-methoxy-ethyl)-amino]-propionic acid,
3-[(4-{(R)-2-Cyclopentyl-1-[5-(2-methoxy-ethylcarbamoyl)-thiazolo[5,4-b]pyridin-2-ylcarbamoyl]-ethyl}-benzenesulfonyl)-(2-methoxy-ethyl)-amino]-propionic acid,
3-[{4-[(R)-2-Cyclopentyl-1-(5-morpholin-4-yl-thiazolo[5,4-b]pyridin-2-ylcarbamoyl)-ethyl]-benzenesulfonyl}-(2-methoxy-ethyl)-amino]-propionic acid,
3-[(4-{(R)-2-Cyclopentyl-1-[5-(2-methoxy-ethoxy)-thiazolo[5,4-b]pyridin-2-ylcarbamoyl]-ethyl}-benzenesulfonyl)-(2-methoxy-ethyl)-amino]-propionic acid,
3-[{4-[(R)-2-Cyclopentyl-1-(5-ethyl-thiazolo[5,4-b]pyridin-2-ylcarbamoyl)-ethyl]-benzenesulfonyl}-(2-methoxy-ethyl)-amino]-propionic acid,
3-{{4-[(R)-1-(5-Chloro-thiazolo[5,4-b]pyridin-2-ylcarbamoyl)-2-cyclopentyl-ethyl]-benzenesulfonyl}-[(R)-1-(tetrahydro-furan-2-yl)methyl]-amino}-propionic acid,
3-(Benzyl-{4-[(R)-1-(5-chloro-thiazolo[5,4-b]pyridin-2-ylcarbamoyl)-2-cyclopentyl-ethyl]-benzenesulfonyl}-amino)-propionic acid, 3-[{4-[(R)-2-Cyclopentyl-1-(5-fluoro-thiazolo[5,4-b]pyridin-2-ylcarbamoyl)-ethyl]-benzenesulfonyl}-(2-methoxy-ethyl)-amino]-propionic acid, 3-{{4-[(R)-1-(5-Chloro-thiazolo[5,4-b]pyridin-2-ylcarbamoyl)-2-cyclohexyl-ethyl]-benzenesulfonyl}-[(R)-1-(tetrahydro-furan-2-yl)methyl]-amino}-propionic acid, 3-(Benzyl-{4-[(R)-1-(5-chloro-thiazolo[5,4-b]pyridin-2-ylcarbamoyl)-2-cyclohexyl-ethyl]-benzenesulfonyl}-amino)-propionic acid, 3-[{4-[(R)-1-(5-Chloro-thiazolo[5,4-b]pyridin-2-ylcarbamoyl)-2-cyclohexyl-ethyl]-benzenesulfonyl}-(2-methoxy-ethyl)-amino]-propionic acid, 3-[{4-[(R)-2-Cyclopentyl-1-(5-pyridin-4-yl-thiazolo[5,4-b]pyridin-2-ylcarbamoyl)-ethyl]-benzenesulfonyl}-(2-methoxy-ethyl)-amino]-propionic acid, 3-[{4-[(R)-1-(5-Chloro-thiazolo[5,4-b]pyridin-2-ylcarbamoyl)-2-cyclopentyl-ethyl]-benzenesulfonyl}-(2-methoxy-ethyl)-amino]-propionic acid tert-butyl ester 3-[{4-[(R)-1-(5-Chloro-thiazolo[5,4-b]pyridin-2-ylcarbamoyl)-2-cyclopentyl-ethyl]-benzenesulfonyl}-(2-methoxy-ethyl)-amino]-propionic acid benzyl ester, 3-(Carboxymethyl-{4-[(R)-2-cyclopentyl-1-(5-methoxy-thiazolo[5,4-b]pyridin-2-ylcarbamoyl)-ethyl]-benzenesulfonyl}-amino)-propionic acid, 2-{4-[(R)-2-Cyclopentyl-1-(5-methoxy-thiazolo[5,4-b]pyridin-2-ylcarbamoyl)-ethyl]-benzenesulfonylamino}-2-methyl-propionic acid, Succinic acid mono-[2-({4-[(R)-2-cyclopentyl-1-(5-methoxy-thiazolo[5,4-b]pyridin-2-ylcarbamoyl)-ethyl]-benzenesulfonyl}-methyl-amino)-ethyl] ester, (S)-2-{4-[(R)-2-Cyclopentyl-1-(5-methoxy-thiazolo[5,4-b]pyridin-2-ylcarbamoyl)-ethyl]-benzenesulfonylamino}-propionic acid, 3-((2-Carboxy-ethyl)-{4-[(R)-2-cyclopentyl-1-(5-methoxy-thiazolo[5,4-b]pyridin-2-ylcarbamoyl)-ethyl]-benzenesulfonyl}-amino)-propionic acid {4-[(R)-2-Cyclopentyl-1-(5-methoxy-thiazolo[5,4-b]pyridin-2-ylcarbamoyl)-ethyl]-benzenesulfonylamino}-acetic acid, 4-{4-[(R)-2-Cyclopentyl-1-(5-methoxy-thiazolo[5,4-b]pyridin-2-ylcarbamoyl)-ethyl]-benzenesulfonylamino}butyric acid, (Carboxymethyl-{4-[(R)-2-cyclopentyl-1-(5-methoxy-thiazolo[5,4-b]pyridin-2-ylcarbamoyl-ethyl]-benzenesulfonyl}-amino)-acetic acid, 3-[{4-[(R)-2-Cyclopentyl-1-(5-trifluoromethyl-thiazolo[5,4-b]pyridin-2-ylcarbamoyl)-ethyl]-benzenesulfonyl}-(2-methoxy-ethyl)-amino]-propionic acid, 3-[{2-Chloro-4-[(R)-1-(5-chloro-thiazolo[5,4-b]pyridin-2-ylcarbamoyl)-2-cyclopentyl-ethyl]-benzenesulfonyl}-(2-methoxy-ethyl)-amino]-propionic acid, and 3-[{4-[(R)-2-Cyclopentyl-1-(5-ethyl-thiazolo[5,4-b]pyridin-2-ylcarbamoyl)-ethyl]-2-trifluoromethyl-benzenesulfonyl}-(2-methoxy-ethyl)-amino]-propionic acid, or a pharmaceutically acceptable salt thereof.

2. A method for the activation of glucokinase activity in mammals, comprising:
administering to a mammal, in need thereof, a therapeutically effective amount of a compound of claim 1, or a pharmaceutically acceptable salt thereof.

3. A pharmaceutical composition, comprising:
a therapeutically effective amount of a compound of claim 1, or a pharmaceutically acceptable salt thereof, in combination with one or more pharmaceutically acceptable carriers.

4. The compound 3-[{4-[(R)-1-(5-Chloro-thiazolo[5,4-b]pyridin-2-ylcarbamoyl)-2-cyclopentyl-ethyl]benzenesulfonyl}-(2-methoxy-ethyl)-amino]-propionic acid, or a pharmaceutically acceptable salt thereof.

5. A method for the activation of glucokinase activity in mammals, comprising:
administering to a mammal, in need thereof, a therapeutically effective amount of a compound of claim 4, or a pharmaceutically acceptable salt thereof.

6. A pharmaceutical composition, comprising:
a therapeutically effective amount of a compound of claim 4, or a pharmaceutically acceptable salt thereof, in combination with one or more pharmaceutically acceptable carriers.

7. The compound 3-[{4-[(R)-2-Cyclopentyl-1-(5-ethyl-thiazolo[5,4-b]pyridin-2-ylcarbamoyl)-ethyl]-benzenesulfonyl}-(2-methoxy-ethyl)-amino]-propionic acid, or a pharmaceutically acceptable salt thereof.

8. A method for the activation of glucokinase activity in mammals, comprising:
administering to a mammal, in need thereof, a therapeutically effective amount of a compound of claim 7, or a pharmaceutically acceptable salt thereof.

9. A pharmaceutical composition, comprising:
therapeutically effective amount of a compound of claim 7, or a pharmaceutically acceptable salt thereof, in combination with one or more pharmaceutically acceptable carriers.

\* \* \* \* \*